US008731863B2

(12) United States Patent
Mishima et al.

(10) Patent No.: US 8,731,863 B2
(45) Date of Patent: May 20, 2014

(54) ANALYZING SYSTEM, DATA PROCESSING APPARATUS, AND STORAGE MEDIUM

(75) Inventors: Yoshihiro Mishima, Kobe (JP); Terutaka Yauchi, Hiroshima (JP)

(73) Assignee: Sysmex Corporation, Kobe (JP)

( * ) Notice: Subject to any disclaimer, the term of this patent is extended or adjusted under 35 U.S.C. 154(b) by 632 days.

(21) Appl. No.: 11/395,854

(22) Filed: Mar. 30, 2006

(65) Prior Publication Data

US 2006/0259265 A1 Nov. 16, 2006

(30) Foreign Application Priority Data

Mar. 30, 2005 (JP) ................................. 2005-096685

(51) Int. Cl.
*G01N 31/00* (2006.01)
(52) U.S. Cl.
USPC .............................. 702/127; 702/31; 702/32
(58) Field of Classification Search
USPC .............. 702/21, 22, 127, 182, 183; 600/368, 600/369
See application file for complete search history.

(56) References Cited

U.S. PATENT DOCUMENTS

| | | | | |
|---|---|---|---|---|
| 5,793,969 A | * | 8/1998 | Kamentsky et al. | 709/213 |
| 7,041,468 B2 | * | 5/2006 | Drucker et al. | 435/14 |
| 2002/0026292 A1 | * | 2/2002 | Isami | 702/188 |
| 2003/0036683 A1 | * | 2/2003 | Kehr et al. | 600/300 |
| 2003/0120462 A1 | * | 6/2003 | Yundt-Pacheco | 702/182 |
| 2003/0212579 A1 | * | 11/2003 | Brown et al. | 705/2 |
| 2004/0176667 A1 | * | 9/2004 | Mihai et al. | 600/300 |
| 2005/0130236 A1 | * | 6/2005 | Goldman | 435/7.21 |

FOREIGN PATENT DOCUMENTS

| | | | | |
|---|---|---|---|---|
| JP | 05-307041 | | 11/1993 | |
| JP | 09-274044 | | 10/1997 | |
| JP | 2000-329685 | | 11/2000 | |
| JP | 2003-202346 | | 7/2003 | |
| WO | WO 02/068963 A1 | * | 9/2002 | G01N 35/00 |

* cited by examiner

*Primary Examiner* — John Breene
*Assistant Examiner* — Timothy H Hwang
(74) *Attorney, Agent, or Firm* — Brinks Gilson & Lione

(57) ABSTRACT

An analyzing system, data processing apparatus, and application program are provided that can display the measurement results and/or analysis results of a plurality of different types of measuring apparatuses on a user interface that is easily comprehended by the user. The data processing apparatus is capable of displaying on a screen the measurement results and analysis results of a plurality of measuring apparatuses that perform mutually different kinds of measurements of specimens. A plurality of measurement item group switching buttons are provided on the display screen, and specimen information tables that correspond to each measurement item can be displayed by a user clicking on the buttons.

17 Claims, 41 Drawing Sheets

FIG.27

| | Specimen num | Output | P/N | Time | WBC | RBC | HGB | HCT | MCV | MCH | MCHC | PLT |
|---|---|---|---|---|---|---|---|---|---|---|---|---|
| F | XE-001 | DGH | XE1 | 10:15 | 4.86 | 4.53 | 13.1 | 38.1 | 84.1 | 28.9 | 34.4 | 182 |
| F | XE-002 | DG | XE2 | 10:30 | 4.86 | 4.53 | 13.1 | 38.1 | 84.1 | 28.9 | 34.4 | 182 |
| F | XE-003 | DG | XE1 | 10:35 | 4.86 | 4.53 | 13.1 | 38.1 | 84.1 | 28.9 | 34.4 | 182 |
| F | XE-004 | DG | XE2 | 10:40 | 4.86 | 4.53 | 13.1 | 38.1 | 84.1 | 28.9 | 34.4 | 182 |
| F | XE-005 | DG | XE1 | 10:55 | 4.86 | 4.53 | 13.1 | 38.1 | 84.1 | 28.9 | 34.4 | 182 |
| F | XE-006 | DG | XE2 | 11:05 | 4.86 | 4.53 | 13.1 | 38.1 | 84.1 | 28.9 | 34.4 | 182 |
| F | XE-007 | DG | XE1 | 11:25 | 4.86 | 4.53 | 13.1 | 38.1 | 84.1 | 28.9 | 34.4 | 182 |

| ITEM | DATA | UNITS |
|---|---|---|
| WBC | 4.86 | 10^3/uL |
| RBC | 4.53 | 10^6/uL |
| HGB | 13.1 | g/dL |
| HCT | 38.1 | % |
| MCV | 84.1 | fL |
| MCH | 28.9 | Pg |
| MCHC | 34.4 | g/dL |
| PLT | 182 | 10^3/uL |
| RDW-SD | 38.4 | fL |
| RDW-CV | 12.5 | % |
| PDW | 9.8 | fL |
| MPV | 9.1 | fL |
| P-LCR | 17.4 | % |
| PCT | 0.17 | % |
| NEUT# | 2.02 | 10^3/uL |
| LYMPH# | 2.36 | 10^3/uL |
| MONO# | 0.39 | 10^3/uL |
| EO# | 0.08 | 10^3/uL |
| BASO# | 0.01 | 10^3/uL |
| NEUT% | 41.6 | % |
| LYMPH% | 48.6 | % |
| MONO% | 8.0 | % |
| EO% | 1.6 | % |
| BASO% | 0.2 | % |
| NRBC# | 0.00 | /100WBC |
| NRBC% | 0.0 | % |
| RET% | 1.82 | % |
| RET# | 0.087 | 10^6/uL |
| IRF | 5.3 | % |
| LFR | 94.7 | % |
| MFR | 5.1 | % |
| HFR | 0.2 | % |

Specimen | CBC | DIFF | RET | Patient

Patient number: 00-0023-1
Last name: Sysmex
First name: Taro
Sex: Male
Patient comment:
Date of birth: 1943/01/15
Ward: 01
Attending physician: 0839

FIG.29

| Item | Data | Units |
|---|---|---|
| WBC | 4.86 | 10^3/uL |
| RBC | 4.53 | 10^6/uL |
| HGB | 13.1 | g/dL |
| HCT | 38.1 | % |
| MCV | 84.1 | fL |
| MCH | 28.9 | Pg |
| MCHC | 34.4 | g/dL |
| PLT | 182 | 10^3/uL |
| RDW-SD | 38.4 | fL |
| RDW-CV | 12.5 | % |
| PDW | 9.8 | fL |
| MPV | 9.1 | fL |
| P-LCR | 17.4 | % |
| PCT | 0.17 | % |
| RET# | 1.92 | 10^6/uL |
| RET% | 0.087 | % |
| IRF | 5.3 | % |
| LFR | 94.7 | % |
| MFR | 5.1 | % |
| HFR | 0.2 | % |
| NRBC# | 0.00 | 10^3/uL |
| NRBC% | 0.0 | /100WBC |

WBC Differential

| Item | Data | Units |
|---|---|---|
| NEUT# | 2.02 | 10^3/uL |
| LYMPH# | 2.36 | 10^3/uL |
| MONO# | 0.39 | 10^3/uL |
| EO# | 0.08 | 10^3/uL |
| BASO# | 0.01 | 10^3/uL |

| Item | Data | Units |
|---|---|---|
| NEUT% | 41.6 | % |
| LYMPH% | 48.6 | % |
| MONO% | 8.0 | % |
| EO% | 1.6 | % |
| BASO% | 0.2 | % |

Specimen number: 21913031
Patient ID: 00-0023-1
Patient name: Sysmex, Taro
Date of birth: 1943/01/15
Sex: Male
Comment:
Ward: 01
Physician: 0839
Date: 2004/11/30
Time: 17:01

NEGATIVE

Flag
WBC
RBC/RET
PLT

ANALYZING SYSTEM, DATA PROCESSING APPARATUS, AND STORAGE MEDIUM

RELATED APPLICATIONS

This application claims priority under 35 U.S.C. §119 to Japanese Patent Application No. 2005-96685 filed Mar. 30, 2005, the entire content of which is hereby incorporated herein by reference.

TECHNICAL FIELD

The present invention relates to an analyzing system used to measure a specimen, data processing apparatus used in the analyzing system, and computer readable storage medium recording computer programs that enable a computer to function as a data processing apparatus.

BACKGROUND

Measuring apparatuses for measuring blood specimens, urine specimens, and the various shapes of particle specimens and the like are known as blood analyzers, urine analyzers, and particle analyzers. Since this type of measuring apparatus must process measurement data and manage measurement results and analysis results, a data processing apparatus configured by a computer on which is installed application programs used for such processing and data management is provided separately from the measuring apparatus, and the data processing apparatus is configured so as to process the measurement data and display and manage the measurement results (for example, refer to Japanese Laid-Open Patent Publication No. 2003-202346).

An testing system has been disclosed in which a plurality of automatic chemical analyzers (measuring apparatuses) and a lesser number of data processing apparatuses are provided, and a single data processing apparatus is used commonly by a plurality of automatic chemical analyzers (refer to Japanese Laid-Open Patent Publication No. 5-307041). In this testing system, a single data processing apparatus can be used by a plurality of different types of automatic chemical analyzers.

In the system disclosed in Japanese Laid-Open Patent Publication No. 5-307041, however, although analysis data of various automatic chemical analyzers can be processed by a data processing apparatus and the data processing results can be displayed on a screen, it is unclear where the respective data processing results are to be displayed. Measurement results and analysis results of multiple measuring apparatuses that are simply displayed on one screen must be verified by a user concerning which measuring apparatus corresponds to the respective measurement results and analysis results, thus confronting the user with a difficult to manage screen display user interface. Furthermore, there are measuring apparatuses that have a plurality of types of operating modes (measurement channels), and in these cases, the labor of the user is increased inasmuch as the user must decide the operating modes that correspond to the respectively displayed measurement results and analysis results.

SUMMARY

The scope of the present invention is defined solely by the appended claims, and is not affected to any degree by the statements within this summary.

The first aspect of the present invention relates to an analyzing system for analyzing a specimen comprising: a plurality of measuring apparatuses for performing mutually different types of measurements of specimens; and a data processing apparatus for analysis of measurement results obtained by the plurality of measuring apparatuses, wherein the data processing apparatus comprises a display unit for selectively switching and displaying the measurement results and/or analysis results in accordance with the type of measurement.

The second aspect of the present invention relates to a data processing apparatus for analyzing measurement results of measuring apparatuses for measuring specimens, comprising: receiving means for respectively receiving the measurement results from a plurality of measuring apparatuses that perform mutually different types of measurements of specimens; analysis processing means for performing analysis of measurement results respectively received from the plurality of measuring apparatuses; and a display unit for selectively switching and displaying the measurement results and/or analysis results in accordance with the type of measurement.

The third aspect of the present invention relates to a computer readable storage medium for recording a computer program used for processing measurement result of measuring apparatus that measure a specimen, wherein the computer program comprises: receiving means for enabling a computer to function so as to receive measurement results from a plurality of measuring apparatuses respectively; analysis processing means for enabling the computer to function so as to analyze measurement data received from the plurality of measuring apparatuses; and display means for enabling the computer to function so as to selectively switch and display the measurement results and/or the analysis results according to the type of measurement.

BRIEF DESCRIPTION OF THE DRAWINGS

FIG. 27 is a schematic view of an example of the structure of a measurement result display window of the application program used on the hemocyte analyzer of the first embodiment;

FIG. 29 is a schematic view of an example of the structure of a measurement result detail information display window of the application program used on the hemocyte analyzer of the first embodiment;

FIG. 31 is a schematic view of an example of the structure of a measurement result display window of the application program used on the blood coagulation measuring apparatus of the first embodiment;

FIG. 32 is a schematic view of an example of the structure of a measurement result detail information display window of the application program used on the blood coagulation measuring apparatus of the first embodiment;

FIG. 33 is a schematic view showing the structure of the measurement result display window of the application program used for measurement result reference of the hemocyte analyzer and blood coagulation measuring apparatus of the first embodiment;

FIG. 34 is a schematic view showing the structure of the measurement result detail information display window of the application program used for measurement result reference of the hemocyte analyzer and blood coagulation measuring apparatus of the first embodiment;

DESCRIPTION OF THE PREFERRED EMBODIMENTS

The embodiments of the analysis system, data processing apparatus, measuring apparatus, and application program are described hereinafter with reference to the drawings.

First Embodiment

Figure 1:
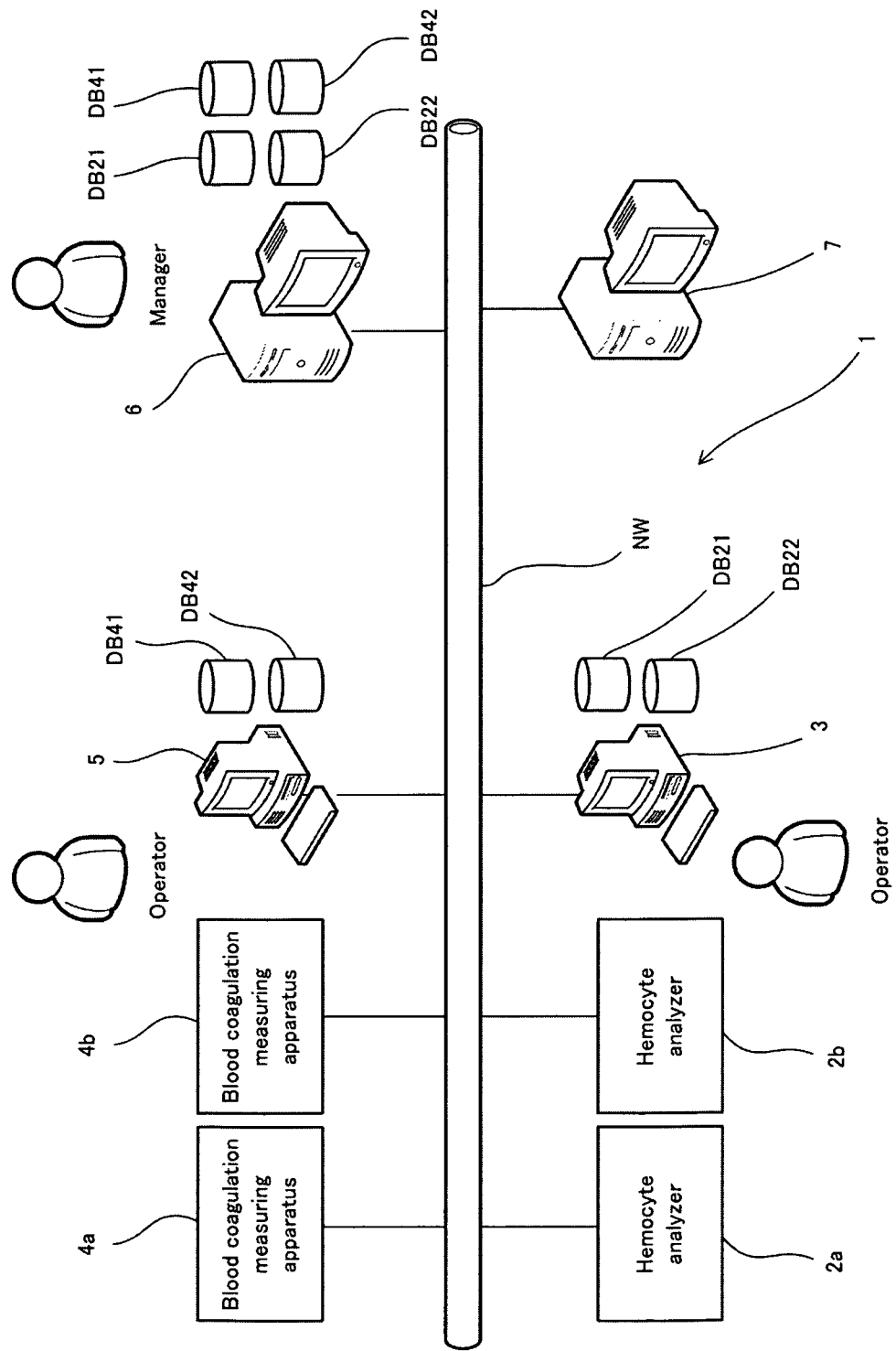
FIG. 1 is a schematic view showing the structure of an analysis system of the first embodiment.

FIG. 1 is a schematic view showing the structure of the analysis system of a first embodiment. As shown in FIG. 1, the analysis system 1 of the first embodiment has essential structural elements that include hemocyte analyzers 2a and 2b, data processing apparatus 3 for hemocyte analyzers 2a and 2b, blood coagulation measuring apparatuses 4a and 4b, data processing apparatus 5 for blood coagulation measuring apparatuses 4a and 4b, data processing apparatus 6 used for all hemocyte analyzers 2a and 2b and blood coagulation measuring apparatuses 4a and 4b, and patient data management database server 7. The hemocyte analyzers 2a and 2b, data processing apparatus 3, blood coagulation measuring apparatuses 4a and 4b, data processing apparatus 5, data processing apparatus 6, and database server 7 are installed within an medical institution such as, for example, a hospital or pathology research facility. Furthermore, the hemocyte analyzers 2a and 2b, data processing apparatus 3, blood coagulation measuring apparatuses 4a and 4b, data processing apparatus 5, and data processing apparatus 6, may be provided, for example, in a pathology research facility, and the database server 7 may be installed in a hospital or the like, such that the apparatuses configuring the analysis system 1 are separately provided at a plurality of institutions. The hemocyte analyzers 2a and 2b, data processing apparatus 3, blood coagulation measuring apparatuses 4a and 4b, data processing apparatus 5, data processing apparatus 6, and database server 7 are connected by means of a communication network NW, such as the internet, a LAN, dedicated line using a telephone line or the like, so as to be capable of mutual data communication.

Figure 2:
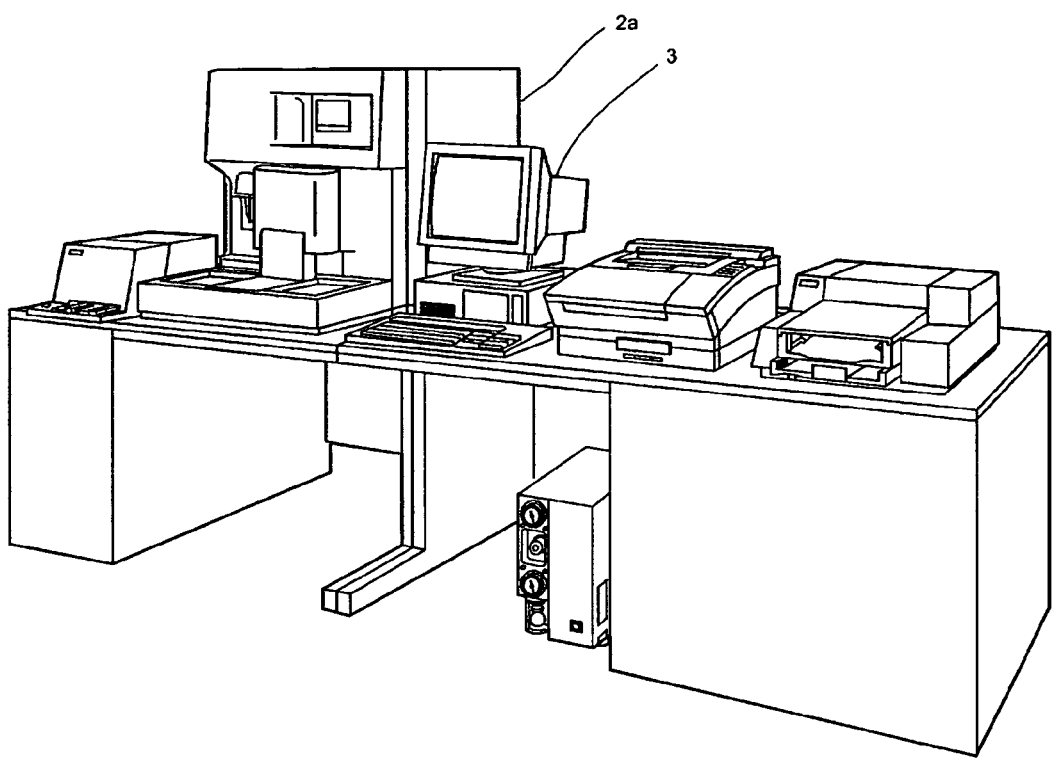
FIG. 2 is a perspective view showing the external structure of a hemocyte analyzer and data processing apparatus of the first embodiment.
Figure 3:
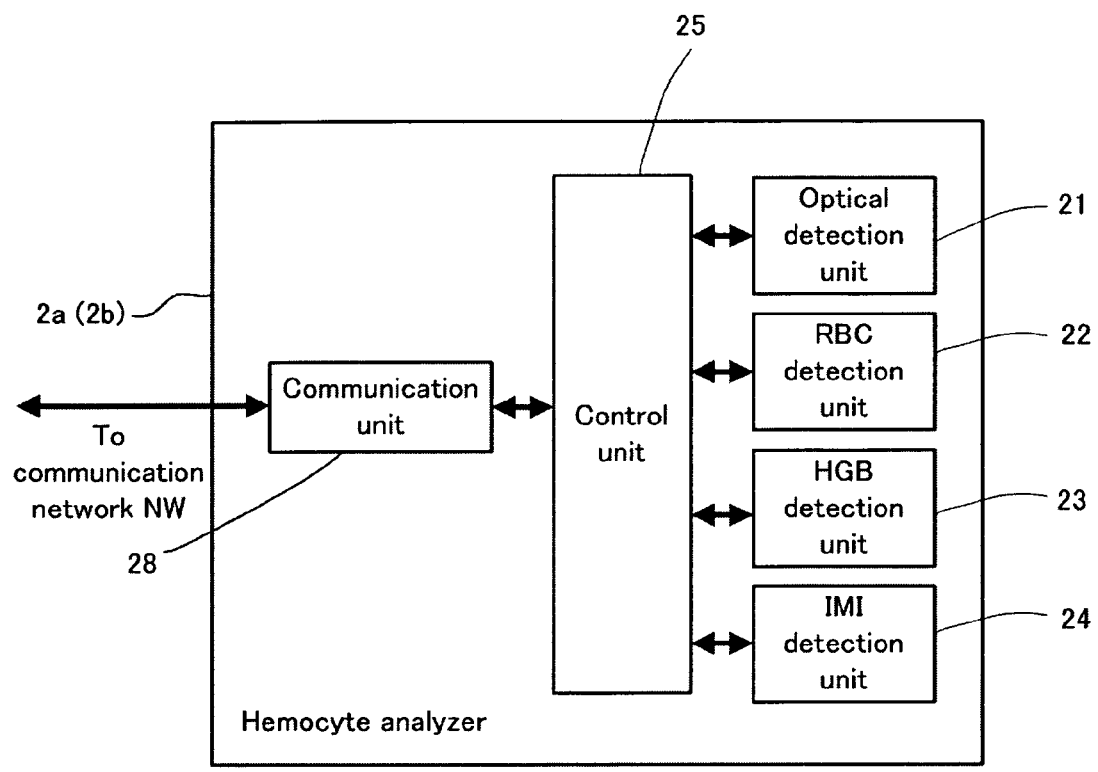
FIG. 3 is a block diagram showing the structure of the hemocyte analyzer of the first embodiment.

FIG. 2 is a perspective view showing the external structure of the hemocyte analyzer 2a and data processing apparatus 3. The hemocyte analyzers 2a and 2b are used for blood testings, and a constructed so as to be capable of predetermined measurements of components contained in blood specimens. Although only the hemocyte analyzer 2a is shown in FIG. 2, two hemocyte analyzers 2a and 2b having identical structures are connected so as to be capable of sending and received data to and from the data processing apparatus 3 in the analysis system 1 of the first embodiment. FIG. 3 is a block diagram showing the structure of the hemocyte analyzer 2a (2b). The hemocyte analyzer 2a (2b) is configured by the essential structural elements of an optical detection unit 21, RBC detection unit 22, HGB detection unit 23, IMI detection unit 24, control unit 25, and communication unit 28. The control unit 25 is configured by a CPU, ROM, RAM and the like, so as to control the operation of each structural element of the hemocyte analyzer 2a. The communication unit 28 is an interface, for example an Ethernet (registered trademark) interface, and is capable of sending and receiving data between the data processing apparatuses 3, 5, and 6.

Figure 4:
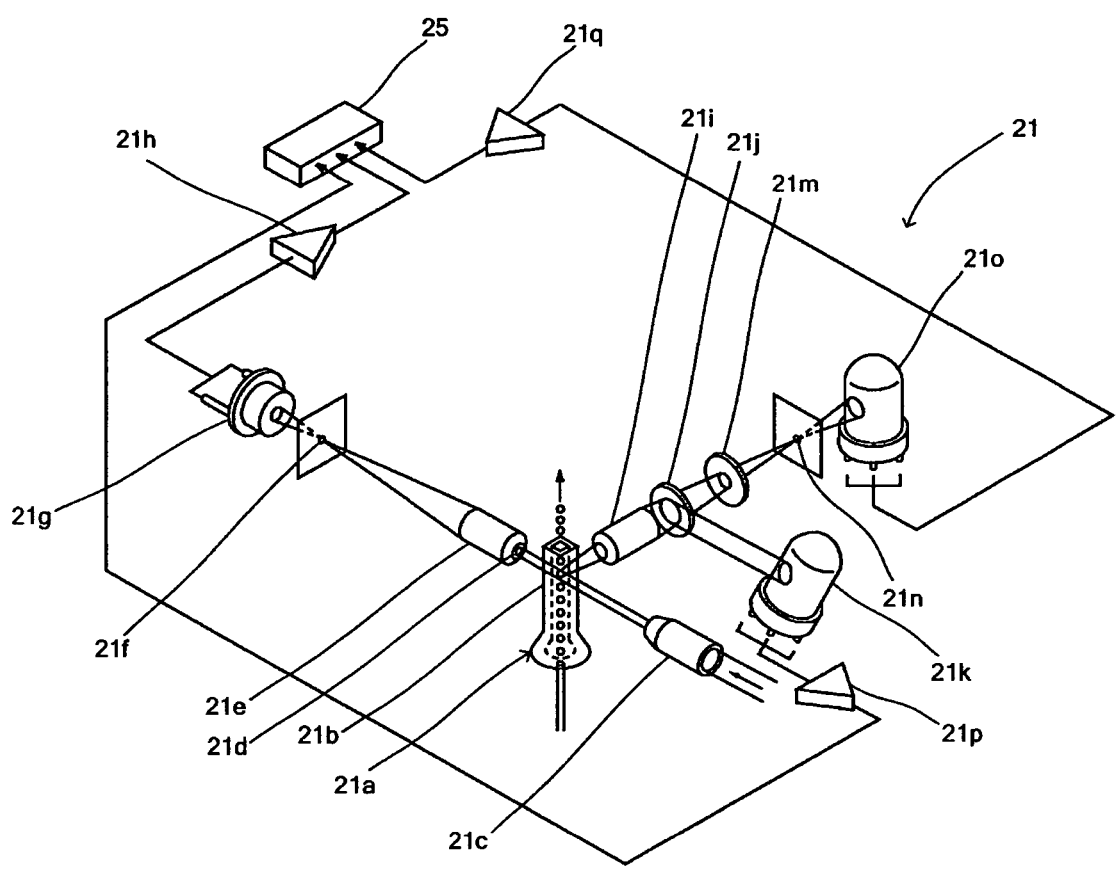
FIG. 4 is a schematic view showing the structure of the optical detection unit of the hemocyte analyzer of the first embodiment.

The optical detection unit 21 is capable of measuring white blood cells, nucleated red blood cells, and reticulocytes by flow cytometry using a semiconductor laser. FIG. 4 is a schematic view showing the structure of the optical detection unit 21. The hemocyte analyzer 2a has a sample supply part not shown in the drawing, and blood samples are suctioned and measured, diluted at a predetermined dilution ratio, and stained by the sample supply part. The optical detection unit 21 is provided with a sheath flow cell 21a, and a sample is supplied from the sample supply part to the sheath flow cell 21a. The optical detection unit 21 is also provided with a sheath fluid tank not shown in the drawing, and sheath fluid is supplied from the sheath fluid tank to the sheath flow cell 21a. The sample flows encapsulated in the sheath fluid within the sheath flow cell 21a. The sheath flow cell 21a is provided with an orifice 21b, and the orifice 21b constricts the flow of the sample, and the particles contained in the sample, such as white blood cells, red blood cells and the like, pass one by one through the orifice 21b.

A semiconductor laser light source is arranged in the optical detection unit 21 so as to emit laser light toward the orifice 21b of the sheath flow cell 21a. An illumination lens system 21c configured by a plurality of lenses is disposed between the semiconductor laser light source and the sheath flow cell 21a. Parallel beams emitted from the semiconductor laser light source are collected at a beam spot by the illumination lens system 21c. A forward scattered light collection lens 21e, which is provided with a beam stopper 21d, is disposed on the optical axis of the light emitted from the semiconductor laser light source so as to confront the illumination lens system 21c and sandwich the sheath flow cell 21a therebetween, such that the direct light from the semiconductor laser light source is blocked by the beam stopper 21d.

When a sample flows in the sheath flow cell 21a, optical signals are generated from the scattered light and fluorescent light. The forward signal light is collected by the forward scattered light collection lens 21e, and sent to a photoreceptor system in a later stage. This photoreceptor system is provided with a pinhole 21f, and a photodiode 21g downstream from the optical axis. After the stray light (light outside the measurement) is eliminated by the pinhole 21f, the signal light sent from the forward scattered light collection lens 21e is subjected to opto-electric conversion by the photodiode 21g, and the generated electric signal (forward scattered light signal) is amplified by an amplifier 21h and output to the control unit 25. The forward scattered light signal reflects the size of the hemocyte, such that the size of the hemocyte can be obtained when the control unit 25 subjects the forward scattered light signal to signal processing.

A lateral collection lens 21i is disposed at the side of the sheath flow cell 21a so as to face the optical axis connecting the illumination lens system 21c and the forward scattered light lens 21e, and the lateral light generated when the hemocyte passing through the sheath flow cell 21a is illuminated by the semiconductor laser is collected by the lateral collection lens 21i. A dichroic mirror 21j is provided on the downstream side of the lateral collection lens 21i, such that the signal light sent from the lateral collection lens 21i is divided into a scattered light component and a fluorescent light component by the dichroic mirror 21j. A photomultiplier tube 21k for receiving the lateral scattered light is provided on the side of the dichroic mirror 21j (the direction of the intersection of the optical axes connecting the lateral collection lens 21i and the dichroic mirror 21j), and an optical filter 21m, pinhole 21n, and photomultiplier tube 210 are provided on the downstream side of the optical axis of the dichroic mirror 21j. The lateral scattered light component separated by the dichroic mirror 21j is subjected to photoelectric conversion by the photomultiplier 21k, and the generated electrical signals (lateral scattered light signals) are amplified by the amplifier 21p and output to the control unit 25. The lateral scattered light signals reflect the internal information (size of nucleus and the like) of the hemocyte, and the control unit 25 obtains the size of the nucleus of the hemocyte by subjecting the lateral scattered light signal to signal processing. Furthermore, after the lateral fluorescent light component emitted from the dichroic mirror 21j has been subjected to wavelength selection by the optical filter 21m, the light is subjected to photoelectric conversion by the photomultiplier 21o, and the generated electrical signals (lateral fluorescent light signals) are amplified by the amplifier 21q and output to the control unit 25. The lateral fluorescent light signals reflect information relating to the degree of staining of the hemocyte.

Figure 5:
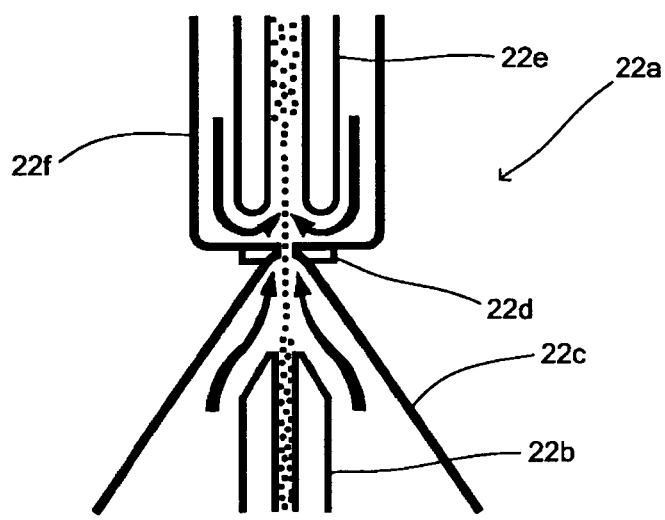
FIG. 5 is a schematic view showing the structure of the RBC detection unit of the hemocyte analyzer of the first embodiment.

The RBC detection unit 22 is capable of measuring the number of red blood cells and number of platelets by a sheath flow-DC method. FIG. 5 is a schematic view showing the structure of the RBC detection unit 22. The RBC detection unit 22 has a sheath flow cell 22a as shown in FIG. 5. The sheath flow cell 22a is provided with a sample nozzle 22b that opens facing upward. Furthermore, the sheath flow cell 22a has tapered chamber 22c that becomes narrower as it progresses upward, and the sample nozzle 22b is disposed in the center of the interior of the chamber 22c. The top end of the chamber 22c is provided with an aperture 22d, and the aperture 22d is positioned at the center position of the sample nozzle 22b. The sample supplied from the sample supply unit is transported upward from the end of the sample nozzle 22b, and a front sheath fluid is simultaneously supplied to the chamber 22c, such that the front sheath fluid flows upward to the aperture 22d. The sample flows encapsulated in the front sheath fluid, and the sample flow is narrowly constricted by the tapered chamber 22c, such that the hemocytes in the sample pass one by one through the aperture 22d. An electrode is provided in the aperture 22d, and a direct current is supplied to the electrode. The change in the direct current resistance in the aperture 22d is detected when the sample flows through the aperture 22d, and an electrical signal is output to the control unit 25. Since the direct current resistance increases when the hemocyte flows through the aperture 22d, the electrical signal reflects the hemocyte passage information at the aperture 22d, and the numbers of red blood cells and platelets can be counted by subjecting the electrical signal to signal processing.

A vertically extending collection tube 22e is provided above the aperture 22d. The collection tube 22e is arranged within a chamber 22f that is connected to the chamber 22c through the aperture 22d. The bottom end of the collection tube 22e is isolated from the interior wall of the chamber 22f. The chamber 22f supplies back sheath fluid, and the back sheath fluid flows downward through the outside region of the collection tube 22e of the chamber 22f. After reaching the bottom end of the chamber 22f, the back sheath fluid flowing outside the collection tube 22e passes between the bottom end of the collection tube 22e and the inner wall of the chamber 22f, and enters the interior of the collection tube 22e. Thus, the hemocytes that have passed through the chamber 22d are prevented from returning, thereby preventing hemocyte detection errors.

Figure 6:
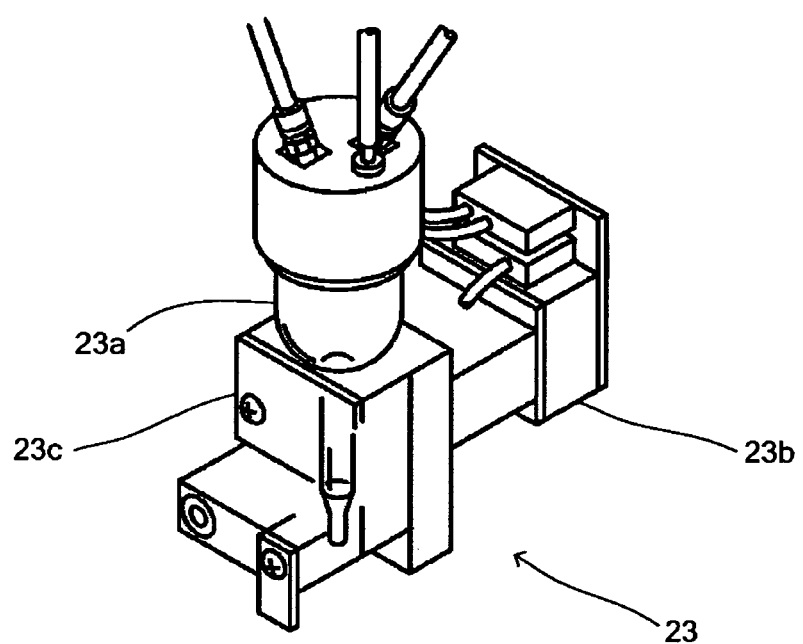
FIG. 6 is a perspective view showing the structure of a HGB detection unit of the hemocyte analyzer of the first embodiment.

The HGB detection unit 23 is capable of measuring the amount of hemoglobin (HGB) by the SLS hemoglobin method. FIG. 6 is a perspective view showing the structure of the HGB detection unit 23. The HGB detection unit 23 has a cell 23a for holding dilute sample, light-emitting diode 23b for emitting light toward the cell 23a, and a photoreceptor element 23c for receiving the light that passes through the cell 23a. In the sample supply unit, a measured amount of blood is diluted to a predetermined dilution by dilution fluid and a predetermined hemolytic agent to obtain a dilute sample. The hemolytic agent has the property of transforming hemoglobin in the blood to SLS-hemoglobin. The dilute sample is supplied from the sample supply unit to the cell 23a, and is accommodated in the cell 23a. In this state, the light-emitting diode 23b emits light, and the light passing through the cell 23a is received by the photoreceptor element 23c disposed opposite the light-emitting diode 23b. The light-emitting diode 23b emits light of a wavelength that has a high absorption rate by the SLS-hemoglobin, and since the cell 23a is configured by a plastic material that has a high degree of light transmittancy, the photoreceptor element 23c only receives the transmission light absorbed by the dilute sample from the emission light of the light-emitting diode 23b. The photoreceptor element 23c outputs an electrical signal that corresponds to the amount of received light (optical density) to the control unit 25, and the control unit 25 compares this optical density with the optical density of the previously measured dilution fluid, then calculates the hemoglobin value.

Figure 7:
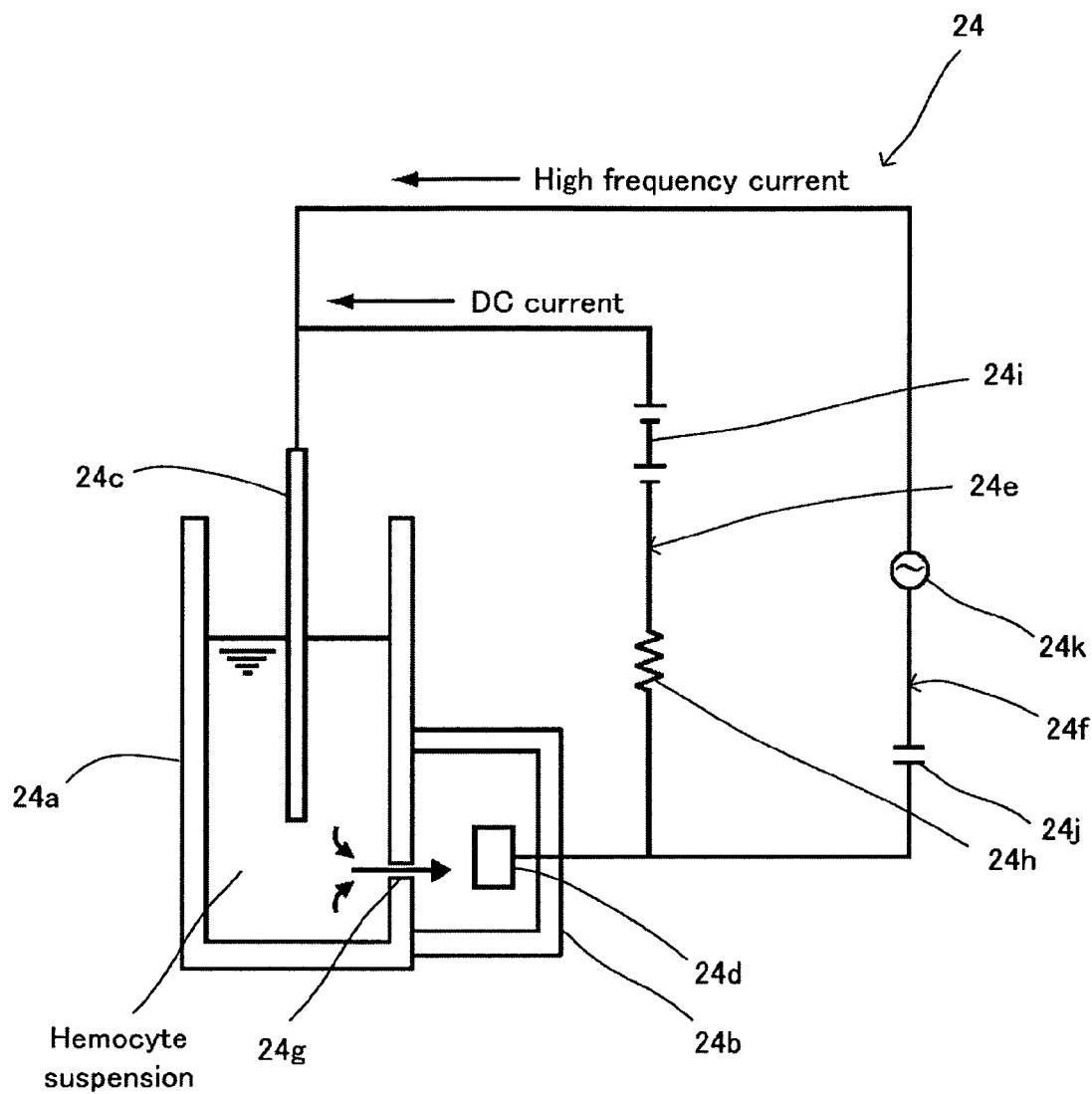
FIG. 7 is a schematic view showing the structure of the IMI detection unit of the hemocyte analyzer of the first embodiment.

The IMI detection unit 24 is capable of measuring the incidence of immature red cells in a specimen by the RF/DC detection method. FIG. 7 is a schematic view showing the structure of the IMI detection unit 24. The IMI detection unit 24 has a detection chamber 24a, suction chamber 24b, DC current supply circuit 24e connected to electrodes 24c and 24d, and a high-frequency current supply circuit 24f connected to electrodes 24c and 24d. A blood sample suctioned and measured, and diluted to a predetermined dilution by the sample supply unit is delivered to the detection chamber 24a. The detection chamber 24a and the suction chamber 24b are adjacent, and both chambers 24a and 24b are connected by an aperture 24g. The suction chamber 24b is connected to a pump not shown in the drawing, such that the dilute sample can be suctioned by the pump. The suctioned dilute sample passes from the detection chamber 24a through the aperture 24g and into the suction chamber 24b. The electrode 23c is provided within the detection chamber 24a, and the electrode 24d is provided within the suction chamber 24b. The DC current supply circuit 24e is connected in series with a resistor 24h and a DC power supply 24i, such that a DC current flows between the electrodes 24c and 24d. Accordingly, when a dilute sample is suctioned by the pump, the DC resistance changes between the electrodes 24c and 24d when the hemocytes in the dilute sample pass through the aperture 24g. An electrical signal representing the change in the DC resistance is output from the DC current supply circuit 24e to the control unit 25. The change in the DC resistance reflects the size information of the hemocyte that has passed through the aperture 24g, and the size of the hemocyte is obtained when the control unit 25 subjects the electrical signal to signal processing.

The high-frequency current supply circuit 24f is connected in series with a capacitor 24j and a high-frequency power supply 24k, and supplies a high-frequency current between the electrodes 24c and 24d. Accordingly, when a dilute sample is suctioned by the pump, the high-frequency resistance changes between the electrodes 24c and 24d when the hemocytes in the dilute sample pass through the aperture 24g. An electrical signal representing the change in the high-frequency resistance is output from the high-frequency current supply circuit 24f to the control unit 25. The change in the high-frequency resistance reflects the internal density information of the hemocyte that has passed through the aperture 24g, and the internal density of the hemocyte is obtained when the control unit 25 subjects the electrical signal to signal processing.

Figure 8:
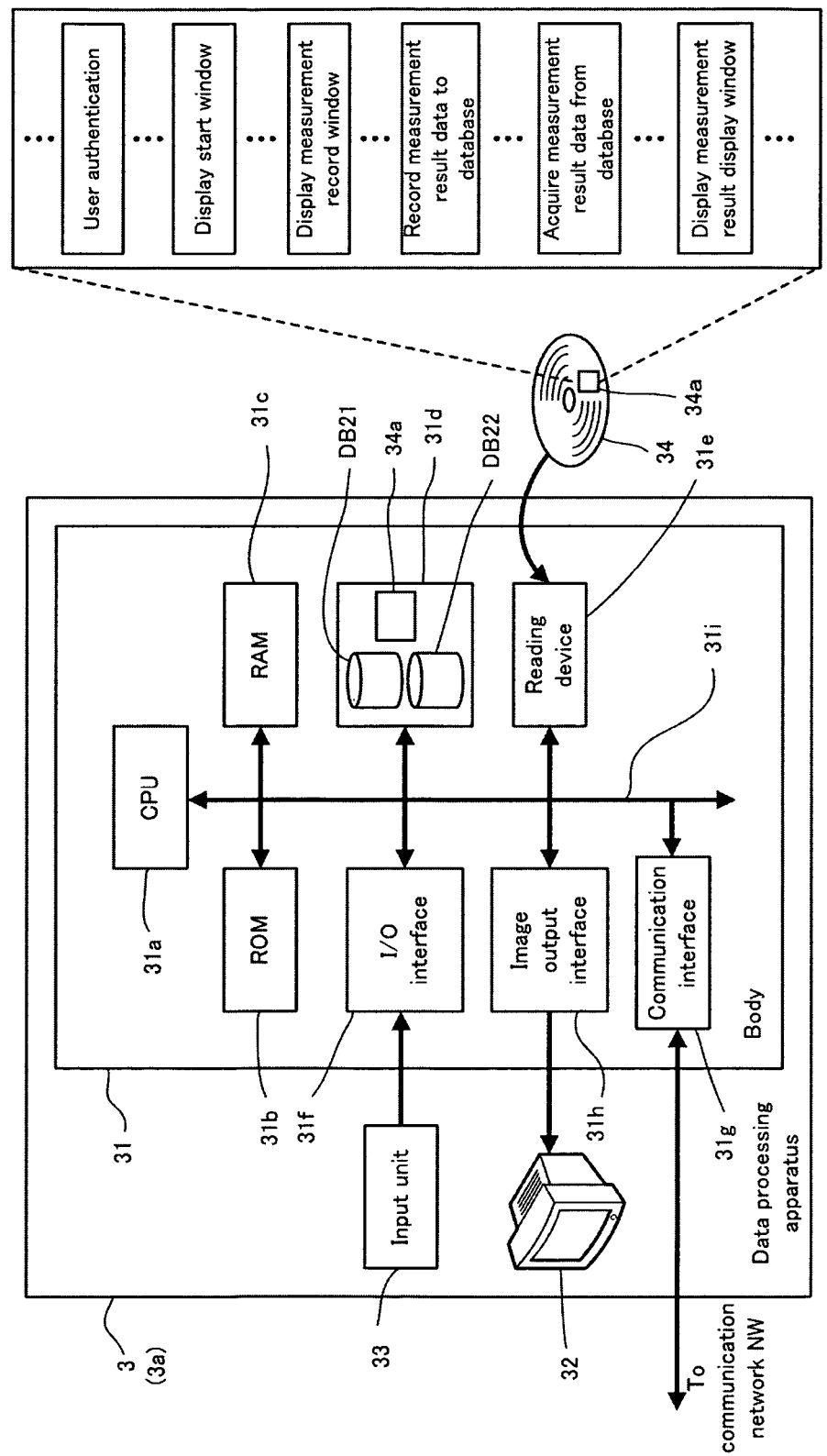
FIG. 8 is a block diagram showing the structure of the data processing apparatus of the hemocyte analyzer of the first embodiment.

The structure of the data processing apparatus is described below. FIG. 8 is a block diagram showing the structure of the data processing apparatus 3 used by the hemocyte analyzers 2a and 2b in the first embodiment. The data processing apparatus 3 is mainly configured by a computer 3a which includes a body 31, display unit 32, and input unit 33. The body 31 mainly includes a CPU 31a, ROM 31b, RAM 31c, hard disk 31d, reading device 31e, I/O interface 31f, communication interface 31g, and image output interface 31h, and the CPU 31a, ROM 31b, RAM 31c, hard disk 31d, reading device 31e, I/O interface 31f, communication interface 31g, and image output interface 31h are connected by a bus 31i.

The CPU 31a is capable of executing computer programs stored in the ROM 31b and computer programs loaded in the RAM 31c. The computer 3a functions as the data processing apparatus 3 when the CPU 31a executes an application program 34a described later.

The ROM 31b may be a mask ROM, PROM, EPROM, EEPROM or the like, and stores computer programs executed by the CPU 31a, and data used by the computer programs.

The RAM 31c may be an SRAM or DRAM or the like. The RAM 31c reads the computer programs stored in the ROM 31b and on the hard disk 31d. When the computer programs are being executed, the RAM 31c is used as a work area for the CPU 31a.

The hard disk 31d has installed thereon an operating system and application programs and the like, computer programs of various types which are executed by the CPU 31a, and data used in the execution of the computer programs. The application program 34a, which is described later, is also installed on the hard disk 31d.

The reading device 31e is configured by a floppy disk drive, CD-ROM drive, DVD-ROM drive or the like, and is capable of reading computer programs and data recorded on a portable storage medium 34. The portable recording medium 34 stores the application program 34a which allows a computer to function as a data processing apparatus for a measuring apparatus; the computer 3a can read the application program from the portable recording medium 34, and install the application program 34a on the hard disk 31d.

The application program 34a need not be provided by the portable recording medium 34, inasmuch as the application program 34a may be provided over an electrical communication line from an external apparatus connected to the computer 3a so as to be capable of communication by means of an electrical communication line (wired or wireless). For example, the application program 34a may be stored on the hard disk of a server computer connected to the Internet, such that the computer 3a can access the server computer and download the application program 34a and install the application program on the hard disk 31d.

An operating system that provides a graphical user interface environment, such as Windows (trademark of Microsoft Corporation) or the like, is installed on the hard disk 31d. In the following description, the application program 34a of the first embodiment operates on the aforesaid operating system.

Figure 9:
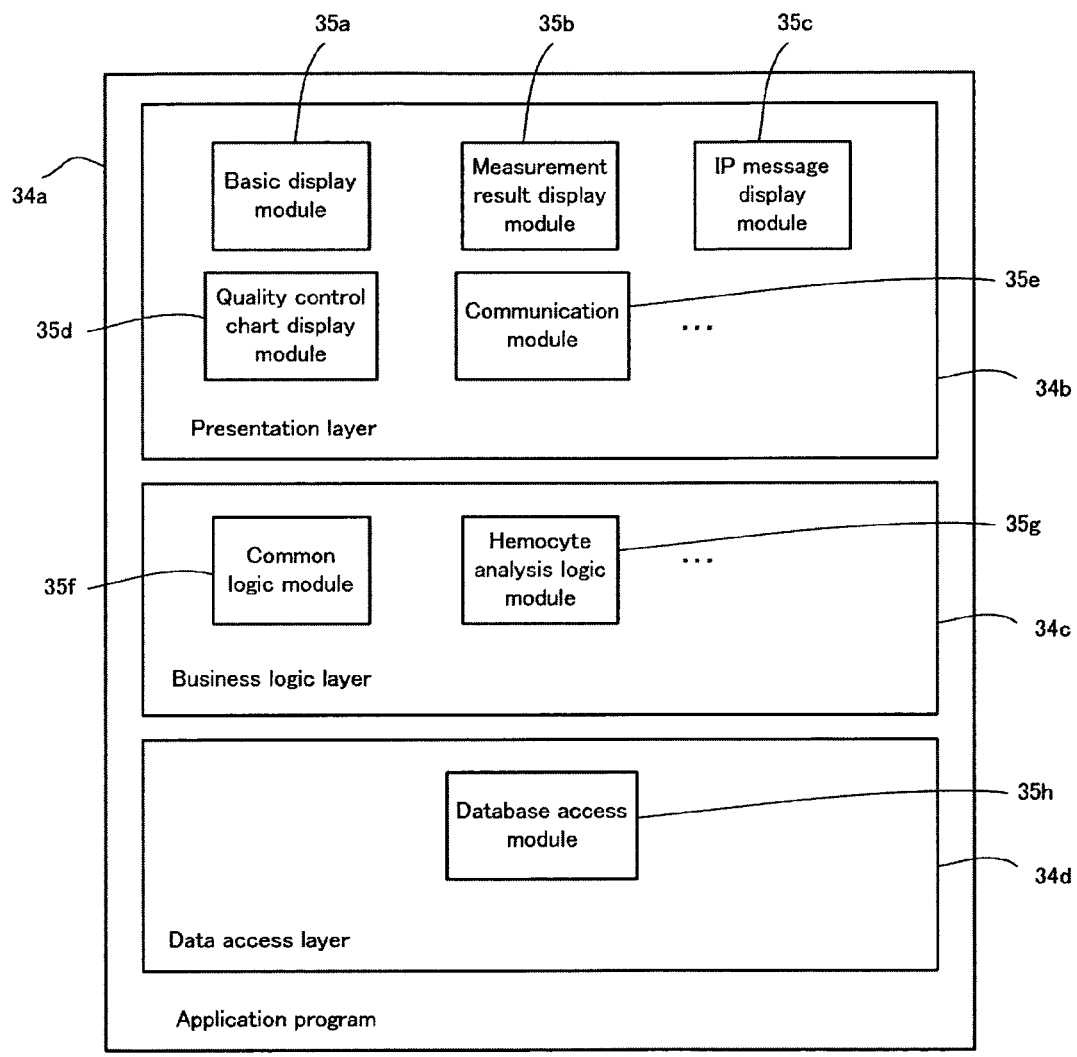
FIG. 9 is a schematic view showing the structure of the application program used by the hemocyte analyzer of the first embodiment.

FIG. 9 is a schematic view showing the structure of the application program 34a used by the blood analyzers 2a and 2b of the first embodiment. The application program 34a has a tri-layered architecture including a presentation layer 34b, business logic layer 34c, and data access layer 34d. The presentation layer 34b is layer equivalent to a user interface part and communication part in the application program 34a; a basic display module 35a for executing a basic parts display in a window of the application program 34a, a measurement result display module 35b for displaying measurement results of the hemocyte analyzers 2a and 2b on the display unit 32, an IP message display module 35c for displaying an IP message indicating an abnormal specimen or suspected anomaly, a quality control chart display module 35d for displaying a quality control screen, and a communication module 35e for communicating with the hemocyte analyzers 2a and 2b and the like belong to the presentation layer 34b.

The business logic layer 34c is a layer equivalent to data processing and operation part in the application program 34a; a common logic module 35f that is common to all apparatus models and includes a unit conversion module for data unit conversion, and a quality control graph display data preparation module and the like, and a hemocyte analysis logic module 35g for executing data processing characteristic of the hemocyte analyzers and the like belong to the business logic layer 34c.

The data access layer 34d is a layer equivalent to the data access part in the application program 34a; a database access module 35h for accessing databases DB21 and DB22, which are described later, belongs to the data access layer 35h. The program modules 35a-35h are components of the application program, and are included in the execution format file and dynamic link library. Although only the program modules 35a-35h are listed as program modules that configure the application program 34a, only these representative program modules are represented to simplify the description, and other program modules are actually present.

Figure 10:
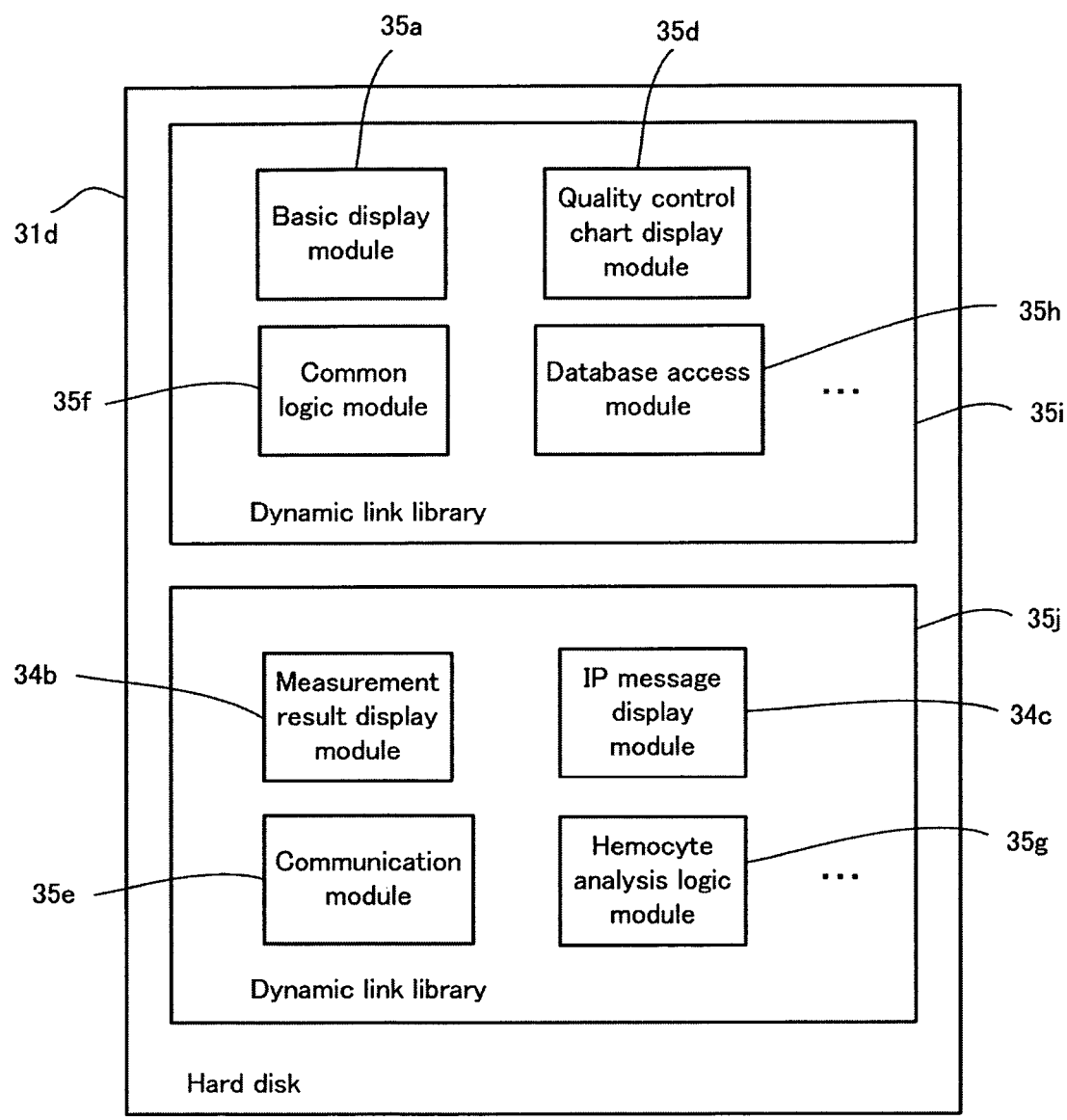
FIG. 10 is a schematic view showing the common module and model dependent module of the application program stored on the hard disk in the first embodiment.

The basic display module 35a, quality control chart display module 35d, common logic module 35f, and database access module 35h are common program modules of the application program of the blood coagulation measuring apparatuses (hereinafter referred to as 'common modules'), whereas the measurement result display module 35b, IP message display module 35c, communication module 35e, and hemocyte analysis logic module 35g are program modules that are characteristic of the application program for the hemocyte analyzers (hereinafter referred to as 'model-dependent modules'). FIG. 10 is a schematic view showing the storage condition of the common modules and model-dependent modules on the hard disk 31d. As shown in FIG. 10, the basic display module 35a, quality control chart display module 35d, common logic module 35f, and database access module 35h are stored in a single dynamic link library 35i. The measurement result display module 35b, IP message display module 35c, communication module 35e, and hemocyte analysis logic module 35g are also stored in a single dynamic logic library 35j. That is, the common modules and model-dependent modules are stored in separate dynamic link libraries 35i and 35j, and the dynamic link libraries 35i and 35j are saved on the hard disk 31d. Since the dynamic link libraries 35i and 35j are stored in separate files (dynamic link libraries), the common module can be used in other application programs directly in the dynamic link library format of binary data without processing the links, thus improving convenience and development efficiency. Although the common modules are stored in a single dynamic link library 35i as described in the present embodiment, the common modules may also be separately stored in a plurality of dynamic link libraries. Similarly, although the model-dependent modules are stored in a single dynamic link library as described in the present embodiment, the model-dependent modules may also be separately stored in a plurality of dynamic link libraries.

The previously described application program 34a is configured in three layers including a presentation layer 34b, business logic layer 34c, and data access layer 34d. The presentation layer 34b includes many program modules for many different measuring apparatuses. The business logic layer 34c includes many program modules that are common for different measuring apparatuses that use identical measurement principles (for example, high-order models and low-order models of hemocyte analyzers), and cannot be used commonly among measuring apparatuses that use different measurement principles (for example, hemocyte analyzers and blood coagulation measuring apparatuses). And the data access layer 34d includes many program modules common among diverse types of measuring apparatuses. In this way this hierarchy can be understood according to the level of commonality of the parts of the application program, and since the program modules are divided by the commonality level, program modules can be effectively used among diverse apparatuses, thus providing greater efficiency in developing application programs for diverse equipment.

Databases DB21 and DB22 are installed on the hard disk 31d. The database DB21 is a relational database for mutually associating and storing specimen numbers and measurement result data of the hemocyte analyzers 2a and 2b. The measurement result data acquired by the measurements performed by the hemocyte analyzers 2a and 2b are stored in the database DB21 by the application program 34a. The application program 34a can also access the database DB21, read past measurement result data, and display the data on the display unit 32.

The database DB22 is a database for storing the setting values of the application program 34a and the hemocyte analyzers 2a and 2b. The database DB22 is a relational database for mutually associating and storing setting data of various types. The application program 34a is software of the multi user type intended to be used by a plurality of users; usage restrictions of the functions of the application program 34a can be set for each user, and the display format can be set differently for each user. Accordingly, the setting values and the like of each user are saved in the database DB22, and the application program 34a reads the setting data from the database DB22 at startup to realize the operation pursuant with the settings of each user.

Figure 11:
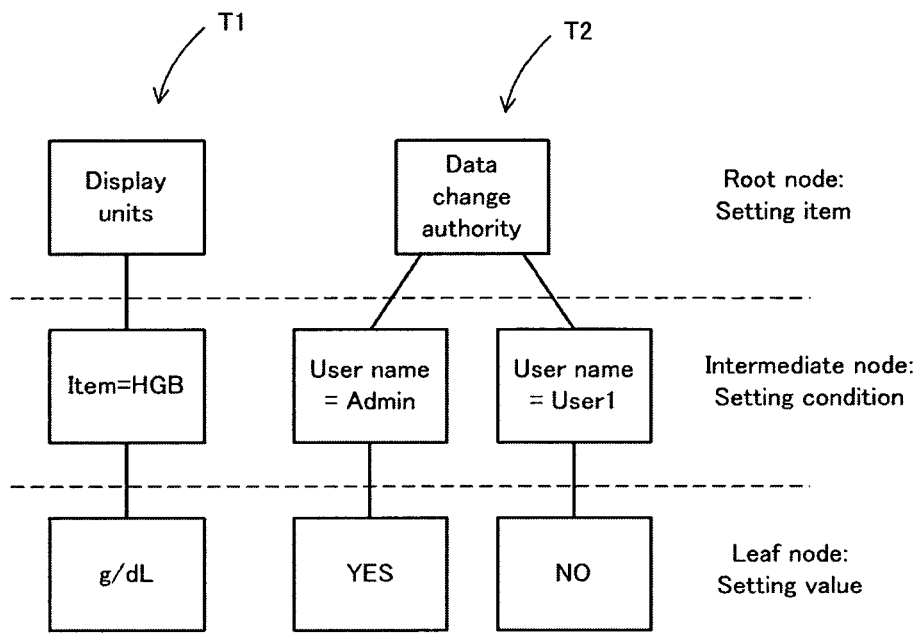
FIG. 11 is a conceptual drawing showing an example of a data tree for setting the measuring apparatus and application program of the first embodiment.
Figure 12:
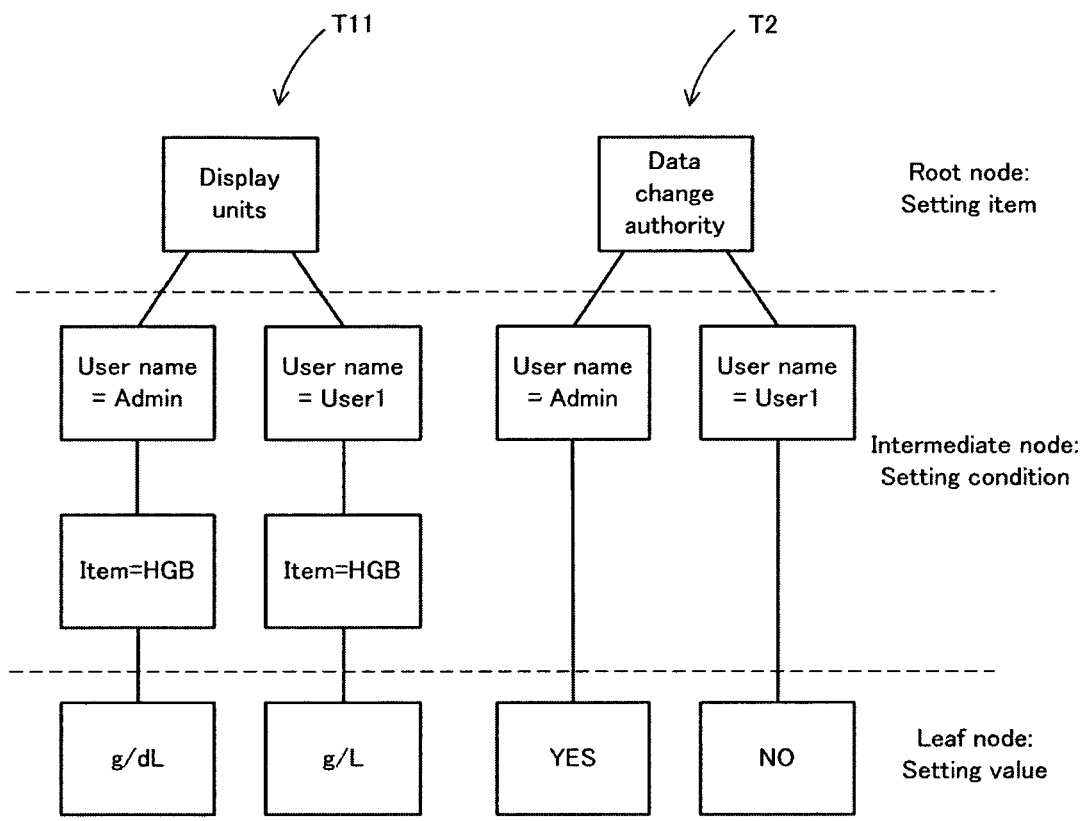
FIG. 12 is a conceptual drawing showing an example of a data tree when functions are added to the application program of the first embodiment.

The application program 34a reads the setting data from the database DB22 at startup, and configures a data tree T with these setting data. FIGS. 11 and 12 are conceptual drawings showing examples of the data tree T. The database DB22 stores the setting data of the application program 34a and the hemocyte analyzers 2a and 2b; the database DB22 is accessed from the application program 34a to read the setting data and refresh the setting data. For example, the setting content of [display units of item HGB are g/dL] are a data set (setting data) including a first data "item=HGB" representing a setting condition, and a second data "display units=g/dL" mutually associating the setting item and setting value. The setting content of [user name "Admin" has data modification authority] is a data set including a first data "username=Admin" representing a setting condition, and a second data "data modification authority=YES" mutually associating the setting item and setting value; the setting content [user name "User1" does not have data modification authority] is a data set including a first data "user name=User1" and a second data "data modification authority=NO." Various data sets include a plurality of data (first data, second data), and each data that are included in one data set are mutually associated and stored in the database DB22.

Figure 13:
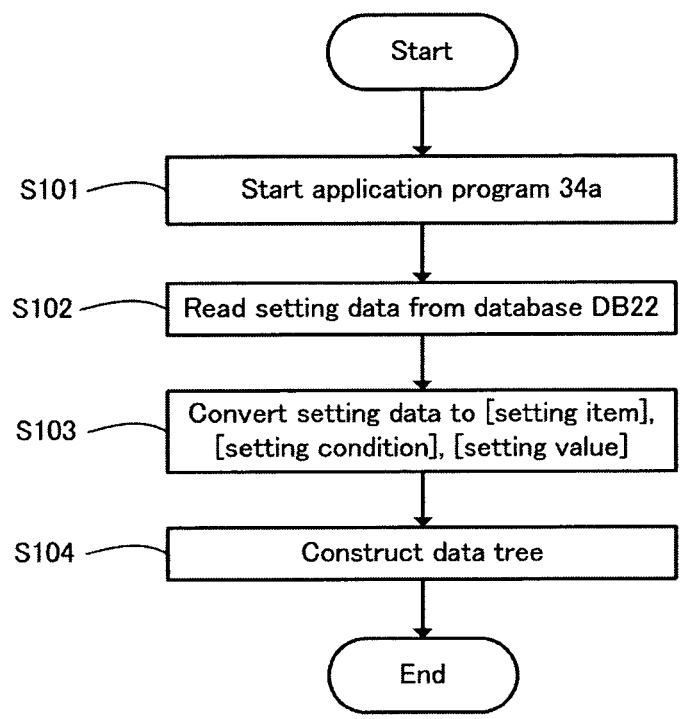
FIG. 13 is a flow chart showing the flow of the application program setting operation of the first embodiment.

The operation of the application program 34a using the database DB22 is described below. FIG. 13 is a flow chart showing the flow of the setting operation performed by the application program 34a. When an instruction to start the operation of the application program 34a is input to the data processing apparatus 3 as when a user double clicks the mouse on an icon displayed on the screen of the image display device 32 of the data processing apparatus 3, the CPU 31a receives the operation start instruction and starts the application program 34a (step S101). Then, the CPU 31a reads the setting data (data sets) from the database DB22 (step S102), and processes the setting data (step S103). As described previously, each setting data include a first data representing the setting condition, and a second data mutually associating the setting data and setting values. In the process of step S103, a process is performed to disassemble the data set into [setting item], [setting condition], and [setting value]. That is, the data set "item=HGB" and "display units=g/dl is processed with the data 'display units' as [setting item], data 'item=HGB' as [setting condition], and data 'g/dL' as [setting value]. Similarly, the data set "user name=Admin" and "data modification authority=YES" is processed with the data 'data modification authority' as [setting item], data 'user name=Admin' as [setting condition], and data 'YES' as [setting value]; the data set "user name=User1" and "data modification authority=NO" is processed with the data 'data modification authority' as [setting item], data 'user name=User1' as [setting condition], and data 'NO' as [setting value]. The processed data are set in a hash table in the RAM 31c by the CPU 31a (step S104), thus constructing the data trees T1 and T2 shown in FIG. 11. The database access module 35h of the application program 34a accesses the data trees T1 and T2, sequentially searching, for example, "display units," "item=HGB," "g/dL," and when the [setting item] is "display units," the setting data "g/dL" of [setting condition] "item=HGB" is retrieved. Thus, the setting operation of the application program 34a is completed.

Changing specifications of the application program 34a to set [item display units modifiable by each user] is described from the example of FIG. 11. For example, when changing the setting content of [Display units of display item "HGB" in User name "Admin" are g/dL] from the above example, the pertinent data set includes "Username=Admin" and "Item=HGB" as first data representing the setting conditions, and "Display units=g/dL" as the second data mutually associating the setting item and the setting value; and when changing the setting content of [Display units of display item "HGB" in User name "User1" are g/dL] the pertinent data set includes "Username=User1" and "Item=HGB" as the first data, and "display units=g/dL" as the second data. Then, when the application program 34a starts, The data set "Username=Admin", "Item=HGB", and "Display units=g/dL" are processed with "Display unit" as the [setting item] data, "Username=Admin" as the [setting condition] data, and "g/dL" as the [setting value] data. Similarly, the data set of "Username=User1", "Item=HGB", and "Display units=g/dl" is processed with "Display units" as the [Setting item] data, "Username=User1" and ""Item=HGB" as the [Setting condition] data, and "g/dL" as the [Setting value] data. The processed data are set in a hash table, thus constructing the data trees T1 and T2 shown in FIG. 12. Since this develops the setting data into a tree in which the root node is set for [Setting item], intermediate node is set for [Setting condition], and leaf node is set for [Setting value], data tree structures independent for each [Setting item] are constructed. For example, the data tree T1 in which [Setting item] is "Display units" and data tree T2 in which [Setting item] is "Data modification authority" are constructed separately. Therefore, when changing the setting specifications of "Display units" in the application program 34a, the data tree T1 in which the [Setting item] is "Display units" is changed to data tree T11, and the change does not affect the data tree T2 of "Data modification authority" (refer to FIG. 12). Accordingly, part of a setting specification is changed in a version upgrade of the application program 34a, only the part relating to the modified data tree is changed in the application program 34a, thereby reducing the number of development processes. Moreover, since the modified data tree T11 does not change the structure of the data tree itself, the database access module 35h is not modified and is accessible from the application program 34a. Therefore, even when the specification of the setting value is modified, there are minimal changes to the application program 34a, thus improving convenience and development efficiency.

The I/O interface 31f is configured by, for example, a serial interface such as USB, IEEE394, RS-232C or the like, parallel interface such as SCSI, IDE, IEEE284 or the like, and analog interface such as D/A converter, A/D converter or the like. The I/O interface 35f is connected to the input unit 33 including a mouse and keyboard, such that data can be input to the computer 3a when a user uses the input unit 33.

The communication unit 31g is an interface, for example an Ethernet (registered trademark) interface, and the data processing apparatus 3 is capable of sending and receiving data between the hemocyte analyzers 2a and 2b, blood coagulation measuring apparatuses 4a and 4b, data processing apparatuses 5 and 6, and database server 7 connected to a communication network NW using a predetermined communication protocol by means of this communication interface 31g.

The image output interface 35h is connected to the display unit 32 configured by an LCD, CRT or the like, and image signals corresponding to image data received from the CPU 31a are output to the display unit 32. The display unit 32 displays images (screens) in accordance with the input image signals.

Figure 14:
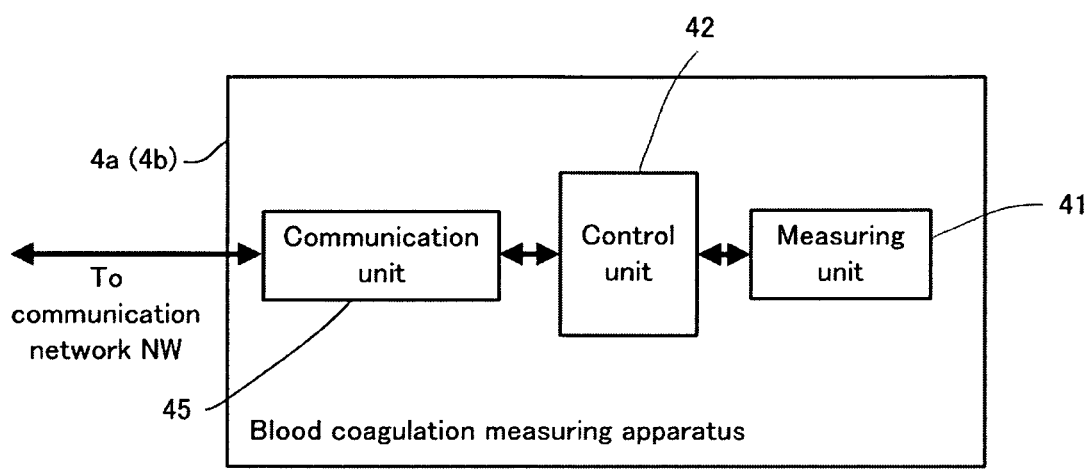
FIG. 14 is a block diagram showing the structure of the blood coagulation measuring apparatus of the first embodiment.

The structure of the blood coagulation measuring apparatuses 4a and 4b are described below. FIG. 14 is a block diagram showing the structure of the blood coagulation measuring apparatus 4a (4b). The blood coagulation measuring apparatus 4a (4b) is configured by essential components of a measuring unit 41, control unit 42, and communication unit 45. The control unit 42 has a CPU, ROM, RAM and the like, and controls the operation of the various structural elements of the blood coagulation measuring apparatus 4a. The communication unit 45 is an interface, for example an Ethernet (registered trademark) interface, and is capable of sending and receiving data between the data processing apparatuses 3, 5, and 6.

The measuring unit 41 has a light-emitting diode 41a, halogen lamp 41b, optical filter 41c, optical fiber 41d, photodiodes 41e and 41f (refer to FIGS. 15 and 16), and a heater not shown in the drawing. The measuring unit 41 is capable of measuring blood coagulation time using a biological activity method; and measuring the change in optical density when specific reagents and coloring synthetic substrate are added to the plasma, and measuring the change in optical density when stabilizing reagent and antibody-sensitive reagent are added to plasma or serum.

Figure 15:
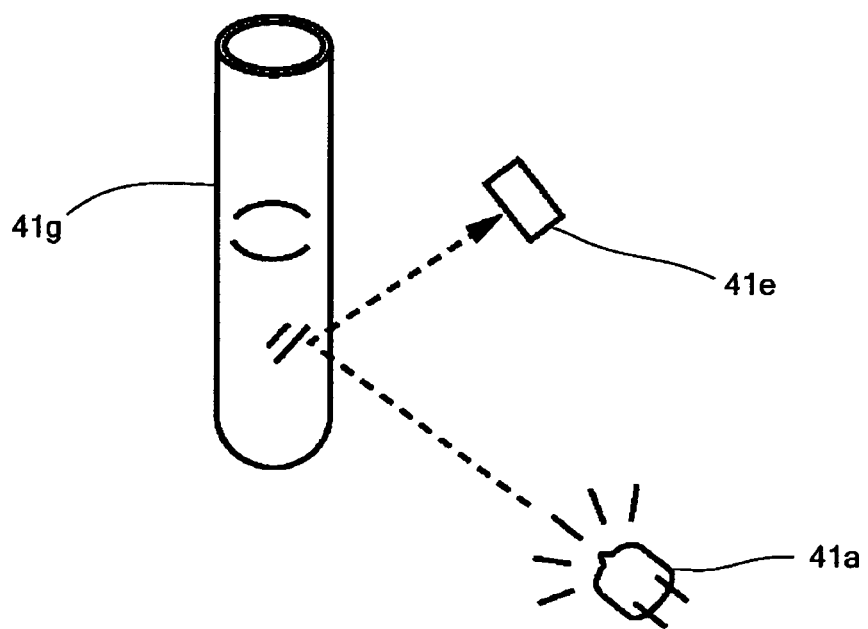
FIG. 15 is a schematic view illustrating the measurement principle of the biological activity method in the blood coagulation measurement.

FIG. 15 is a schematic view illustrating the measurement principle of the biological activity method. As shown in FIG. 15, the light-emitting diode 41a is disposed in the measuring unit 41 so as to emit light toward a cavity 41g that contains a sample. At the side of the cavity 41g, the photodiode 41e is disposed such that the light-receiving surface is facing toward the cavity 41g, and the direction of the light-receiving optical axis of the photodiode 41e forms an approximate 90 (angle in the horizontal direction relative to the light-emitting optical axis of the light-emitting diode 41a. The light-emitting diode 41a emits light at a wavelength of approximately 660 nm. A measured amount of plasma is accommodated in the cavity 41g, and a coagulation reagent is added after the plasma has been heated by the heater for a predetermined time. Thereafter, light from the light-emitting diode 41a irradiates the sample, and the scattered light for the sample is received by the photodiode 41e. The amount of received light represents the turbidity of the sample, and although the sample has weak scattered light (low turbidity) immediately after the reagent is added such that there is scant change in the amount of received light, fibrin clots begin to form in the sample as the reaction progresses, and the scattered light rapidly increases in conjunction with the increasing opacity of the sample in conjunction with the reaction. When the coagulation reaction ends, there is no further increase in scattered light, and the received light level remains fixed. The photodiode 41e outputs an electrical signal corresponding to the amount of received light, and this electrical signal is sent to the control unit 42. The control unit 42 calculates the coagulation time from the received light data, and calculates the active percentage or density of specific blood components from the coagulation time.

Figure 16:
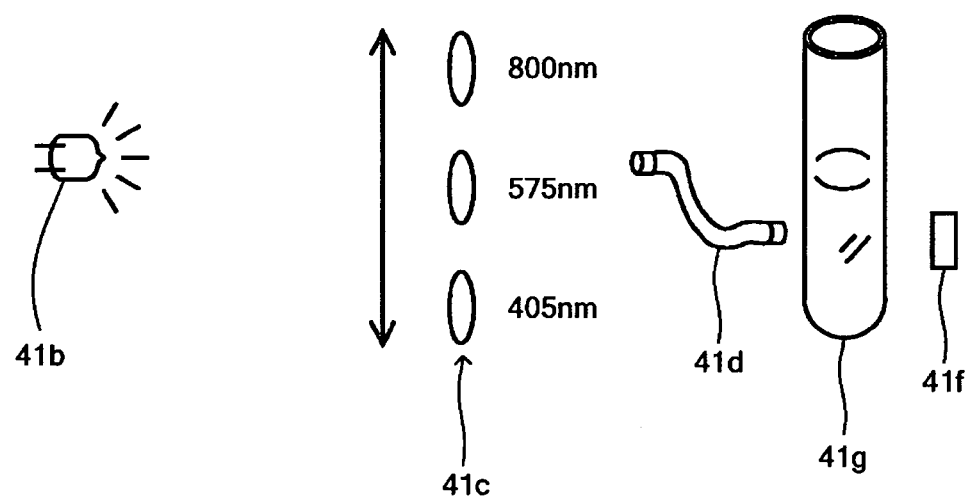
FIG. 16 is a schematic view illustrating the measurement principle of the synthetic substrate method and immunoturbidity method in the blood coagulation measurement.

FIG. 16 is a schematic view illustrating the measurement principle of the synthetic substrate method and immunoturbidity method. As shown in FIG. 16, a halogen lamp 41b is arranged in the measuring unit 41 so as to emit light toward the cavity 41g. The optical filter 41c and optical fiber 41d are disposed between the halogen lamp 41b and the cavity 41g, such that the light emitted from the halogen lamp 41b was diffracted into three wavelengths of 800 nm, 575 nm, and 405 nm by the optical filter 41c, and this diffracted light passes through the optical finer 41d to irradiate the sample. The photodiode 41f is disposed so as to face the cavity 41g, such that the light transmitted through the sample arrives at the photodiode 41f and the received light is converted to an electrical signal by the photodiode 41f and output to the control unit 42. The control unit 42 calculates the change in optical density from the received light data, and calculates the active percentage or density of specific blood components based on a calibration curve representing the relationship of the active percentage or density of the specific blood component and the change in optical density or the change in optical density. When ATIII (antithrombin III), (2PI ((2-antiplasmin) or the like is measured by the synthetic substrate method, the plasma is heated for a predetermined time by the heater, and thereafter the coloring synthetic substrate is added and irradiated by light having a wavelength of 405 nm, whereupon the change in optical density is measured. Furthermore, when FDP (fibrin decomposition product), D-D dimer or the like is measured using the immunoturbidity method, the sample (plasma or serum) is heated for a predetermined time by the heater, and thereafter a stabilizing reagent and antibody sensitive reagent are added, and the sample is irradiated by light having a wavelength of 575 nm or 800 nm, whereupon the change in optical density is measured.

Figure 17:
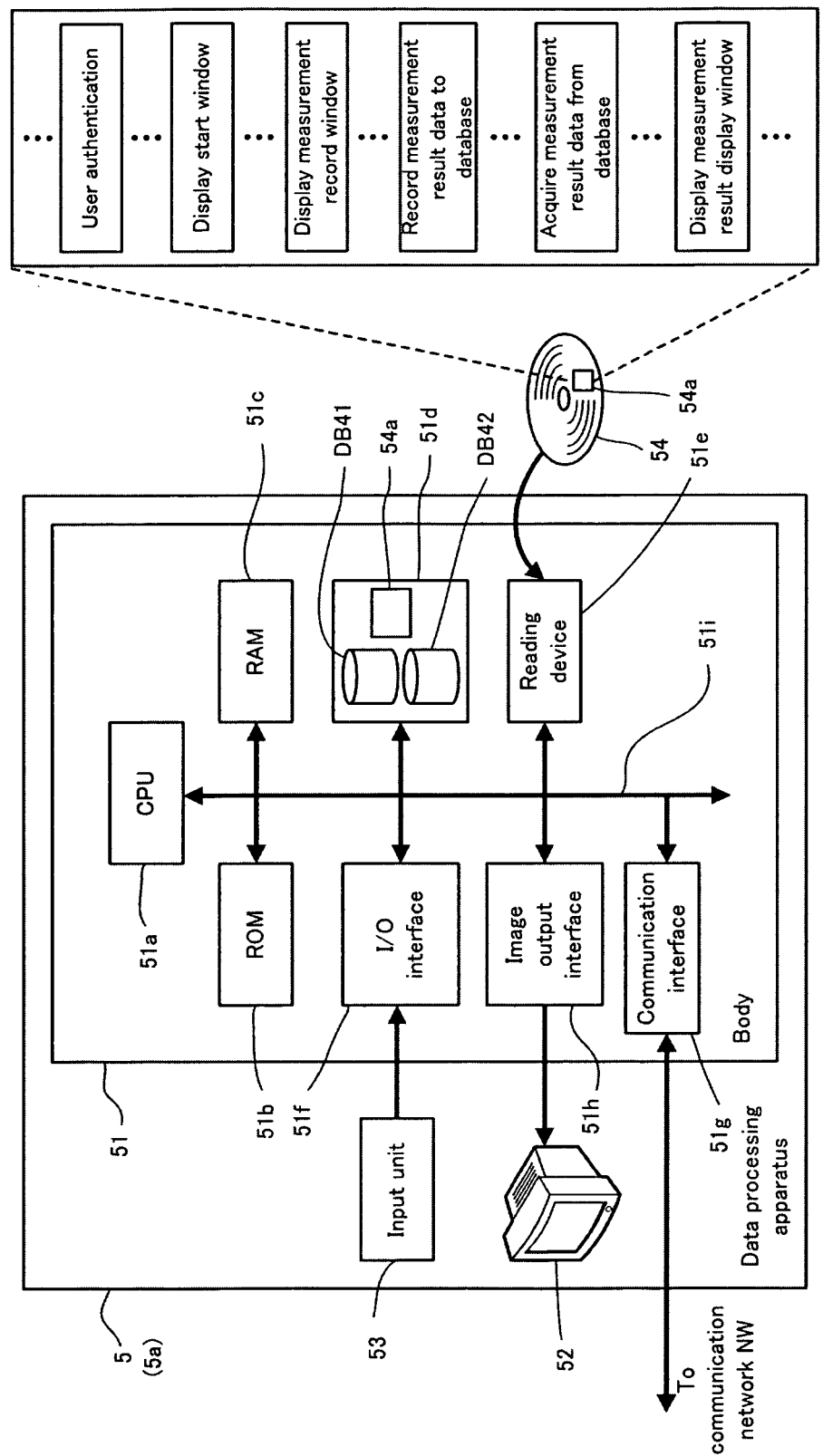
FIG. 17 is a block diagram showing the structure of the data processing apparatus of the blood coagulation measuring apparatus of the first embodiment.

The structure of the data processing apparatus 5 is described below. FIG. 17 is a block diagram showing the structure of the data processing apparatus 5 of the blood coagulation measuring apparatus 4a and 4b of the first embodiment. As shown in FIG. 17, the data processing apparatus 5 is mainly configured by a computer 5a having a body 51, display unit 52, input unit 53. The body 51 is mainly configured by a CPU 51a, ROM 51b, RAM 51c, hard disk 51d, reading device 51e, I/O interface 51f, communication interface 51g, and image output interface 51h; the CPU 51a, ROM 51b, RAM 51c, hard disk 51d, reading device 51e, I/O interface 51f, communication interface 51g, and image output interface 51h are connected by a bus 51i. The structures of the CPU 51a, ROM 51b, RAM 51c, hard disk 51d, reading device 51e, I/O interface 51f, communication interface 51g, and image output interface 51h are identical to the structures of the CPU 31a, ROM 31b, RAM 31c, hard disk 31d, reading device 31e, I/O interface 31f, communication interface 31g, and image output interface 31h, and are therefore omitted from the description.

The portable recording medium 54, which is readable by the reading device 51e, stores the application program 54a which allows a computer to function as a data processing apparatus for a measuring apparatus; the computer 5a can read the application program 54a from the portable recording medium 54, and install the application program 54a on the hard disk 51d. Similar to the previously described application program 34a, the application program 54a may be provided over an electrical communication line from an external apparatus connected to the computer 5a so as to be capable of communication over the electrical communication line (wireless or wired).

An operating system that provides a graphical user interface environment, such as Windows (trademark of Microsoft Corporation) or the like, and the application program 54 are installed on the hard disk 51d. In the following description, the application program 54a of the first embodiment operates on the aforesaid operating system.

Figure 18:
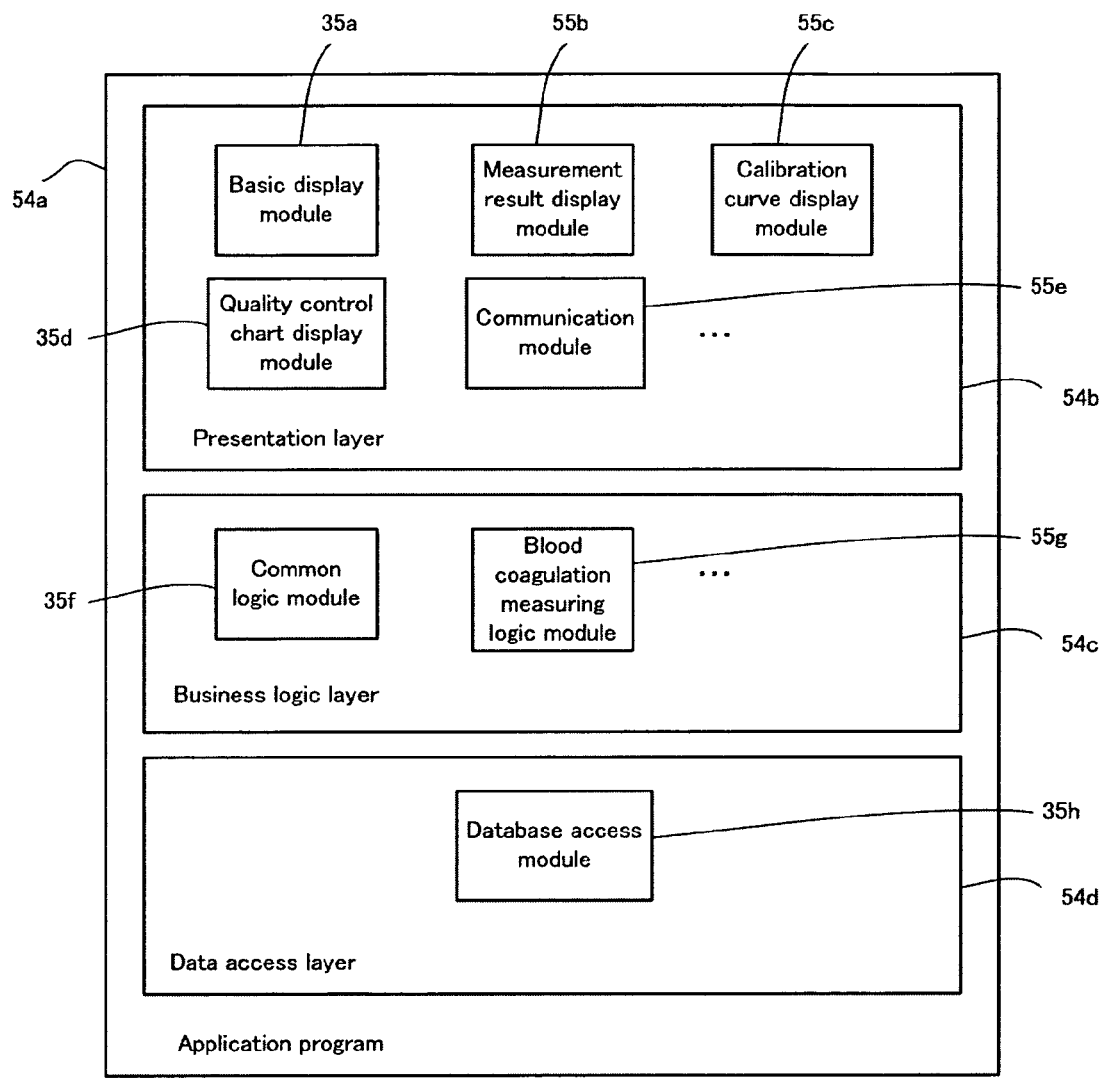
FIG. 18 is a schematic view showing the structure of the application program used by the blood coagulation measuring apparatus of the first embodiment.

FIG. 18 is a schematic view showing the structure of the application program 54a used by the blood coagulation measuring apparatus of the first embodiment. Similar to the application program 34a, the application program 54a has a tri-layered architecture including a presentation layer 54b, business logic layer 54c, and data access layer 54d. The presentation layer 54b is layer equivalent to a user interface part and communication part in the application program 54a; a basic display module 35a for executing a basic parts display in a window of the application program 54a, a measurement result display module 55b for displaying measurement results of the blood coagulation measuring apparatuses 4a and 4b on the display unit 52, a calibration curve display module 55c for displaying a calibration curve used in the calculation of the measurement results, quality control chart display module 35d for displaying a quality control screen, and communication module 55e for communicating with the blood coagulation measuring apparatuses 4a and 4b.

The business logic layer 54c is a layer equivalent to data processing and processing part in the application program 54a; a common logic module 35f that is common to all apparatus models and includes a unit conversion module for data unit conversion, and a quality control graph display data preparation module and the like, and a blood coagulation measurement logic module 55g for executing data processing characteristic of the blood coagulation measuring apparatuses and the like belong to the business logic layer 534c.

The data access layer 54d is a layer equivalent to the data access part in the application program 54a; a database access module 35h for accessing databases DB41 and DB42, which are described later, belongs to the data access layer 54d. The business logic modules 35a, 35d, 35f, 35h, 55b, 55c, 55e, and 55g are components of the application program, and are included in execution format files or dynamic link libraries. Although only the program modules 35a, 35d, 35f, 35h, 55b, 55c, 55e, and 55g are listed as program modules that configure the application program 54a, only these representative program modules are represented to simplify the description, and other program modules are actually present.

The basic display module 35a, quality control chart display module 35d, common logic module 35f, and database access module 35h are common modules of the application program of the blood coagulation measuring apparatuses, whereas the measurement result display module 55b, calibration curve display module 55c, communication module 55e, and blood coagulation measurement logic module 55g are model-dependent modules that are characteristic of the application program for the blood coagulation measuring apparatuses.

Similar to the previously described application program 34a, common modules and model-dependent modules of the application program 54a are stored in separate dynamic link libraries. The common modules of the application program 54a are stored in one dynamic link library, and the model-dependent modules are stored in another single dynamic link library (not shown in the drawing). The dynamic link library of the common modules is identical to the dynamic link library 35i of the application program 34a of the hemocyte analyzers. In this way there is unnecessary to develop a new dynamic link library, and the dynamic link library 35i can be diverted to the application program 54a simply by storing a copy of the dynamic link library 35i of the application program 34a in a predetermined storage location (directory) on the hard disk 51d. The common module also may be stored in a single dynamic link library, or may be divided and stored in a plurality of dynamic link libraries, and the model-dependent module may be stored in a single dynamic link library, or may be divided and stored in a plurality of dynamic link libraries.

Databases DB41 and DB42 are installed on the hard disk 51d. The database DB41 is a relational database for mutually associating and storing specimen numbers and measurement result data of the blood coagulation measuring apparatuses 4a and 4b. The database DB41 is configured with the same schema as the database DB21, and the measurement result data obtained from measurements by the blood coagulation measuring apparatuses 4a and 4b are stored in the database DB41 by the application program 54a. The application program 54a can also access the database DB41, read past measurement result data, and display the data on the display unit 52.

The database DB42 is a relational database for storing the setting data of the application program 54a. The setting data stored in the database DB42 are read by the CPU 51a during the operation of the application program 54a, and the read data is processed to [setting item], [setting condition], and [setting value] in the same manner as the database DB22. The a setting data tree is constructed using the processed data, and the setting content expressed by the data tree is reflected in the operation of the application program 54a. Since the data tree structure is identical to the structures of the data trees T1, T2, and T11 used by the application program 34a, further description is omitted.

Figure 19:
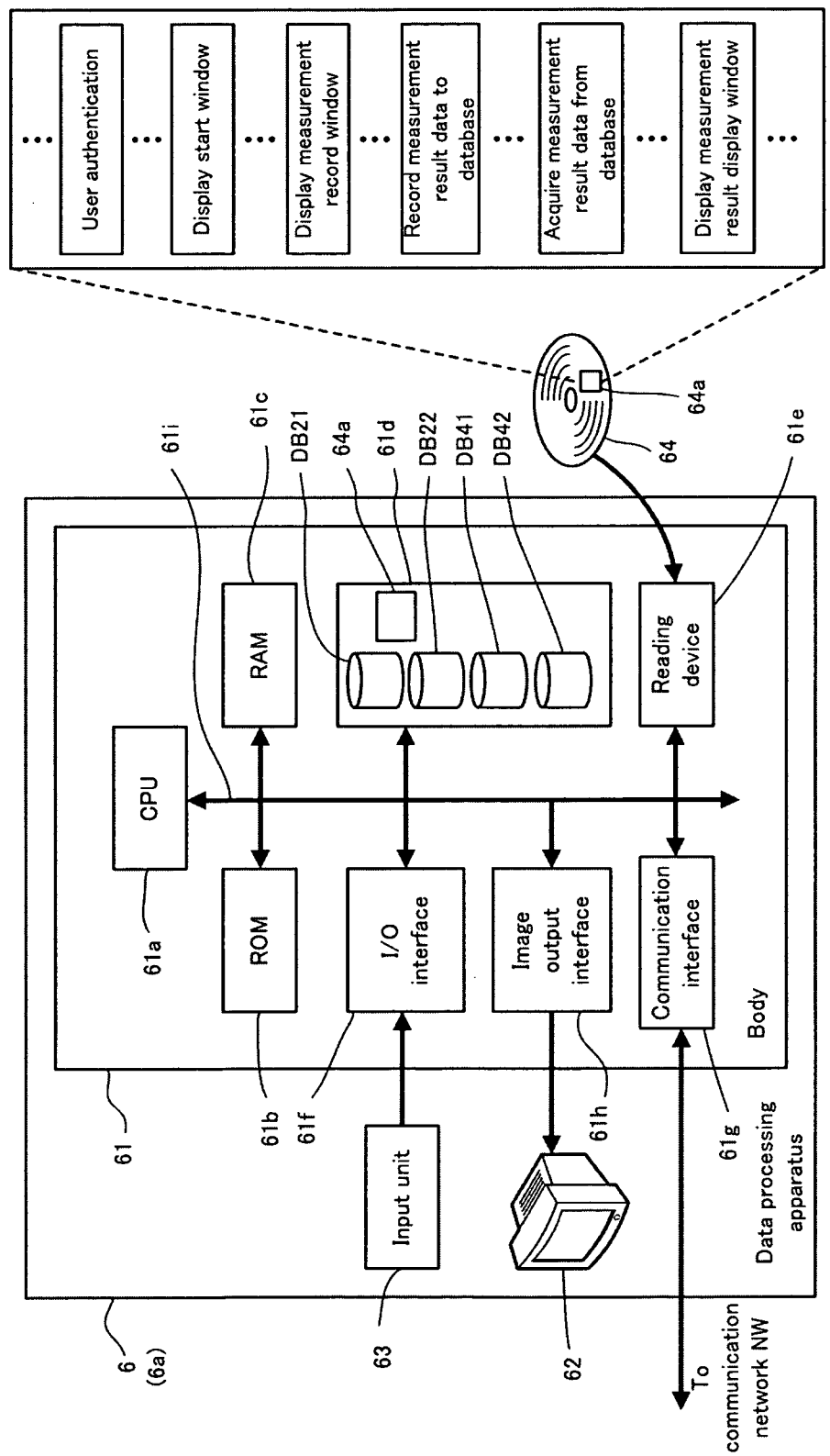
FIG. 19 is a block diagram showing the structure of the measurement result reference data processing apparatus of the hemocyte analyzer and blood coagulation measuring apparatus of the first embodiment.

The structure of the data processing apparatus 6 is described below. FIG. 19 is a block diagram showing the structure of the data processing apparatus 6 used for measurement result reference of all hemocyte analyzers 2a and 2b and blood coagulation measuring apparatuses 4a and 4b. As shown in FIG. 19, the data processing apparatus 6 is a computer 6a mainly configured by a body 61, display unit 62, and input unit 63. The body 61 is mainly configured by a CPU 61a, ROM 61b, RAM 61c, hard disk 61d, reading device 61e, I/O interface 61f, communication interface 61g, and image output interface 61h; the CPU 61a, ROM 61b, RAM 61c, hard disk 61d, reading device 61e, I/O interface 61f, communication interface 61g, and image output interface 61h are connected by a bus 61i. Since the structures of the CPU 61a, ROM 61b, RAM 61c, hard disk 61d, reading device 61e, I/O interface 61f, communication interface 61g, and image output interface 61h are identical to the structures of the CPU 31a, ROM 31b, RAM 31c, hard disk 31d, reading device 31e, I/O interface 31f, communication interface 31g, and image output interface 31h, further description is omitted.

A portable recording medium 64, which is readable by the reading device 61e, stores an application program 64a that enables a computer to function as a data processing apparatus for a measuring apparatus, such that the computer 6a can read the application program 64a from the portable recording medium 64, and install the application program 64a on the hard disk 61d. Similar to the previously described application program 34a, the application program 64a need not be provided by the portable recording medium 64, inasmuch as the application program 64a may be provided over an electrical communication line from an external apparatus connected to the computer 6a so as to be capable of communication by means of an electrical communication line (wired or wireless).

An operating system that provides a graphical user interface environment, such as Windows (trademark of Microsoft Corporation) or the like, and the application program 64a are installed on the hard disk 61d. In the following description, the application program 64a of the first embodiment operates on the aforesaid operating system.

Figure 20:
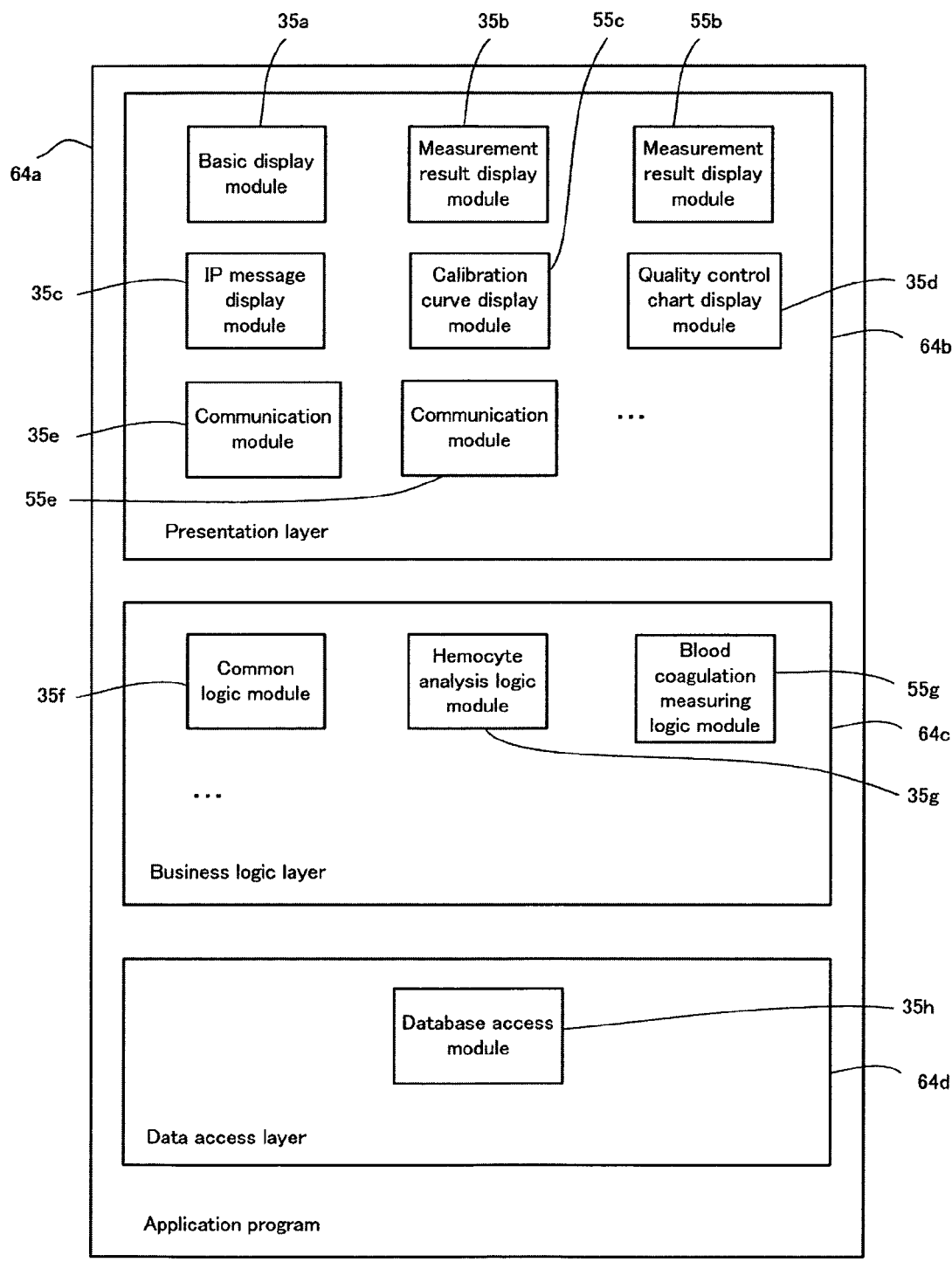
FIG. 20 is a schematic view showing the structure of the application program used for measurement result reference of the hemocyte analyzer and blood coagulation measuring apparatus of the first embodiment.

FIG. 20 is a schematic view showing the structure of the application program 64a for measurement result reference of all hemocyte analyzers 2a and 2b and blood coagulation measuring apparatuses 4a and 4b of the first embodiment. Similar to the previously described application program 34a, the application program 64a has a tri-layered architecture including a presentation layer 64b, business logic layer 64c, and data access layer 64d. The presentation layer 64b is layer equivalent to a user interface part and communication part in the application program 64a; a basic display module 35a for executing a basic parts display in a window of the application program 64a, a measurement result display module 35b for displaying measurement results of the hemocyte analyzers 2a and 2b on the display unit 62, a measurement result display module 55b for displaying measurement results of the blood coagulation measuring apparatuses 4a and 4b on the display unit 62, an IP message display module 35c for displaying an IP message indicating an abnormal specimen or suspected anomaly of the hemocyte analyzers 2a and 2b, calibration curve display module 55c for displaying a calibration curve used for calculating the measurement results of the blood coagulation measuring apparatuses 4a and 4b, a quality control chart display module 35d for displaying quality control screens of the hemocyte analyzers 2a and 2b and blood coagulation measuring apparatuses 4a and 4b, a communication module 35e for communicating with the hemocyte analyzers 2a and 2b, and communication module 55e for communicating with the blood coagulation measuring apparatuses 4a and 4b and the like belong to the presentation layer 64b.

The business logic layer 64c is a layer equivalent to data processing and operation part in the application program 64a; a common logic module 35f that is common to all apparatus models and includes a unit conversion module for data unit conversion, and a quality control graph display data preparation module and the like, and a hemocyte analysis logic module 35g for executing data processing characteristic of the hemocyte analyzers, and a blood coagulation measurement logic module 55g for executing data processing characteristics of the blood coagulation measuring apparatuses and the like belong to the business logic layer 64c.

The data access layer 64d is a layer equivalent to the data access part in the application program 64a; a database access module 35h for accessing databases DB21, DB22, DB41, and DB42 belongs to the data access layer 64d. The program modules 35a, 35b, 35c, 35d, 35e, 35f, 35g, 35h, 55b, 55c, 55e, and 55g are components of the application program, and are included in the execution format file and dynamic link library. Although only the program modules 35a, 35b, 35c, 35d, 35e, 35f, 35g, 35h, 55b, 55c, 55e, and 55g are listed as program modules that configure the application program 64a, only these representative program modules are represented to simplify the description, and other program modules are actually present.

The basic display module 35a, quality control chart display module 35d, common logic module 35f, and database access module 35h are common modules of the application program of the hemocyte analyzers, whereas the measurement result display module 35b, IP message display module 35c, communication module 35e, and hemocyte analysis logic module 35g are common program modules that are characteristic of the application program 34a for the hemocyte analyzers. The measurement result display module 55b, calibration curve display module 55c, communication module 55e, and blood coagulation measurement logic module 55g are common modules of the application program 54a for the blood coagulation measuring apparatuses.

Similar to the application programs 34a and 54a, although the common modules may be stored in a single dynamic link library 35i or may be divided and stored in a plurality of dynamic link libraries, and the model-dependent modules may be stored in a single dynamic link library or may be divided and stored in a plurality of dynamic link libraries, it is desirable that the common modules and model-dependent modules are stored in separate dynamic link libraries.

Databases DB21, DB22, DB41, and DB42 are installed on the hard disk 61d. The databases DB21 and DB22 installed on the hard disk 61d are databases having the same content as the databases DB21 and DB22 provided in the previously described processing apparatus 3, and the databases DB41 and DB42 installed on the hard disk 61d are databases having the same content as the databases DB41 and DB42 provided in the previously described data processing apparatus 5. The databases DB21, DB22, DB41, and DB42 are synchronous in real time with the databases DB21, DB22, DB41, and DB42 provided in the data processing apparatuses 3 and 5 by the function of the application programs 34a, 54a, and 64a. In this way the data processing of the hemocyte analyzers 2a and 2b can be performed by the data processing apparatus 6 even when a malfunction occurs in the data processing apparatus 3, and the data processing of the blood coagulation measuring apparatuses 4a and 4b can be performed by the data processing apparatus 6 even when a malfunction occurs in the data processing apparatus 5.

The database server 7 is configured by a computer, and a database containing information relating to previously performed testings is provided on a storage device such as a hard disk. The database is a relational database, that mutually associates and stores data such as testing day, specimen number, patient ID, measurement results of hemocyte analyzers, measurement results of blood coagulation measuring apparatuses, patient name, birth date, sex, age, blood type, ward, attending physician, specimen comments, patient comments and the like. The data processing apparatuses 3, 5, and 6 access the database server 7, and acquire measurement results associated with a specimen number and the like from the database, or record such data to the database.

The operation of the analysis system 1 of the first embodiment is described below. In the analysis system 1, the operation settings and operation start instructions of the hemocyte analyzers 2a and 2b can be performed, and the measurement results of the hemocyte analyzers 2a and 2b can be displayed, by a user using the data processing apparatus 3. Furthermore, the operation settings and operation start instructions of the blood coagulation measuring apparatuses 4a and 4b can be performed, and the measurement results of the blood coagulation measuring apparatuses 4a and 4b can be displayed, by a user using the data processing apparatus 5. Moreover, the operation settings and operation start instructions of the hemocyte analyzers 2a and 2b and blood coagulation measuring apparatuses 4a and 4b can be performed, and the measurement results of the hemocyte analyzers 2a and 2b and blood coagulation measuring apparatuses 4a and 4b can be displayed, by a user using the data processing apparatus 6. Although the data processing apparatuses 3, 5, and 6 can be used by any user, user authority may be set, for example, such that the data processing apparatus 3 can be used by operators of the hemocyte analyzers 2a and 2b, lab technicians performing hemocyte analysis of blood specimens, and clinical physicians performing testing or confirming test results; the data processing apparatus 5 can be used by operators of the blood coagulation measuring apparatuses 4a and 4b, lab technicians performing coagulation testing of blood specimens, and clinical physicians performing testing or confirming test results; and the data processing apparatus 6 can be used by supervisors (directing clinicians) capable of comparing all data of the hemocyte analyzers 2a and 2b and blood coagulation measuring apparatuses 4a and 4b. Furthermore, user authority may be set such that the support technicians of the hemocyte analyzers 2a and 2b and blood coagulation measuring apparatuses 4a and 4b can use and set all data processing apparatuses 3, 5, and 6.

Figure 21:
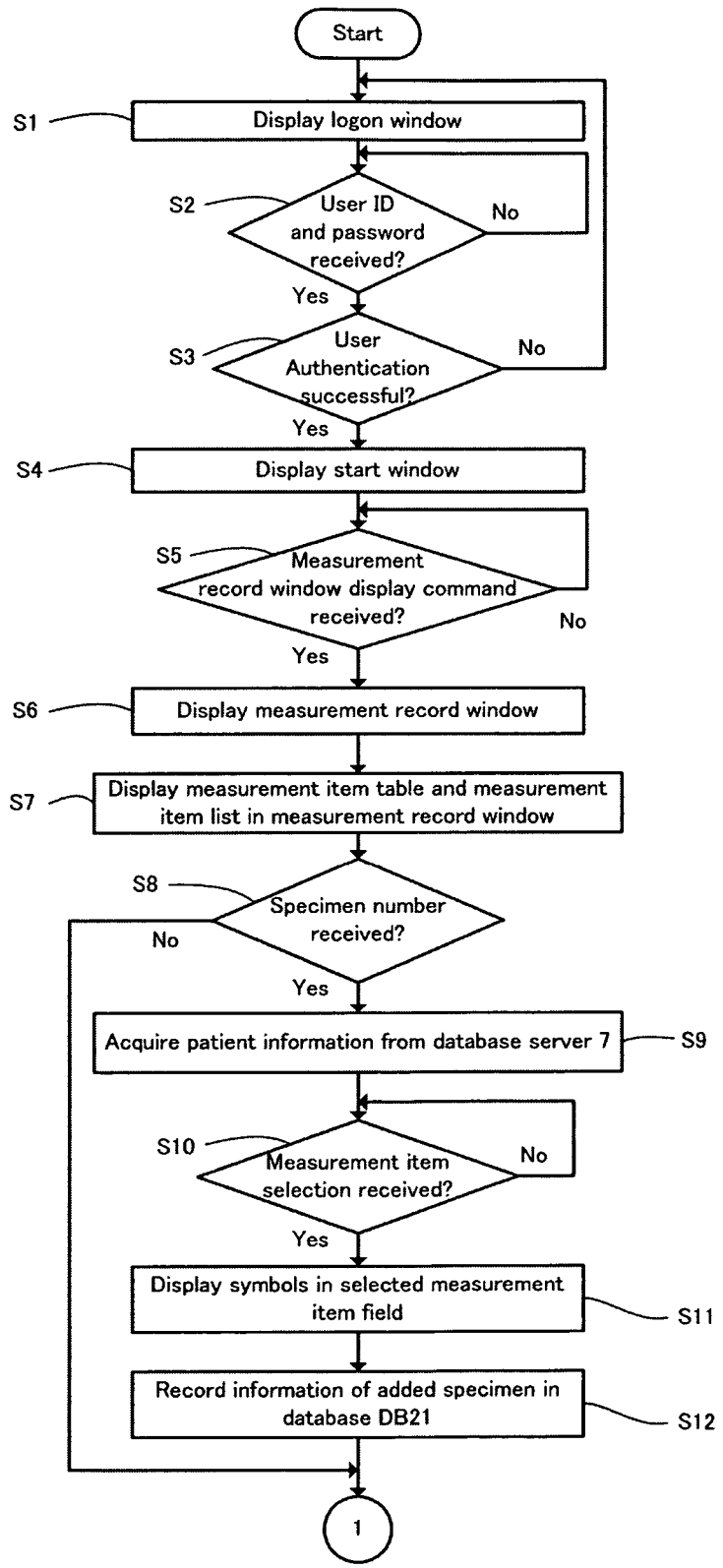
FIG. 21 is a flow chart showing the application program processing sequence when a specimen is measured by the hemocyte analyzer of the first embodiment.
Figure 22:
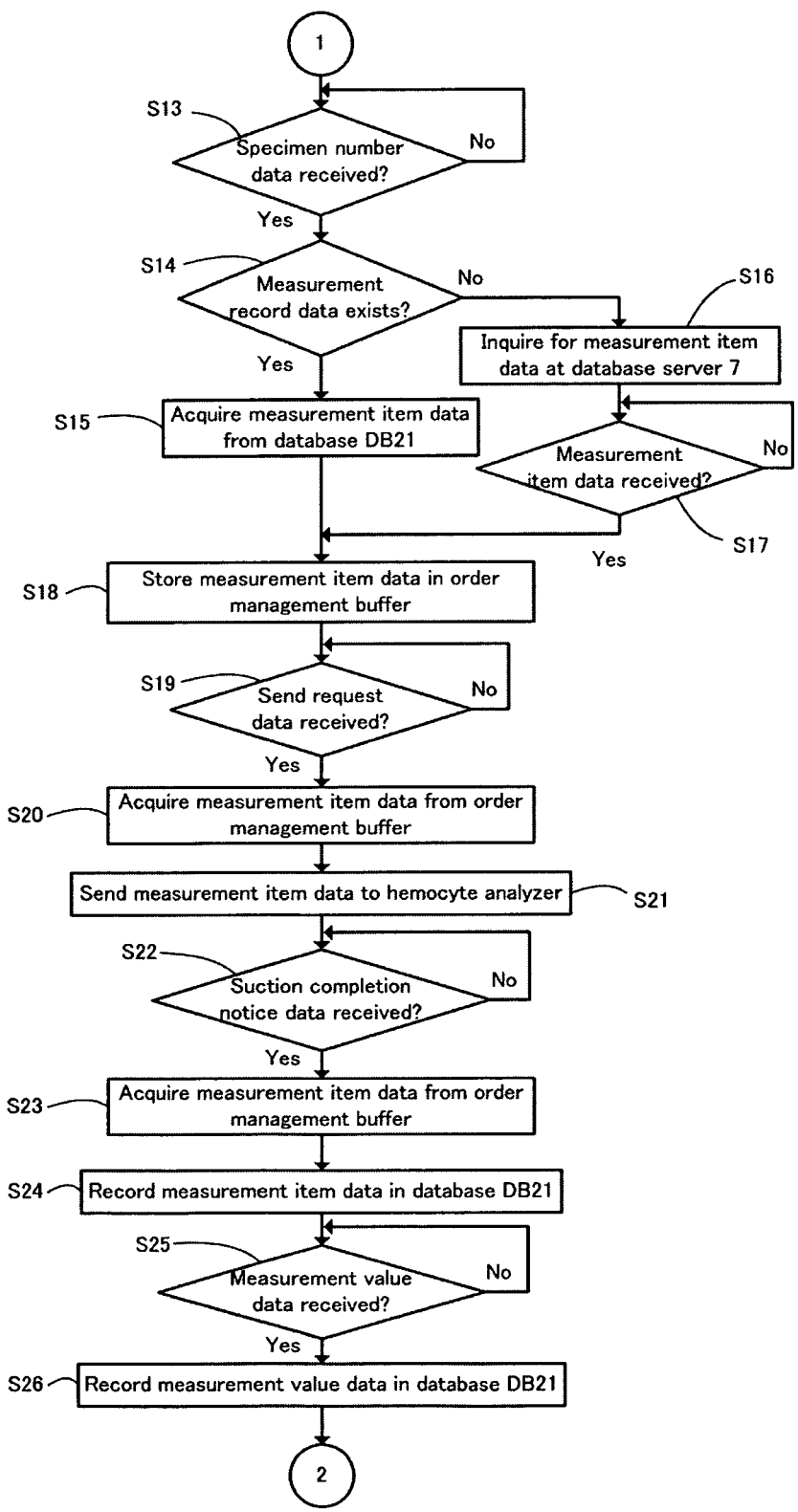
FIG. 22 is a flow chart showing the application program processing sequence when a specimen is measured by the hemocyte analyzer of the first embodiment.
Figure 23:
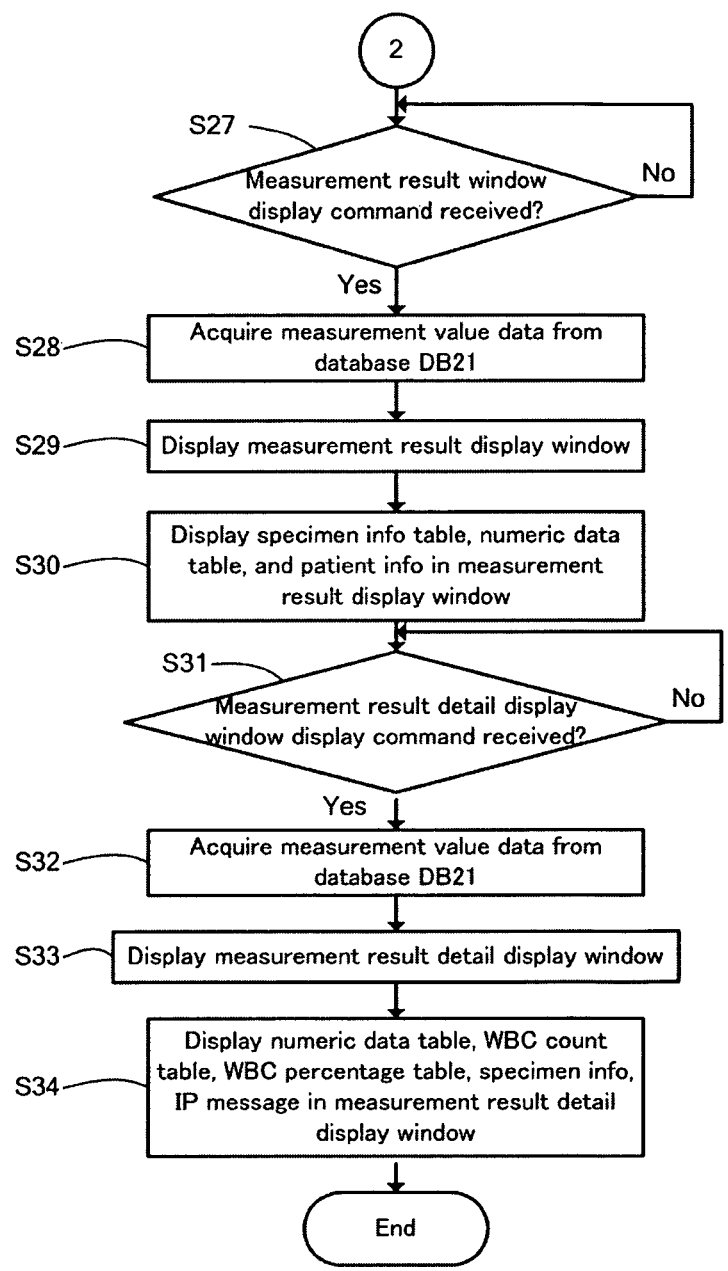
FIG. 23 is a flow chart showing the application program processing sequence when a specimen is measured by the hemocyte analyzer of the first embodiment.

The operation of the analysis system 1 is described below when the operator user of the hemocyte analyzers 2a and 2b operate the hemocyte analyzers 2a and 2b using the data processing apparatus 3 to measure specimens. FIGS. 21-23 are flow charts showing the processing sequence of the application program 34a when specimens are measured by operating the hemocyte analyzers 2a and 2b using the data processing apparatus 3. First, the operator starts the application program 34a. The CPU 31a of the computer 3a displays a logon window on the display unit 32 (step S1). The logon window is provided with input areas for inputting a logon ID and password, and the user moves the cursor to the input areas and inputs her login ID and password (not shown in the drawing). When the logon ID and password are received (step S2: YES), the CPU 31a accesses a user confirmation database (not shown in the drawing) for the application program 34a stored on the hard disk 31d, and authenticates the user by determining whether or not there is an account recording the logon ID and password, whether or not the account is valid, and whether or not the account expiration time has expired (step S3). When a user verification fails (step S3: NO), the CPU 31a returns the process to step S1. When user verification is successful in step S3 (step S3: YES), the CPU 31a displays a start window 81 on the display unit 32 (step S4). The display process of the start window 81 in step S4 is the main function of the basic display module 35a.

Figure 24:
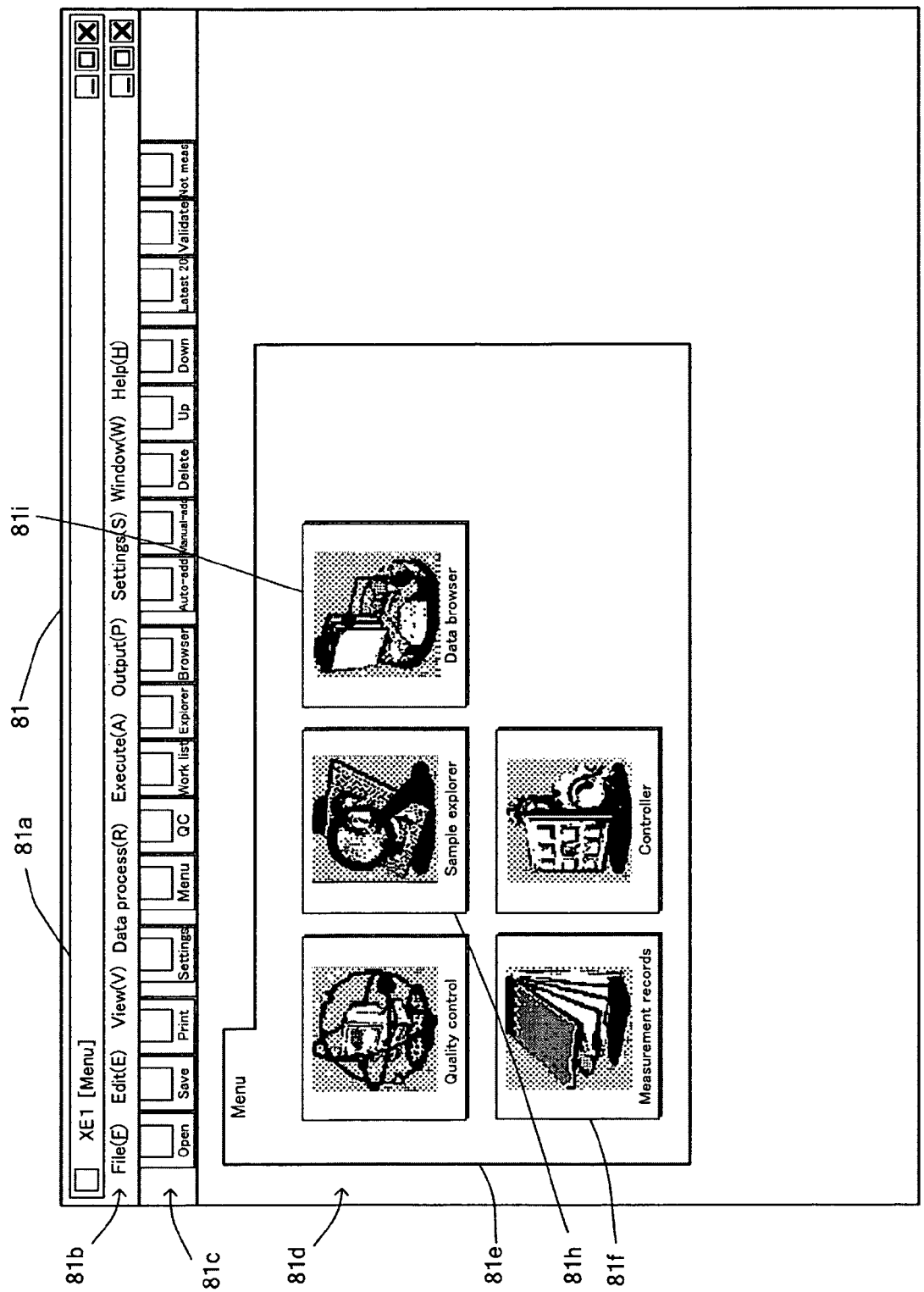
FIG. 24 is a schematic view of an example of the structure of an initial window of the application program used on the hemocyte analyzer of the first embodiment.

FIG. 24 is a schematic view showing the structure of the start window 81. As shown in FIG. 24, the start window 81 has a title display region 81a provided in the uppermost part of the window, a menu bar 81b provided below the title display region 81a, tool bar 81c provided below the menu bar 81b, and window display region 81d provided below the tool bar 81c. The title display region 81a displays the device name, display window name, number of stored specimens and the like. The menu bar 81b displays menus for [file], [edit], [view], [data operation], [execute], [output], [setting], [window], and [help]. Each of these menus are provided with a submenu, and the pull down submenu is displayed when the mouse pointer is positioned over the menu and the left button of the mouse is clicked (hereinafter referred to as 'left clicked'). The use of the menus can be limited through the user access restrictions, and restricted menus are displayed in a pale color (gray). Usable menus are displayed in black.

The tool bar 81c displays a plurality of buttons arranged horizontally. These buttons associate the items selected with relatively highest frequency from among the submenus displayed in the pulldown selection of the menus, such that a submenu can be quickly executed by left clicking the button of the tool bar 81c.

The window display region 81d displays a window for various types of operations and processes. As shown in FIG. 24, the start window 81 displays a menu window 81e in the window display region 81d. The menu window 81e displays a plurality of buttons. These buttons are associated with the submenus that are used with relatively high frequency, and the associated submenu can be executed and the object window opened by left clicking a button. Buttons can be freely added or removed by the user. A tab is provided at the top end of the window displayed in the window display region 81d. The name of the window is displayed on this tab. When a plurality of windows exist in the window display region 81d, the active window (window displayed in the foreground) can be changed by selecting the tab. In this way a plurality of processes or operations can be arrayed and executed by displaying a plurality of windows in the window display region 81d.

The data processing apparatus 3 awaits input of a command from a user in this state. The user can execute the various associated processes by left clicking a button in the menu window 81e, left clicking the button of the tool menu 81c, or starting the operation of the hemocyte analyzer 2a. Thus, this process is an event driven process, and although this process is different from processes executed by user command from this state, the operation when the measurement record button 81f in the menu window 81e is left clicked is described to simplify the description. When the measurement record button 81f is left clicked (step S5: YES), the CPU 31a displays the measurement record window 82 (step S6).

Figure 25:
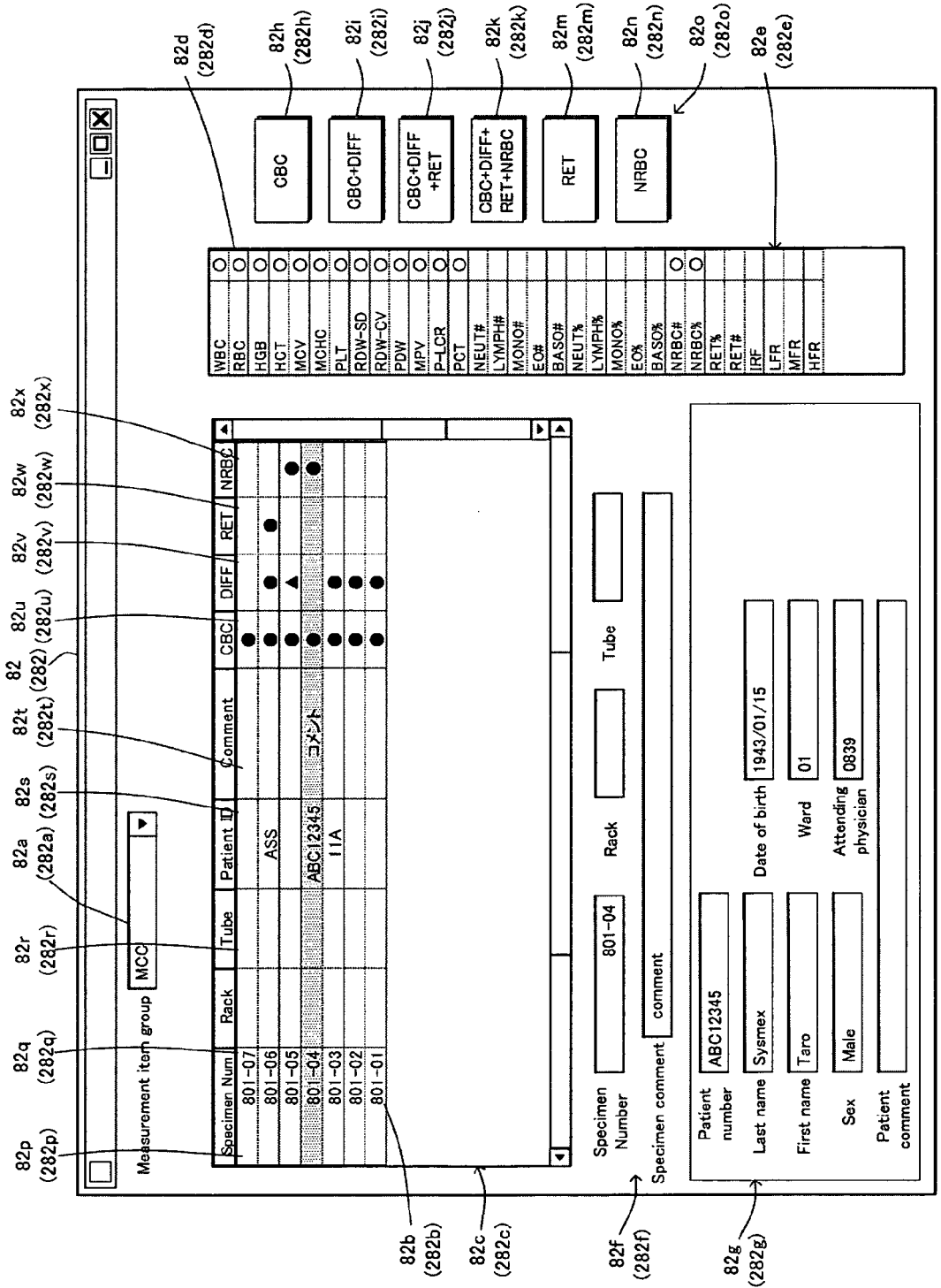
FIG. 25 is a schematic view of an example of the structure of a measurement record window of the application program used on the hemocyte analyzer of the first embodiment.

FIG. 25 is a schematic view showing the structure of the measurement record window 82. As shown in FIG. 25, the measurement record window 82 has a measurement item group selection box 82a provided a the top of the window, a measurement selection item table display region 82c for displaying a measurement selection items table 82 described later, measurement item list display region 82e for displaying a measurement item list 82d described later, specimen information input region 82f for inputting specimen information, patient information display region 82g for displaying patient information, and button display region 82o for displaying a plurality of buttons 82h, 82i, 82j, 82k, 82m, 82n for selecting measurement selection items.

The measurement item selection box 82a displays a pulldown menu of measurement item groups by left clicking a triangular arrow button displayed at the right end, and a user can select a desired measurement item group from this pulldown menu. The measurement item groups are set beforehand for each measuring apparatus for which the data processing apparatus does data processing; the present description pertains to setting the group referred to as [MCC] as the measurement item group for hemocyte analysis. The user selects [MCC] from among the groups displayed on the pulldown menu of the measurement item group selection box 82a. The [MCC] also may be set as a default measurement item group from the hemocyte analyzers 2a and 2b, which are the measuring apparatuses of the data processing apparatus 3. In this case, [MCC] is selected without the user performing an operation. In the flow charts shown in FIGS. 21-23, [MCC] is set by the default setting of the measurement item group in order to simplify the description.

When MCC is the selected measurement item group, the CPU 31a prepares a measurement item table 82b and measurement item list 82d, which are displayed in the measurement item table display region 82c and measurement item list display region 82e (step S7). As shown in FIG. 25, the measurement item table 82b has a specimen number field 82p, rack field 82q, tube field 82r, patient ID field 82s, comment field 82t, CBC field 82u, DIFF field 82v, RET field 82w, and NRBC field 82x. The specimen number field displays the specimen number input by the user. The rack field 82q and tube field 82r display the rack number and tube number input by the user. The patient ID field displays the patient ID corresponding to the specimen number of the same record. The comment field 82t displays input comments related to the specimen. The CBC field 82u displays either a circle, black circle, or black triangle symbol when the CBC is selected as the measurement item. The circle symbol indicates the measurement item (CBC) is not yet measured, the black circle symbol indicates the measurement item has been measured, and the black triangle symbol indicates the measurement item is currently being measured. CBC is a group of measurement items including white blood cell count (WBC), red blood cell count (RBC), hemoglobin (HGB), hematocrit value (HCT), mean red cell volume (MCV), mean corpuscular hemoglobin (MCH), mean corpuscular hemoglobin concentration (MCHC), platelet count (PLT), red cell distribution width (RDW-SD), red cell distribution width RDW-CV), platelet distribution width PDW), mean platelet volume (MPV), percentage large platelets (P-LCR), and platelet crit (PCT). The DIFF field 82v displays the above symbols when DIFF is selected as the measurement item of a specimen. DIFF is a group of measurement items including the percentage neutrophils (NEUT %), percentage lymphocytes (LYMPH %), percentage monocytes (MONO %), percentage eosinophils (EO %), percentage basophils (BASO %), number of neutrophils (NEUT#), number of lymphocytes (LYMPH#), number of monocytes (MONO#), number of eosinophils (EO#), and number of basophils (BASO#). The RET filed 82w displays the above symbols when RET is selected as the measurement item of a specimen. RET is a group of measurement items including percentage of reticulocytes (RET %), number of reticulocytes (RET#), percentage of high fluorescence reticulocytes (HFR), percentage of medium fluorescence reticulocytes (MFR), percentage of low fluorescence reticulocytes (LFR), and index of mature reticulocytes (IRF). The NRBC field 82x displays the above symbols when the NRBC is selected as the measurement item. NRBC is a group of measurement items including the percentage of nucleated red blood cells (NRBC %), and number of nucleated red blood cells (NRBC#). In the description using the example of FIG. 25, the sample having the sample number [801-05] is selected for measurement items CBC, DIFF, and NRBC, among which CBC and NRBC have already been measured, and DIFF is currently being measured.

When a user selects one specimen number from among the records displayed in the measurement item table 82b, the row of the selected specimen number is displayed in a highlight color than differs from the other rows. Then, the CPU 31a displays the measurement item setting condition for the selected specimen number in the measurement item list 82d. As shown in FIG. 25, the measurement items of the hemocyte analyzers are listed in the measurement item list 82d, and a circle symbol is displayed when the measurement item is set. According to the example of FIG. 25, the row of specimen number [801-04] has been selected, and since CBC and NRBC have been set as the measurement items for this specimen, the measurement item list 82d shows the following marked with a circle: WBC, RBC, HGB, HCT, MCV, MCH, MCHC, PLT, RDW-SD, RDW-CV, PDW, MPV, P-LCR, PCT, NRBC %, NRBC#.

The specimen information input region 82f displays input specimen information, and the patient information display region 82g displays patient information corresponding to the specimen information. The specimen information input region 82f is provided with input boxes for inputting the specimen number, rack, tube, and comments; a user can input specimen information (specimen number, rack, tube, and comments) by moving the cursor to the input box. The results entered in the input boxes are reflected in the measurement item table 82b, and the data are recorded in the database DB21. The patient information display region 82g is provided with boxes for displaying patient ID, surname, given name, sex, birth date, medical history, ward, attending physician, and patient comments, and the patient information is displayed in these display boxes. When the user has input the specimen information (step S8: YES), the CPU 31a sends the specimen information to the database server 7, and inquires from the database server 7 for any patient information corresponding to this specimen number. The database server 7 searches patient information using the specimen number as a search key, and sends patient information corresponding to this specimen number to the data processing apparatus 3. Thus, the CPU 31a acquires patient information (step S9). According to the example in FIG. 25, [801-04] is entered in the specimen number input box, and [comment] is entered in the various comment input boxes. This time the data processing apparatus 3 sends data representing the specimen number [801-04] to the database server 7, and requests the corresponding patient information. The database server 7 searches for corresponding patient information using the specimen number [801-04] as a search key, and acquires patient information corresponding to the specimen as a result of the search. The database server 7 sends the patient information to the data processing apparatus 3, and the data processing apparatus 3 displays the patient ID [ABC12345], surname [Sysmex], given name [Taro], sex [male], birth date [1943/01/15], ward [01], attending physician [0839] in the display boxes of the patient information display region 82g.

Buttons 82h, 82i, 82j, 82k, 82m, and 82n are provided in a vertical arrangement on the right side of the measurement item list display region 82e. The button 82h is for recording the CBC. And the CBC is recorded as a measurement item for the specimen number entered in the input box of the specimen information input region 82f at that time when the user left clicks the button 82h. Similarly, the buttons 82i, 82j, 82k, 82m, and 82n respectively record the CBC+DIFF, CBC+DIFF+RET, CBC+DIFF+RET+NRBC, RET, and NRBC as measurement items. When specimen information is input and a user left clicks the button 81i while the patient information is displayed (step S10: YES), the CPU 31a adds a new line to the measurement item table 82b, and the specimen number entered in the input box is displayed in this line of the specimen number field, and a circle is displayed in the CBC field and DIFF field (step S11). In the process of step S11, circles are displayed in the measurement item list 82d for the WBC, RBC, HGB, HCT, MCV, MCH, MCHC, PLT, RDW-SD, RDW-CV, PDW, MPV, P-LCR, PCT, NEUT %, LYMPH %, MONO %, EO %, BASO %, NEUT#, LYMPH#, MONO#, EO#, and BASO#. The CPU 31a accesses the database DB21 and records the specimen information, patient information, and measurement items (step S12). Thus, measurements can be recorded for a new specimen.

When the specimen measurement starts, the operator sets a collection tube containing the specimen in the rack, and places the rack in the transport unit provided at the front of the hemocyte analyzer 2a (2b). A barcode label indicating the specimen number is adhered to the collection tube. The collection tube is transported together with the rack to a specimen supply position below the sample supply position (not shown in the drawing) of the hemocyte analyzer 2a (2b), and during this transport the barcode is read by a barcode reader provided in the hemocyte analyzer 2a. The control unit 25 of the hemocyte analyzer 2a sends the specimen number data indicating the specimen number read from the barcode to the data processing apparatus 3. When the specimen number data from the hemocyte analyzer 2a are received (step S13: YES), the CPU 31a determines whether or not the previously mentioned measurement record data exist for that specimen number (step S14). This process is performed by referencing the database DB21, and determining whether or not measurement record data for the specimen number on the barcode exists. When measurement record data for the specimen number exists in the process of step S14 (step S14: YES), the CPU 31a reads the measurement items corresponding to the specimen number from the database DB21 (step S15), and moves the process to step S18 described later.

Figure 26:
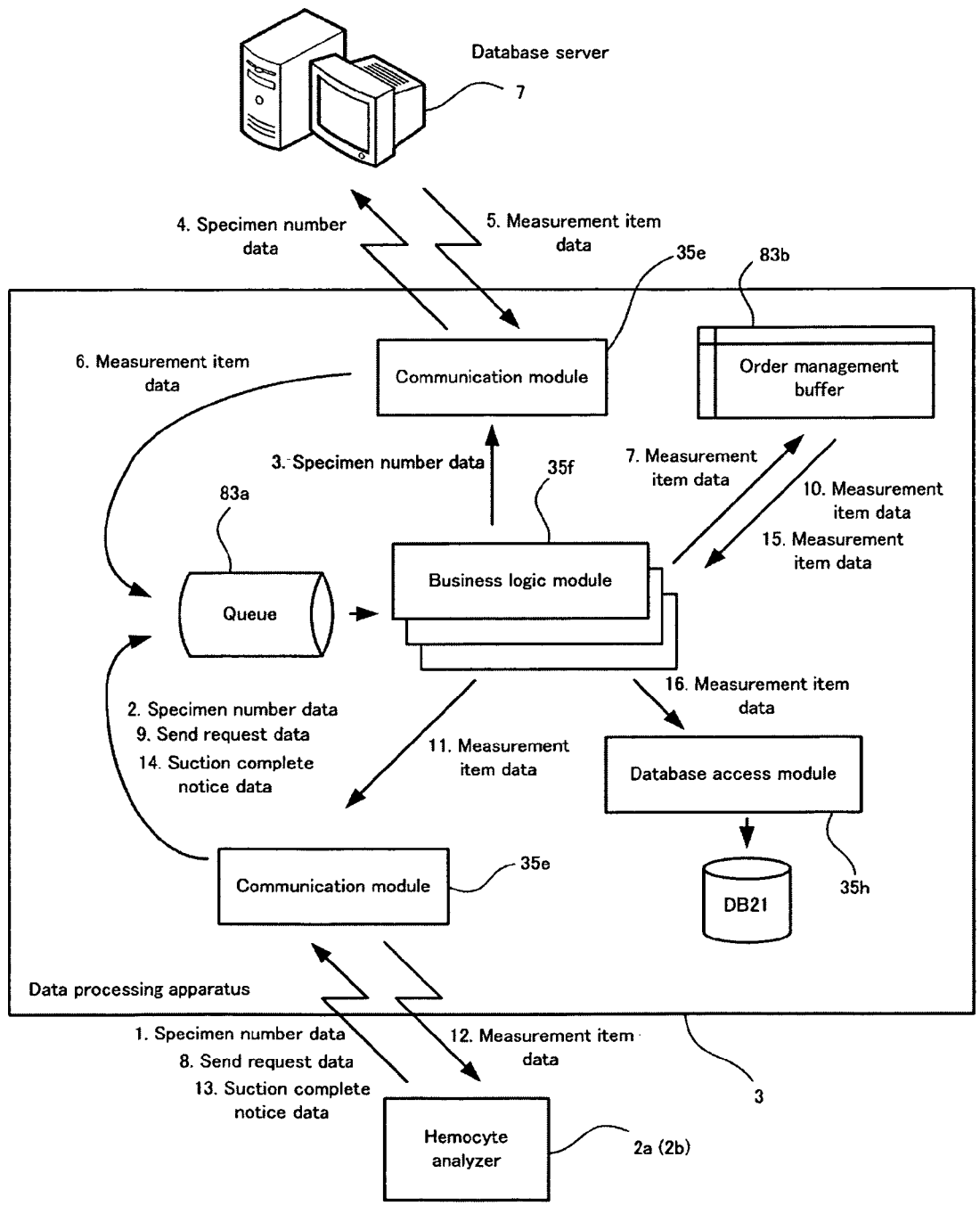
FIG. 26 is a schematic view showing the flow of the data to the measuring apparatus until the measurement order is issued.

When measurement records for the specimen number do not exist in step S14 (step S14: NO), the CPU 31a sends the specimen number data to the database server 7 to inquire about measurement items for this specimen (step S16). The data flow at this time is shown in FIG. 26. FIG. 26 is a schematic view showing the flow of the data to the measuring apparatus until the measurement order is issued. The reception of the specimen number data from the hemocyte analyzer 2a is executed by the communication module 35e. The specimen number data received by the communication module 35e is entered in a queue 83a. The specimen number data acquired from the queue 83a are supplied to the program modules (for example, the common logic module 35f) of the business logic layer 34c, and sent from the business logic layer 34c to the communication module 35e. Then, the communication module 35e sends the specimen number data to the database server 7, to inquire for measurement items for this specimen number.

The database server 7 searches for measurement items corresponding to the specimen using the specimen number data as a search key. Measurement items resulting from this search are sent to the originally requesting data processing apparatus 3 as measurement item data. when the measurement item data are received (step S17: YES), the CPU 31a stores the measurement item data in a order management buffer 83b provided in RAM 31c (step S18). The data flow at this time is shown in FIG. 26. The reception of the measurement items from the database server 7 is executed by the communication module 35e. The measurement item data received by the communication module 35e are entered in a queue 83a. The measurement item data acquired from the queue 83a are supplied to the program modules (for example, the common logic module 35f) of the business logic layer 34c. The program modules associate the acquired measurement item data with the specimen number data and store the data in the order management buffer 83b.

Thereafter, when, for example, the arrival of the collection tube containing the specimen to be measured at the specimen supply position in the hemocyte analyzer 2a is detected by a sensor not shown in the drawing and the control unit 25 is alerted, the control unit 25 transmits a send data request that request the transmission of the measurement items to the data processing apparatus 3. The send request data include the specimen number data of the specimen to be measured. When the send request data are received (step S19: YES), the CPU 31a acquires the measurement item data corresponding to the specimen number data included in the send request data from the order management buffer 83b (step S20), and sends the measurement item data to the hemocyte analyzer 2a (step S21). The data flow at this time is shown in FIG. 26. The reception of the send request data from the hemocyte analyzer 2a is executed by the communication module 35e. The send request data received by the communication module 35e are entered in a queue 83a. The send request data acquired from the queue 83a are supplied to the program modules (for example, the common logic module 35f) of the business logic layer 34c. The program module reads the measurement item data corresponding to the specimen number data included in the acquired send request data from the order management buffer 83b, and send the measurement item data to the communication module 35e. Then, the communication module 35e sends the received measurement item data to the hemocyte analyzer 2a.

Thereafter, the control unit 25 of the hemocyte analyzer 2a suctions the specimen from the collection tube in the sample supply unit. After the suctioning ends, the control unit 25 sends the suction completion notification data to the data processing apparatus 3 that suctioning has been completed. The suction completion notification data include the specimen number of the suction specimen. When the suction completion notification data have been received (step S22: YES), the CPU 31a acquires the measurement item data corresponding to the specimen number data included in the suction completion notification data from the order management buffer 83b (step S23), and associates the data with the specimen number and records the data in the database DB21. (step S24). The data flow at this time is shown in FIG. 26. The reception of the suction completion notification data from the hemocyte analyzer 2a is executed by the communication module 35e. The suction completion notification data received by the communication module 35e is entered in a queue 83a. The suction completion notification data acquired from the queue 83a are supplied to the program modules (for example, the common logic module 35f) of the business logic layer 34c. The program module reads the measurement item data corresponding to the specimen number data included in the acquired suction complete notification data from the order management buffer 83b, and sends the measurement item data and the specimen number data to the database access module 35h. Then, the database access module 35h associates the specimen number and the measurement items and records the data in the database DB21.

Next, the hemocyte analyzer 2a supplies the specimen suction from the collection tube to any unit among the optical detection unit 21, RBC detection unit 22, HGB detection unit 23, and IMI detection unit 24, and starts the measurement of the measurement items supplied for m the data processing apparatus 3. After completion of the measurements, the control unit 25 sends the measurement value data to the data processing apparatus 3. The measurement value data include the specimen number data. When the measurement value data are received (step S25: YES), the CPU 31a associates the measured value data with the specimen number and records the data in the database DB21 (step S26). When inputs instructions to display the measurement results (step S27: YES), the CPU 31a reads the measurement value data from the database DB21 (step S28), and displays the data in the measurement result display window (step S29). In the first embodiment, the display of the measurement result display window is executed when the user left clicks the sample explorer button 81h in the menu window 81e.

FIG. 27 is a schematic view showing the structure of the measurement result display window 84. As shown in FIG. 27, the measurement result display window 84 has a specimen information table display region 84b for displaying a specimen information table 84a described later, numeric data table display region 84d for displaying a numeric data table 83c described later, and patient information display region 84e for displaying patient information. The patient information display region 84e is identical to the patient information display region 82g of the previously mentioned measurement record window 82, and therefore further description is omitted.

As described above, when the sample explorer button 81h is left clicked, the CPU 31a acquires the measurement value data for the specimen and the specimen information for the specimen of previous measurements from the database DB21, and prepares a specimen information table 84a and numeric data table 84c from this information, and displays these tables in the specimen information table display region 84b and numeric data table display region 84d, and further displays the patient information in the patient information display region 84e (step S30). As shown in FIG. 27, the specimen information table 84a has a specimen number field 84f, measuring apparatus ID field 84h, measurement time field 84i, and measurement value fields 84j, 84k, 84m, 84n, 84o, 84p, 84q, and 84r. The specimen number field 84f displays the specimen numbers of previously measured specimens. The measuring apparatus ID field 84h displays the ID of the measuring apparatus that measured the specimen. The measurement time field 84i displays the time the specimen was measured. The measurement value fields 84j, 84k, 84m, 84n, 84o, 84p, 84q, and 84r display the measurement value for the specimen. Measurement item tabs 84s-84u are provided at the bottom of the specimen information table display region 84b. The CBC tab 83s, DIFF tab 84t, and RET tab 84u are described below. When the CBC tab 84s is selected, the measurement values of WBC, RBC, HGB, HCT, MCV, MCH, MCHC, PLT are displayed in the measurement value fields 84j, 84k, 84m, 84n, 84o, 84p, 84q, and 84r. When the DIFF tab 84t is selected, the specimen information table 84a is switched and the measurement values of DIFF measurement items are displayed in the measurement value field. When the RET tab 84u is selected, the measurement values for the RET measurement items are displayed in the measurement value field. The specimen number field 84f, measuring apparatus ID field 84h, and measurement time field 84i are displayed when any tab is selected. An NRBC tab may also be provided, and when this tab is selected, the measurement values for NRBC measurement items are displayed.

When the user selects the row related to a single specimen number among the records displayed in the specimen information table 84a, the selected row is displayed highlighted in a different color than the other rows. Then, the CPU 31a displays the measurement values for the selected specimen number in the numeric data table 84c. As shown in FIG. 27, the numeric data table 84c has hemocyte analysis measurement item field 84v, numeric data field 84w, and unit field 84x. The measurement item field 84v displays the name of the measurement item. The numeric data field 84w displays the measurement values of the specimen corresponding to the measurement item of that row. The unit field 84x displays the units of the measurement values of that row. The user can confirm the measurement results of the hemocyte analyzer 2a by displaying the results in the measurement results display window 84.

Figure 28:
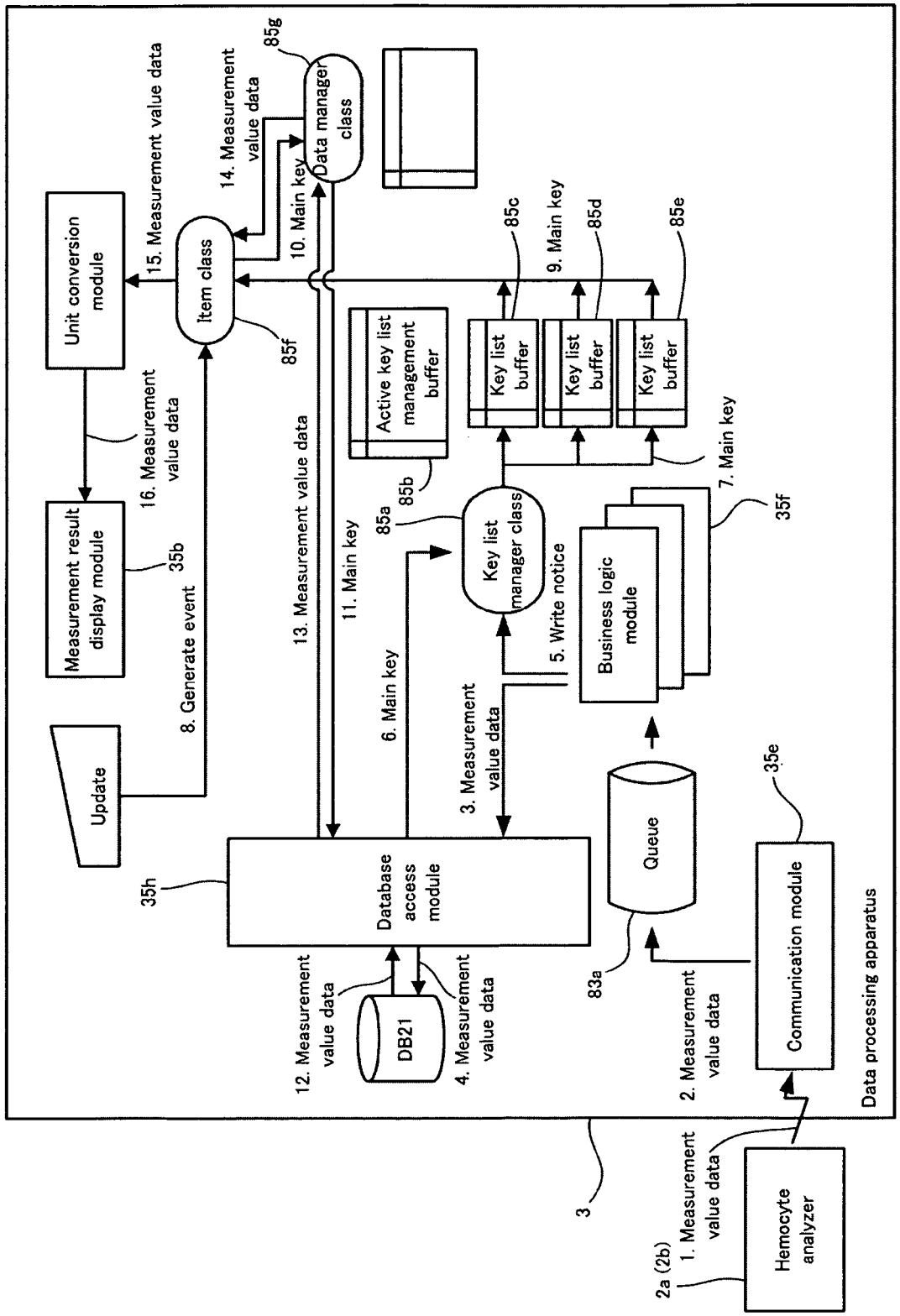
FIG. 28 is a schematic view showing the flow of data after the data processing apparatus has received the measurement value data from the measuring apparatus until the measurement results are displayed in the first embodiment.

The data flow after the data processing apparatus 3 has received the measurement value data from the hemocyte analyzer 2a until the data are displayed in the measurement results display window is described below using the drawings. FIG. 28 is a schematic view showing the data flow after the data processing apparatus 3 has received the measurement value data from the hemocyte analyzer 2a until the data are displayed in the measurement results display window. The reception of the measurement value data from the hemocyte analyzer 2a is executed by the communication module 35e. The measurement value data received by the communication module 35e are entered in a queue 83a. The measurement value data acquired from the queue 83a are supplied to the program modules (for example, the common logic module 35f) of the business logic layer 34c, and from the program module to the database access module 35h. Then, the database access module 35h associates the received measurement value data with the corresponding specimen number, and records the data in the database DB21. The business logic module notifies the key list manager class 85a belonging to the business logic layer 34c of the rewritten content of the database DB21. The key list manager class 85a inquires for the main key of the recorded record to the database access module. The key list manager class 85a refers to the active key list management buffer 85b, and specifies the key list buffer of the changed object. The RAM 31c is provided with the previously mentioned active key list management buffer 85b, and a plurality of key list buffers 85c-85e. The active key list management buffer 85b stores information specifying the key list buffer of the processing object, and the key list buffers 85c-85e store the main keys obtained from the database DB21. The key list manager class 85a stores the main keys obtained from the database access module 35h in the key list buffer specified by the active key list management buffer 85b, and updates the active key list management buffer 85b to set the next key list buffer to active status. Next, when an event is generated to display the measurement result display window, the item class 85f belonging to the business logic layer 34c references the active key list management buffer 85b, specifies the key list buffer corresponding to the measurement value to be displayed, and references this key list buffer to acquire the main key. The item class 85f inquires for the measurement value using the main key to the data manager class 85g belonging to the business logic layer 34c. The data manager class 85g is a class for managing the measurement value data, and acquires the measurement value data from the database DB21 through the database access module 35h. The item class 85f acquires the measurement value data corresponding to the main key, and passes these data to the unit conversion module belonging to the business logic layer 34c. The unit conversion module subjects the measurement value data to unit conversion, and supplies the converted measurement value data to the measurement result display module 35b. Then, the measurement value display window is displayed.

When the user inputs specifying the display of detailed information of the measurement results (step S31: YES), the CPU 31a reads the measurement value data from the database DB21 (step S32), and displays the data in the measurement result details display window (step S33). In the first embodiment, the measurement result details display window is opened when the user double clicks the specification information table 84a within the measurement results display window 84. The measurement result details display window is also displayed when the user left clicks the data browser button 81i in the menu window 81e.

FIG. 29 is a schematic view showing the structure of the measurement result details display window 86. As shown in FIG. 29, the measurement result details display window 86 has an anomaly display region 86a for displaying whether or not the measurement result is anomalous, specimen information display region 86b for displaying specimen information, and details display region 86c for displaying various types of details of the measurement results. The anomaly display region 86a is provided at the top left part of the measurement result details display window 86; [positive] is displayed when an anomaly is found in a hemocyte measurement value or hemocyte image, and the type of anomaly is display by double clicking [positive]. [Negative] is displayed in the anomaly display region 86a when there is no anomaly or measurement error. The specimen information display region 86b is provided with display boxes for displaying the specimen number, patient ID, patient name, sex, birth date, ward, attending physician, measurement date, measurement time, and comments, and the specimen information is displayed in these display boxes.

The detailed information display region 86c displays a window for displaying detailed information related to the types of measurement results. FIG. 29 shows a hemocyte analysis main window 86d displayed in the detailed information display region 86c. The hemocyte analysis main window 86d has numeric data display region 86e for displaying numeric data of each measurement item, white cell 5-category display region 86f for displaying the numbers and percentages of the five categories of white cells, and flag display region 86g for displaying IP messages indicating a suspected specimen anomaly for each type of measurement item.

The numeric data display region 86e displays numeric data table 86h that shows the numeric data and units for each measurement item. The numeric data table 86h has measurement item, numeric data and unit fields, and displays numeric data for each measurement item in table format. The numeric data table 86h displays an SD bar representing a graphical table of the dislocation from the normal range of measurement values for each measurement item, and the user can easily confirm the extent of such variation of the measurement values from the normal range by this means.

The white cell 5-categories display region 86*f* displays a white cell count data table 86*i* for displaying the numeric data and units of the number of white cells for each measurement item, and a white cell percentage data table 86*j* for displaying numeric data and units of the percentage numbers of white cells for each measurement item. The white cell numeric data table 86*h* has measurement item, numeric data and unit fields, and displays measurement items, that is, NEUT#, LYMPH#, MONO#, EO#, and BASO# for each measurement item related to the number of white cells in table format. The white cell numeric data table 86*i* displays an SD bar representing a graphical table of the dislocation from the normal range of measurement values for each measurement item. The white cell percentage data table 86*j* has measurement item, numeric data and unit fields and displays numeric data for measurement items, that is, NEUT %, LYMPH %, MONO %, EO %, and BASO % for each measurement item related to the percentages of white cells in table format.

The flag display region 86*g* displays a first IP message display box 86*k* for displaying a IP message related to WBC, a second IP message display box 86*m* for displaying a IP message related to RBC and RET, and a third IP message display box 86*n* for displaying a IP message related to PLT. IP messages include abnormal IP messages indicating an clear anomaly in the specimen, and suspect IP messages indicating a suspected anomaly of the specimen; and IP messages of the corresponding measurement items are listed in the first IP message display box 86*k*, second IP message display box 86*m*, and third IP message display box 86*n*.

As described above, when data in the specimen information table 84*a* is double clicked, or when the data browser button 81*i* is left clicked, the CPU 31*a* acquires the specimen information related to the previously measured specimen and measurement value data related to the same specimen from the database DB21, and prepares numeric data table 86*h*, white cell count data table 86*i*, and white cell percentage data table 86*j* from this information, and displays the respective data in the numeric data display region 86*e* and white cell 5-category display region 86*f*, and further displays specimen information in the specimen information display region 86*b*, and IP messages in the flag display region 86*g* (step S34). Then, when end instruction input is received from the user, the CPU 31*a* ends the process. In addition to the hemocyte analysis main window 86*d*, a graph window for graphically displaying measurement results, WBC window for displaying details of the white cells, RBC window for displaying details of the red cells may be opened in the detailed information display region 86*c*. These windows can be displayed by switching among the windows using the tabs provides at the top of the detailed information display region 86*c*. For example, when [Main (MCC)] tab is left clicked, the hemocyte analysis main window is displayed, when the [Graph (MCC)] tab is left clicked, the graph window is displayed.

The operation of the analysis system 1 is described below when the operator users operate the blood coagulation measuring apparatuses 4*a* and 4*b* to measure specimens using the data processing apparatus 5. First, the operator starts the application program 54*a*. In this case, similar to the application program 34*a*, the CPU 51*a* of the computer 5*a* displays a logon window on the display unit 52, and the user verification is performed when the logon ID and password input are received. When user verification is successful, the start window is displayed on the display unit 52. The display process of the start window is the main function of the basic display module 35*a*.

The structure of the start window is identical to the start window 81 of the application program 34*a* used by the hemocyte analyzers 2*a* and 2*b* shown in FIG. 24. This window is used to display the start window by the basic display module 35*a* jointly used by the application program 34*a*. Since the hemocyte analyzers 2*a* and 2*b* and the blood coagulation measuring apparatuses 4*a* and 4*b* are measuring devices, the process content of the application programs 34*a* and 54*a* used to display measuring results and the like have many aspects in common. Therefore, parts of the structures of the application programs may be reasonably used jointly, thereby reducing the number of development processes of the application programs 34*a* and 54*a*. Furthermore, the burden on the user of having different user interfaces for each application program, for example, the work of learning to operate each application program, can be reduced by having a unified user interface, and the additional application program 54*a* can be operated with a certain degree of expertise if the operation of the application program 34*a* is learned, thereby improving the convenience of easily learning the additional operation.

Figure 30:
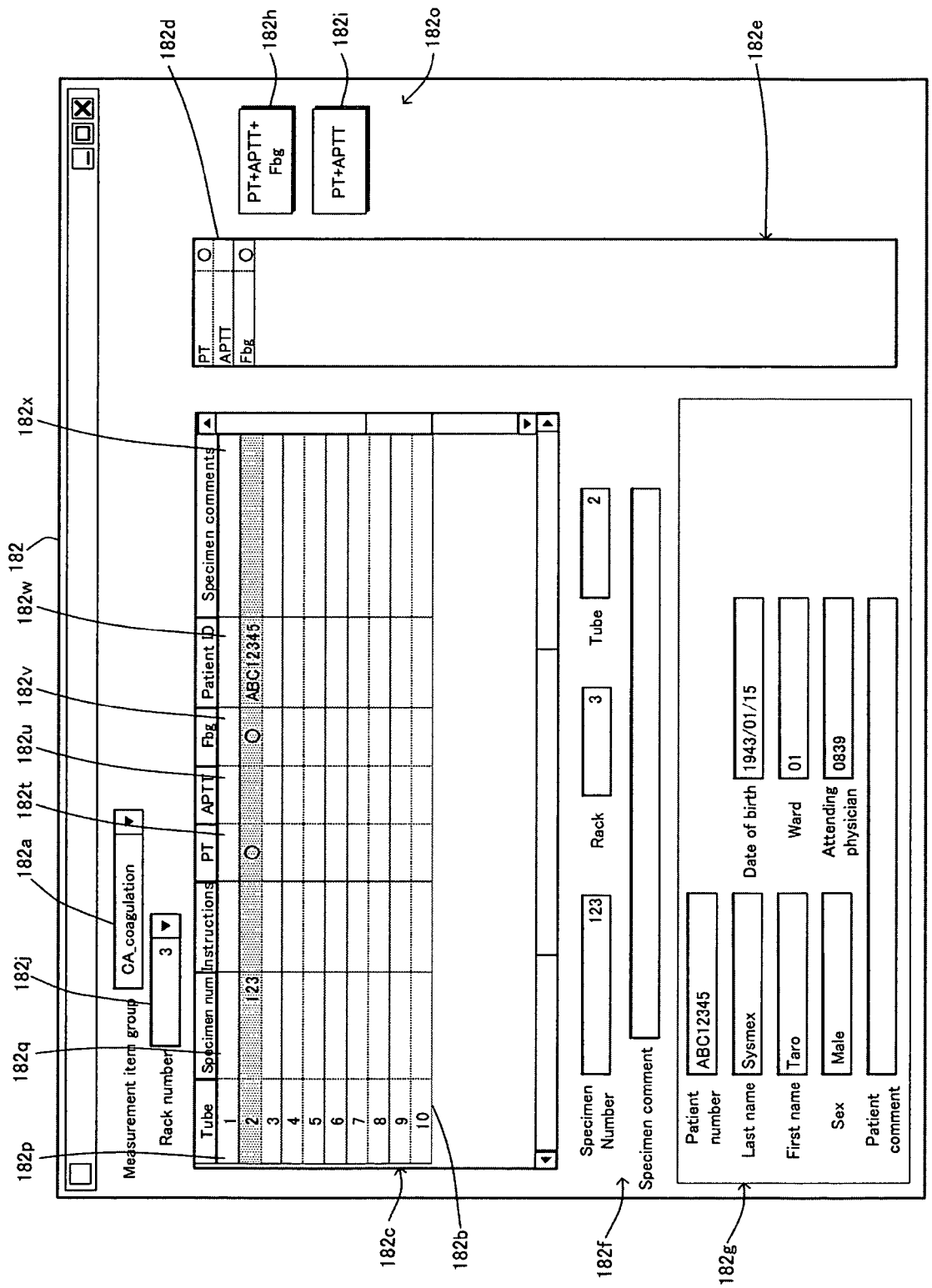
FIG. 30 is a schematic view of an example of the structure of a measurement record window of the application program used on the blood coagulation measuring apparatus of the first embodiment.

When the user left clicks the measurement record button in the main menu of the start window, the CPU 51*a* displays the measurement record window 182. FIG. 30 is a schematic view showing the structure of the measurement record window 182. As shown in FIG. 30, the measurement record window 182 has a measurement item group selection box 182*a* provided a the top of the window, rack number selection box 182*j* for selecting a rack number, measurement selection item table display region 182*c* for displaying a measurement selection items table 182*b* described later, measurement item list display region 182*e* for displaying a measurement item list 182*d* described later, specimen information input region 182*f* for inputting specimen information, patient information display region 182*g* for displaying patient information, and button display region 182*o* for displaying a plurality of buttons 182*h* and 182*i* for selecting measurement selection items. In this way the structure of the measurement record window 182 is similar to the structure of the measurement record window 82 of the application program 34*a*. Since the structures of the measurement item group selection box 182*a*, specimen information input region 182*f*, and patient information display region 182*g* are identical to the structures of the measurement item group selection box 82*a*, specimen information input region 82*f*, and patient information display region 182*g*, further description is omitted.

The case wherein the measurement item group [CA_coagulation method] is set in relation to the blood coagulation measurement is described below as the measurement item group. The CA_coagulation method is a group of measurement items for measurement by a biological activity method, that is, prothrombin time (PT), active part thromboplastin time (APTT), fibrinogen (Fbg) and the like. The user selects [CA_coagulation method] from among the groups displayed on the pulldown menu of the measurement item group selection box 182*a*. When the [CA_coagulation method] is set as the default, the user can omit the input operation. Thus, when the [CA_coagulation method] is selected, the CPU 51*a* prepares a measurement item table 182*b* and measurement item list 182*d*, which are respectively displayed in the measurement item table display region 182*c* and measurement item list display region 182*e*.

As shown in FIG. 30, the measurement item table 182*b* has a tube field 182*p*, specimen number field 182*q*, measurement assignment field 182*s*, PT field 182*t*, APTT field 182*u*, Fbg field 182v, patient ID field 182w, and specimen comment field 182x. The tube field 182p displays the tube number. The specimen number field 182q displays the specimen number entered in the specimen information input region 182f. When PT is recorded as the measurement item, the PT field 182t displays a circle, black circle, or black triangle symbol for the object specimen. The meaning of the symbols is identical to the symbols in the previously described application program 34a, and therefore further description is omitted. When APTT is recorded as the measurement item, the APTT field 182u displays one of the symbols for the object specimen. When Fbg is recorded as the measurement item, the Fbg field 182v displays one of the symbols for the object specimen. In the example of FIG. 30, the specimen number [123] disposed at rack number [3], tube number [2], has the measurement items PT and Fbg recorded, and neither measurement has been performed.

When a user selects one specimen number from among the records displayed in the measurement item table 182b, the row of the selected specimen number is displayed in a highlight color than differs from the other rows. Then, the CPU 51a displays the measurement item setting condition for the selected specimen number in the measurement item list 182d. As shown in FIG. 30, when the measurement item list 182d displays a list of the measurement items in the biological activity method and the measurement objects are set for these measurement items, a circle is displayed. In the example of FIG. 30, since the row of specimen number [123] is selected, and PT and Fbg are selected as measurement items for this specimen, circles are displayed relative to PT and Fbg in the measurement item list 182d.

Buttons 182h and 182i are vertically arranged to the right of the measurement item list display region 182e. The button 182h is used to record PT+APTT+Fbg and PT, APTT, and Fbg are recorded as measurement items for the specimen number entered in the input box of the specimen information input region 182f at that time when the user left clicks the button 182h. Similarly, the button 182i is used to record PT+APTT as the measurement items.

When the specimen information is input by the user, the CPU 51a sends the specimen number to the database server 7, and inquires for patient information corresponding to the specimen number from the database server 7. The database server 7 searches patient information using the specimen number as a search key, and sends patient information corresponding to this specimen number to the data processing apparatus 3. Thus, the CPU 51a acquires patient information. In the example of FIG. 30, [123] is entered in the specimen number input box, and [3] is entered in the rack input box. This time the data processing apparatus 3 sends data representing the specimen number [123] to the database server 7, and requests the corresponding patient information. The database server 7 searches for corresponding patient information using the specimen number [123] as a search key, and acquires patient information corresponding to the specimen as a result of the search. The database server 7 sends the patient information to the data processing apparatus 3, and the data processing apparatus 3 displays the patient ID [ABC12345], surname [Sysmex], given name [Taro], sex [male], birth date [1943/01/15], ward [01], attending physician [0839] in the display boxes of the patient information display region 182g.

The user also may specify the rack number using the rack number selection box 182j rather than entering the rack number in the rack number input box as described above. In this case, the user displays the pulldown menu of the rack number selection box 182j, and selects a desired rack number from among the list.

When the user left clicks the button 182i after the specimen number is input, the specimen number in the input box is displayed in the specimen number field corresponding to the input rack number and tube number, and circles are displayed in the PT field and APTT field. In this case, a circle is displayed relative to PT and APTT in the measurement item list 182d. The CPU 51a accesses the database server 7, and records the information. Thus, measurements can be recorded for a new specimen.

When the specimen measurement starts, the operator sets a collection tube containing the specimen in the rack, and places the rack in the transport unit provided at the front of the blood coagulation measuring apparatus 4a (4b). A barcode label indicating the rack number specifying the rack is adhered to the rack, a barcode label indicating the tube number specifying the tube is adhered to the tube, and a barcode label indicating the specimen number of the specimen contained in the tube is also adhered to the tube. The collection tube is transported by the rack to the specimen supply position below the sample supply unit (not shown in the drawing) of the blood coagulation measuring apparatus 4a (4b), and during the transport the barcodes are read by a barcode reader provided in the blood coagulation measuring apparatus 4a. the control unit 42 of the blood coagulation measuring apparatus 4a sends data indicating the rack number, tube number, and specimen number read by the barcode reader to the data processing apparatus 5. When the data are received from the blood coagulation measuring apparatus 4a, the CPU 51a determines whether or not measurement record data exist for the rack number, tube number, and specimen number. This process is performed by referencing the database server 7 to determine whether or not records exist for the rack number, tube number, and specimen number. When measurement record data exist for the rack number, tube number, and specimen number, the CPU 51a reads the corresponding measurement items from the database server 7.

When measurement record data do not exist for the rack number, tube number, and specimen number, the CPU 51a sends the specimen number data to the database server 7 and inquires about measurement items for this specimen. The database server 7 searches for measurement items corresponding to the specimen using the specimen number data as a search key. Measurement items resulting from this search are sent to the originally requesting data processing apparatus 5 as measurement item data. When the measurement item data are received, the CPU 51a stores the data in an order management buffer provided in the RAM 51c.

Thereafter, when, for example, the arrival of the collection tube containing the specimen to be measured at the specimen supply position in the blood coagulation measuring apparatus 4a is detected by a sensor not shown in the drawing and the control unit 42 is alerted, the control unit 42 transmits a send data request that requests the transmission of the measurement items to the data processing apparatus 5. The send request data include the specimen number data of the specimen to be measured. When the send data request is received, the CPU 51a acquires the measurement item data corresponding to the specimen number data included in the send data request from the order management buffer, and sends the measurement item data to the blood coagulation measuring apparatus 4a. The flow of the data in this case is identical to the flow of the data in the data processing apparatus 3 described in FIG. 26, and further description is therefore omitted.

Thereafter, the control unit 42 of the blood coagulation measuring apparatus 4*a* suctions the specimen from the collection tube in the sample supply unit. After the suctioning ends, the control unit 42 sends the suction completion notification data to the data processing apparatus 5 as notification that suctioning has been completed. The suction completion notification data include the specimen number of the suction specimen. When the suction completion notification data are received, the CPU 51*a* acquires the measurement item data corresponding to the specimen number data included in the suction completion notification data from the order management buffer, and associates the data with the specimen number and sends the information to the database DB41.

Then, the blood coagulation measuring apparatus 4*a* supplies the specimen suctioned from the collection tube and starts the measurements according to the measurement items received from the data processing apparatus 5. After completion of the measurements, the control unit 42 sends the measurement value data to the data processing apparatus 5. The measurement value data include the specimen number data. When the measurement value data are received, the CPU 51*a* associates the data with the specimen number and records the data in the database DB41. When the user inputs instructions to display the measurement results, the CPU 51*a* reads the measurement value data from the database DB41, and displays the data in the measurement result display window. In the present embodiment, the measurement result display window is displayed when the user left clicks the sample explorer button in the menu window in the same manner as for the data processing apparatus 3.

Figure 31:
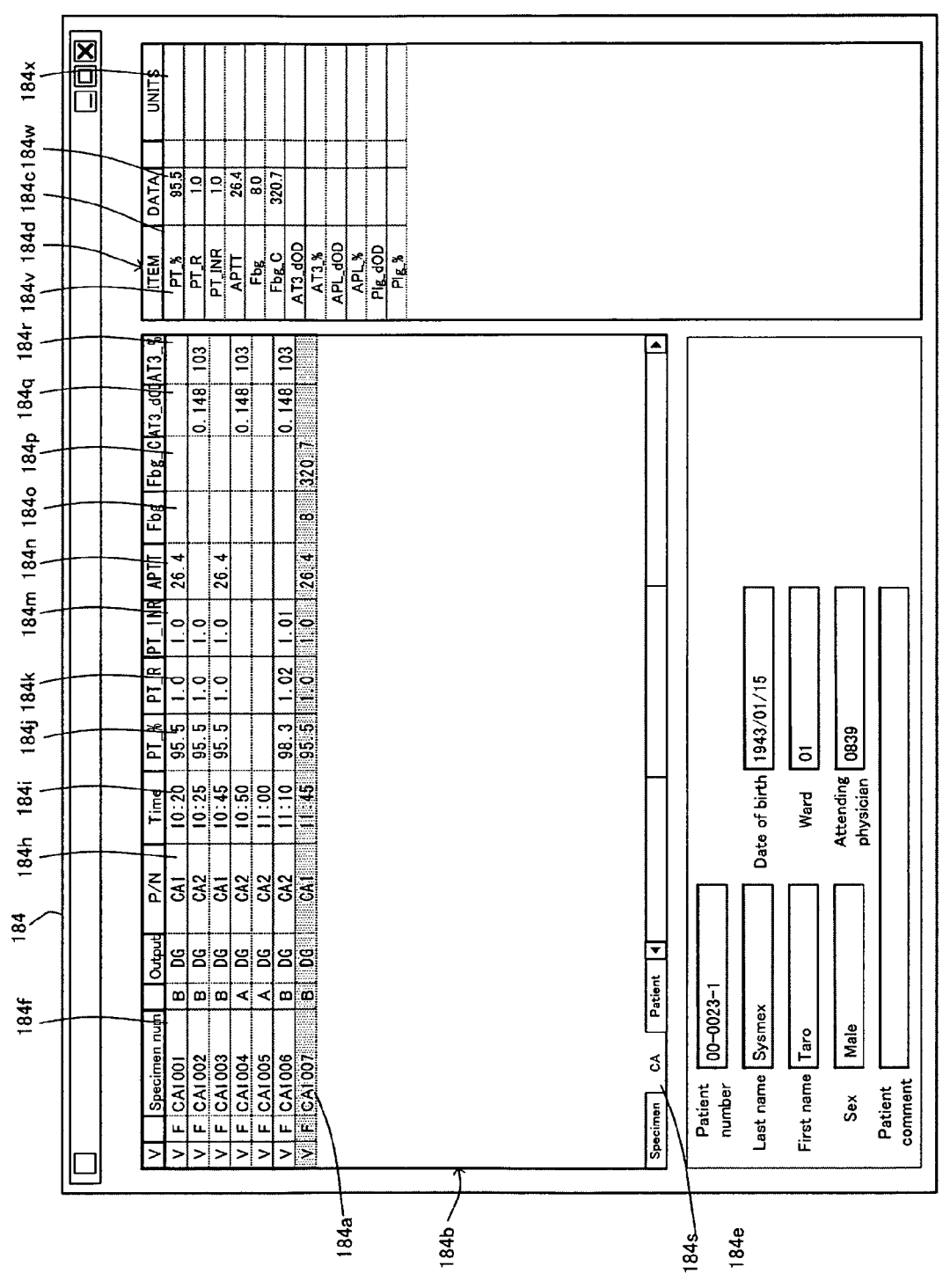

FIG. 27 is a schematic view showing the structure of the measurement result display window 184. As shown in FIG. 31, the measurement result display window 184 has a specimen information table display region 184*b* for displaying a specimen information table 184*a*, numeric data table display region 184*d* for displaying a numeric data table 183*c* described later, and patient information display region 184*e* for displaying patient information. The patient information display region 184*e* is identical to the patient information display region 84*e* of the measurement result display window shown in FIG. 27, and therefore further description is omitted.

As described above, when the sample explorer button is left clicked, the CPU 51*a* acquires the measurement value data for the specimen and the specimen information for the specimen of previous measurements from the database DB41, and prepares a specimen information table 184*a* and numeric data table 184*c* from this information, and displays these tables in the specimen information table display region 184*b* and numeric data table display region 184*d*, and further displays the patient information in the patient information display region 184*e*. As shown in FIG. 31, the specimen information table 184*a* has a specimen number field 184*f*, measuring apparatus ID field 184*h*, measurement time field 184*i*, and measurement value fields 184*j*, 184*k*, 184*m*, 184*n*, 184*o*, 184*p*, 184*q*, and 184*r*. The specimen number field 184*f* displays the specimen numbers of previously measured specimens. The measuring apparatus ID field 184*h* displays the ID of the measuring apparatus that measured the specimen. The measurement time field 184*i* displays the time the specimen was measured. the measurement values of the specimen are displayed in the measurement value fields 184*j*, 184*k*, 184*m*, 184*n*, 184*o*, 184*p*, 184*q*, and 184*r*. A measurement item tab 184*s* is provided at the bottom of the specimen information table display region 184*b*. Only the case in which the CA tab 184*s* is provided is described below. That is, in the first embodiment, the CA tab 184*s* is normally selected, and only the specimen information table 184*a* related to the measurement items of the blood coagulation measuring apparatuses can be displayed. Measurement values PT_% (prothrombin active percent), PT_R (prothrombin ratio), PT_INR (prothrombin INR (international standard ratio)), APTT, Fbg, Fbg_C (fibrinogen concentration), AT3_dOD (antithrombin III optical density change rate), AT3_% (antithrombin III active percent), APL_dOD (antiplasmin optical density change rate) and the like are displayed in the measurement value fields 184*j*, 184*k*, 184*m*, 184*n*, 184*o*, 184*p*, 184*q*, and 184*r* of the specimen information table 184*a*. The specimen number field 184*f*, measuring apparatus ID field 184*h*, and measurement time field 184*i* are displayed when any tab is selected.

When the user selects the row related to a single specimen number among the records displayed in the specimen information table 184*a*, the selected row is displayed highlighted in a different color than the other rows. Then, the CPU 51*a* displays the measurement values for the selected specimen number in the numeric value data table 184*c*. As shown in FIG. 31, the numeric value data table 184*c* has a measurement item field 184*v*, numeric value data field 184*w*, and unit field 184*x* in the blood coagulation measurement. The measurement item field 184*v* displays the name of the measurement item. The numeric data field 184*w* displays the measurement values of the specimen corresponding to the measurement item of that row. The unit field 184*x* displays the units of the measurement values of that row. The user can confirm the measurement results of the blood coagulation measuring apparatus 4*a* by the display in the measurement result display window. Furthermore, the data flow from the reception of the measurement value data from the blood coagulation measuring apparatus 4*a* to the display of the measurement result display window by the data processing apparatus 5 is identical to the data flow of the data processing apparatus 3 described using FIG. 28, and therefore further description is omitted.

In this way the measurement result display window 184 is configured the same as the measurement result display window 84 in the previously described application program 34*a*. Similar to the previously described start window, this allows the measurement result display window 184 to be displayed by the basic display module 35*a* used jointly with the application program 34*a*. Furthermore, user convenience is improved by the unified user interface. Moreover, the unified user interface can be expected to improve the design and development efficiency of the application programs 34*a* and 54*a* since the user interface is realized by common modules.

When the user inputs instructions to display the details of the measurement results, the CPU 51*a* reads the measurement value data from the database DB41, and displays the data in the measurement result detail display window. In the first embodiment, the measurement result detail display window opens when the user double clicks the specimen information table 184*a* in the measurement result display window 184, and details of the double-clicked data are displayed in the measurement result detail display window, similar to the display of the measurement result detail display window in the previously described application program 34*a*. The measurement result details display window is also displayed when the user left clicks the data browser button in the menu window.

Figure 32:
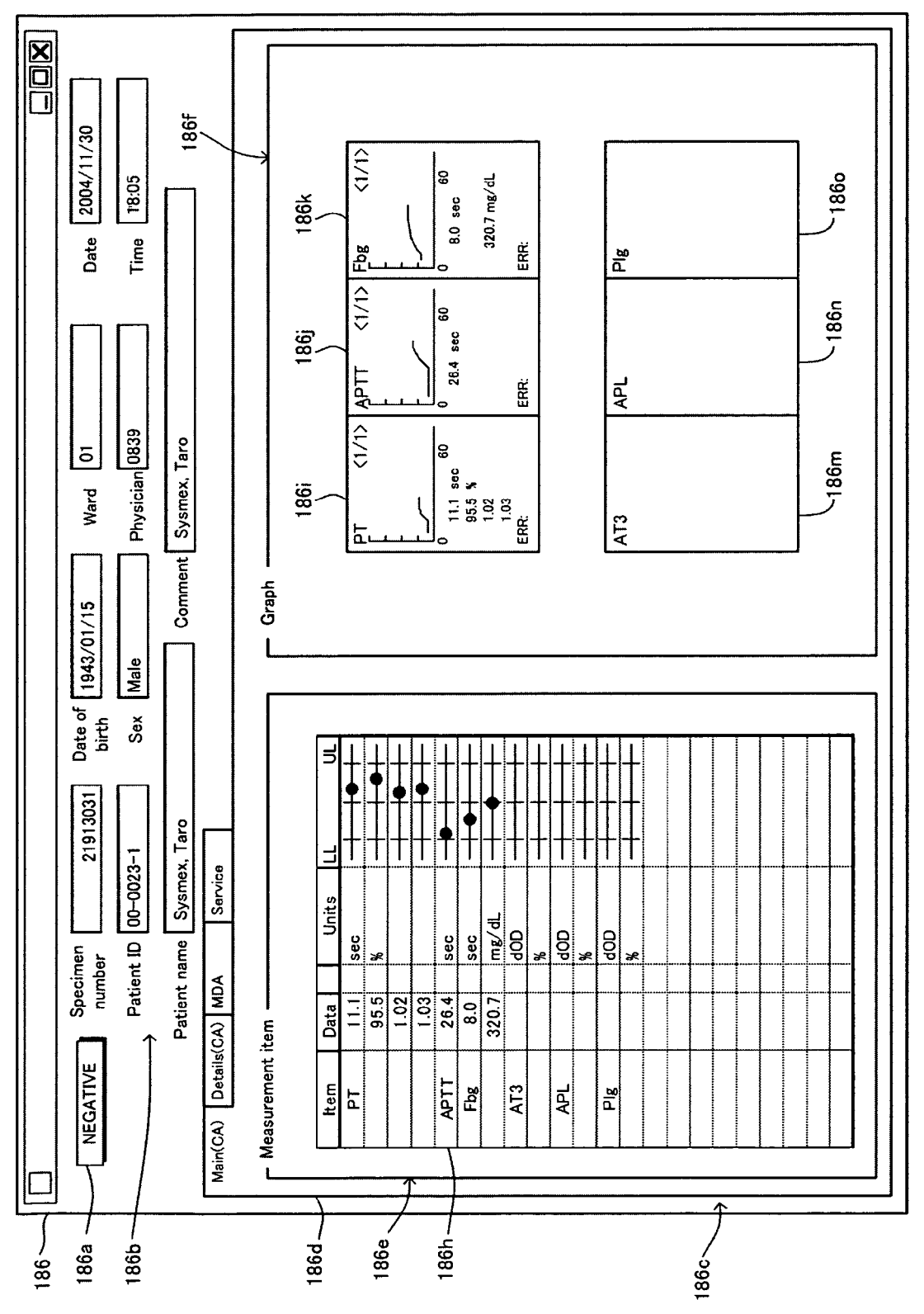

FIG. 32 is a schematic view showing the structure of the measurement result detail display window 186. As shown in FIG. 32, the measurement result detail display window 186 has an anomaly display region 186*a* for displaying whether or not the measurement result is anomalous, specimen information display region 186*b* for displaying specimen information, and detailed information display region 186*c* for displaying various types of details of the measurement results. Similar to the measurement result detail display window 86 shown in FIG. 29, the anomaly display region 186*a* is provided at the top left of the measurement result detail display window 186; [positive] is displayed when an anomaly is found in a measurement result, and the type of anomaly is display by double clicking [positive]. [Negative] is displayed in the anomaly display region 186*a* when there is no anomaly or measurement error. Furthermore, since the specimen information display region 186*b* is identical to the specimen information display region 86*b* of the measurement result detail display window 86 shown in FIG. 29, further description is omitted.

The detailed information display region 186*c* displays a window for displaying detailed information related to the types of measurement results. FIG. 32 illustrates when the blood coagulation measurement main window 186*d* is displayed in the detailed information display region 186*c*. The coagulation measurement main window 186*d* has a numeric data display region 186*e* for displaying numeric data of each measurement item, and a graph display region 186*f* for graphic displays of coagulation curves of each measurement item.

The numeric data display region 186*e* displays numeric data table 186*h* that shows the numeric data and units for each measurement item. The numeric data table 186*h* has measurement item, numeric data, and unit fields, and displays the numeric data of each measurement item in table format similar to the numeric data table 86*h* in the measurement result detail display window 86 shown in FIG. 29. The numeric data table 186*h* displays an SD bar representing a graphical table of the dislocation from the normal range of measurement values for each measurement item, and the user can easily confirm the extent of such variation of the measurement values from the normal range by this means.

The graph display region 186*f* displays coagulation curve graphs, measurement value data, and calculated numeric data for each measurement item. FIG. 32 shows six measurement items PT, APTT, Fbg, AT3, APL, and Plg as measurement objects. The graph display region 186*h* has display regions 186*i*, 186*j*, 186*k*, 186*m*, 186*n*, 186*o* arranged in a matrix for each measurement item, and coagulation curve graphs, measurement value data, and calculated numeric data for each measurement item are displayed in the respective display regions 186*i*, 186*j*, 186*k*, 186*m*, 186*n*, 186*o*. The coagulation curve graph has the scattered light intensity plotted on the vertical axis, and the time plotted on the horizontal axis. Below the coagulation curve graph are displayed the coagulation time or dOD (percentage change in optical density) for each item. Below the coagulation time (dOD) are displayed numeric data of the calculation items. Since measurement data are present in the measurement items PT, APTT, and Fbg in FIG. 32, coagulation curve graphs are displayed in the display regions 186*i*, 186*j*, 186*k* for these measurement items, but the display regions 186*m*, 186*n*, 186*o* are blank for the measurement items AT3, APL, Plg since there are no measurement data for these items.

In addition to the coagulation measurement main window 186*d*, the measurement item detail windows for each measurement item and the like may be opened in the detailed information display region 186*c*. These windows can be displayed by switching among the windows using the tabs provides at the top of the detailed information display region 186*c*. For example, when [Main (CA)] tab is left clicked, the coagulation measurement main window 186*d* is displayed, when the [Detail] tab is left clicked, the measurement item detail window is displayed.

In this way the measurement result detail display window 186 of the data processing apparatus 5 has different display content in the detail display region 186*c* relative to the measurement result detail display window 86 of the data processing apparatus 3, although the structure of the other windows (for example, the arrangement of the anomaly display region 186*a*, specimen information display region 186*b*, and detailed information display region 186*c*) are identical. As described above, the content displayed in the detailed information display region 186*c* is characteristics of the blood coagulation measuring apparatus, and the display content of the detailed information display region 186*c* cannot be in common with the measurement result detail display window 86. Conversely, the parts other than the detailed information display region 186*c* that is, the content of the anomaly display region 186*a* and specimen information display region 186*b* match the content of the hemocyte analyzer. The measurement result detail display windows 86 and 186 display much common information, such that the window structure of the measurement result detail display window 186 can be common to many parts of the measurement result detail display region 86. Regarding the content displayed in the detailed information display region 186*c*, the structures of those parts having matching display content with the numeric data table 186*h* and detailed information display region 86*c* may be used jointly in common. A user is provided with common operation characteristics by unifying the user interfaces of the data processing apparatuses 3 and 5, thus reducing as much as possible the operation sequences the user must learn for each data processing apparatus and improving user convenience. Moreover, the unified user interface can be expected to improve the design and development efficiency of the application programs 34*a* and 54*a* since the user interface is realized by common modules.

The operation of the analysis system 1 is described below when a manager user (chief clinician or the like) who is allowed to reference all data of the hemocyte analyzers 2*a* and 2*b* and blood coagulation measuring apparatuses 4*a* and 4*b* confirms the measurement results of the hemocyte analyzers 2*a* and 2*b* and blood coagulation measuring apparatuses 4*a* and 4*b* using the data processing apparatus 6. First, the user starts the application program 64*a*. In this case, similar to the application program 34*a*, the CPU 61*a* of the computer 6*a* displays a logon window on the display unit 62, and the user verification is performed when the logon ID and password input are received. When user verification is successful, the start window is displayed on the display unit 62. The display process of the start window is the main function of the basic display module 35*a*.

The structure of the start window is identical to the structure of the start window 81 of the application program 34*a* used by the hemocyte analyzers 2*a* and 2*b* shown in FIG. 24, and the structure of the start window of the application program 54*a* used by the blood coagulation measuring apparatuses 4*a* and 4*b*. This window is used to display the start window by the basic display module 35*a* jointly used by the application programs 34*a* and 54*a*. The number of development processes of the application programs 34*a*, 54*a*, and 64*a* can be reduced by making parts of the structures of the application programs common to all. Furthermore, the burden on the user of having different user interfaces for each application program can be reduced by having a unified user interface, thereby improving the user convenience.

When the user left clicks the measurement record button in the main menu of the start window, the CPU 61a displays the measurement record window 282 (refer to FIG. 25). The measurement record window 282 has a measurement item group selection box 282a provided a the top of the window, a measurement item table display region 282c for displaying a measurement item table 282, measurement item list display region 282e for displaying a measurement item list 282d, specimen information input region 282f for inputting specimen information, patient information display region 282g for displaying patient information, and button display region 82o for displaying a plurality of buttons 282h, 282i, 282j, 282k, 282m, 282n, 282o for selecting measurement selection items. In this way the structure of the measurement record window 282 is similar to the structure of the measurement record window 82 of the application program 34a. Therefore, further description of the structure of the measurement record window 282 is omitted.

The data processing apparatus 6 is capable of performing operation settings for all hemocyte analyzers 2a and 2b and blood coagulation measuring apparatuses 4a and 4b. Accordingly, in the data processing apparatus 6, the previously mentioned measurement items groups [MCC] and [CA_coagulation method] are set. The user can select a desired measurement item group from the measurement item group selection box 282a. When [MCC] is selected, the CPU 61a accesses the database DB21 on the hard disk 61d, and displays the measurement record window 282 which is similar to the measurement record window 82 of the data processing apparatus 3 shown in FIG. 25. When [CA_coagulation method] is selected, the CPU 61a accesses the database DB41 on the hard disk 61d, and displays the measurement record window which is similar to the measurement record window 182 shown in FIG. 30. The processes of the CPU 61a and the usage methods of the measurement record window 282 are identical to the processes of the CPUs 31a and 51a and the usage methods of the measurement record windows 812 and 182 of the data processing apparatuses 3 and 5.

When the specimen hemocyte analysis starts, the user sets a collection tube containing the specimen in the rack, and places the rack in the transport unit provided at the front of the hemocyte analyzer 2a (2b). The collection tubes are transported in each rack by the transport unit, and the barcode (specimen number) is read during transit by a barcode reader, and the specimen number data are sent to the data processing apparatus 6. The CPU 61a acquires the measurement items corresponding to the specimen number from database DB21 or the database server 7, and stores the measurement item data in the order management buffer provided in the RAM 61c, similar to the process in the previously described data processing apparatus 3. Thereafter, when a send data request that requests the transmission of measurement items is received from the hemocyte analyzer 2a, the data processing apparatus 6 acquires the measurement item data corresponding to the specimen number data included in the send data request from the order management buffer, and sends the measurement item data to the hemocyte analyzer 2a.

Thereafter, when the suctioning of the specimen from the collection tube ends in the hemocyte analyzer 2a, a suction completion notification indicating the completion of the suction operation is from the hemocyte analyzer 2a to the data processing apparatus 6. The data processing apparatus 6 acquires the measurement items corresponding to the specimen number data included in the suction completion notification from the order management buffer, and associates the data with the specimen number and stores the data in the database DB21.

Next, the hemocyte analyzer 2a supplies the specimen suctioned from the collection tube to any among the optical detection unit 21, RBC detection unit 22, HGB detection unit 23, and IMI detection unit 24, and starts the measurement of those measurement items received from the data processing apparatus 6. After the measurements are completed, the measurement value data are sent from the hemocyte analyzer 2a to the data processing apparatus 6. When the measurement value data are received, the CPU 61a associates the data with the specimen number and records the data in the database DB21.

Conversely, when coagulation measurement of a sample starts, the user sets the collection tube containing the specimen in a rack, and places the rack in the transport unit provided in the front part of the blood coagulation measuring apparatus 4a (4b). The collection tubes are transported in each rack by the transport unit, and the barcode data are read during transit by a barcode reader, and the specimen number data are sent to the data processing apparatus 6. The CPU 61a acquires measurement items corresponding to the specimen number from the database DB41 or database server 7, and stores the measurement item data in the order management buffer provided in the RAM 61c. Thereafter, when a send data request that requests the transmission of measurement items is received from the blood coagulation measuring apparatus 4a, the data processing apparatus 6 acquires the measurement item data corresponding to the specimen number data included in the send data request from the order management buffer, and sends the measurement item data to the blood coagulation measuring apparatus 4a. The flow of the data in this case is identical to the flow of the data in the data processing apparatus 3 described in FIG. 26, and further description is therefore omitted.

Thereafter, when the suctioning of the specimen from the collection tube ends in the blood coagulation measuring apparatus 4a, a suction completion notification indicating the completion of the suction operation is from the blood coagulation measuring apparatus 4a to the data processing apparatus 6. The data processing apparatus 6 acquires the measurement items corresponding to the specimen number data included in the suction completion notification from the order management buffer, and associates the data with the specimen number and stores the data in the database DB41.

Then, the blood coagulation measuring apparatus 4a supplies the specimen suctioned from the collection tube to the measurement unit 41, and starts the measurements according to the measurement items received from the data processing apparatus 6. After the measurements are completed, the measurement value data are sent from the blood coagulation measuring apparatus 4a to the data processing apparatus 6. When the measurement value data are received, the CPU 61a associates the data with the specimen number and records the data in the database DB41. Since the data flow of hemocyte analysis and blood coagulation measurements of a sample using the data processing apparatus 6 described above are identical to the data flow when using the data processing apparatus 3 described using FIG. 26, further description is omitted.

In this way measurement items can be provided for both the hemocyte analyzers 2a and 2b and the blood coagulation measuring apparatuses 4a and 4b using the data processing apparatus 6, and the measurement data of the hemocyte analyzers 2a and 2b and blood coagulation measuring apparatuses 4a and 4b are received by the data processing apparatus 6, and the measurement values are recorded in the databases DB21 and DB41 provided in the data processing apparatus 6. Accordingly, even when one or another of the data processing apparatuses 3 and 5 is impaired and cannot be used, measurements by the hemocyte analyzers 2a and 2b and the blood coagulation measuring apparatuses 4a and 4b can still be performed using the data processing apparatus 6.

When the user inputs instructions to display the measurement results, the CPU 61a reads the measurement value data from the databases DB21 and DB41, and displays the data in the measurement result display window. In the first embodiment, the display of the measurement result display window is executed when the user left clicks the sample explorer button in the menu window.

Figure 33:
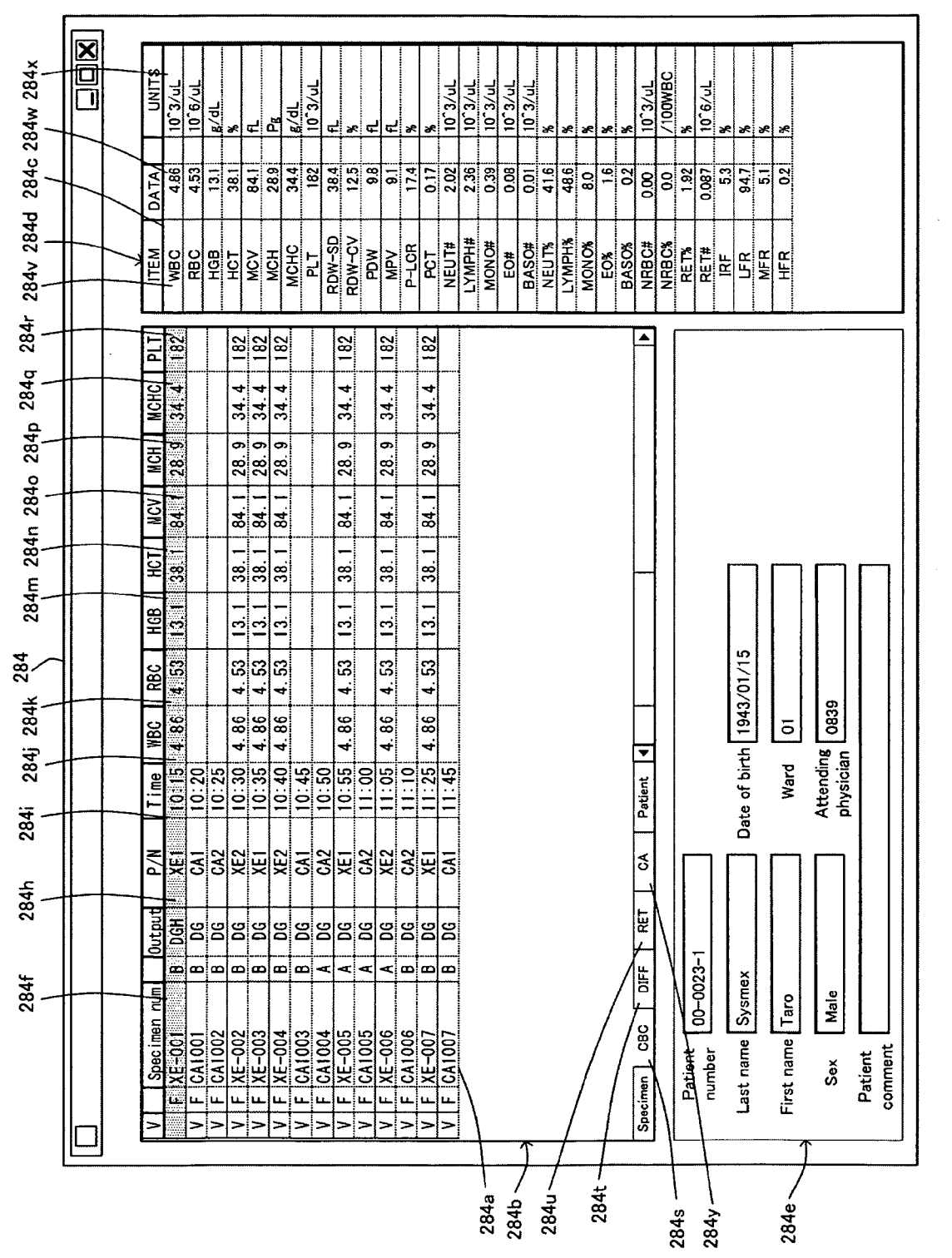

FIG. 33 is a schematic view showing the structure of the measurement result display window 284. As shown in FIG. 33, the measurement result display window 284 has a specimen information table display region 284b for displaying a specimen information table 284a, numeric data table display region 284d for displaying a numeric data table 283c, and patient information display region 284e for displaying patient information. The patient information display region 284e is identical to the patient information display region 84e of the measurement result display window 84 shown in FIG. 27, and therefore further description is omitted.

As described above, when the sample explorer button is left clicked, the CPU 61a acquires the measurement value data for the specimen and the specimen information for the specimen of previous measurements from the databases DB21 and DB41, and prepares a specimen information table 284a and numeric data table 284c from this information, and displays these tables in the specimen information table display region 284b and numeric data table display region 284d, and further displays the patient information in the patient information display region 284e. As shown in FIG. 33, the specimen information table 284a has a specimen number field 284f, measuring apparatus ID field 284h, measurement time field 284i, and measurement value fields 284j, 284k, 284m, 84n, 284o, 284p, 284q, and 284r. Since the fields 284f-284r of the specimen information table 284a are identical to the fields 84f-84r of the specimen information table 84a included in the measurement result display window 84 in the data processing apparatus 3 further description is omitted. Measurement item switching tabs 284s, 284t, 284u, and 284y are provided at the bottom of the specimen information table display region 284b. The case in which these tabs include CBC tab 284s, DIFF tab 284t, RET tab 284u, and CA tab 284y is described below. When the CBC tab 284s is selected, the measurement values of WBC, RBC, HGB, HCT, MCV, MCH, MCHC, and PLT are displayed in the measurement value fields 284j, 284k, 284m, 284m, 284n, 284o, 284p, 284q, and 284r. When the DIFF tab 284t is selected, the specimen information table 284a is switched and the measurement values of DIFF measurement items are displayed in the measurement value fields. When the RET tab 284u is selected, the measurement values for the RET measurement items are displayed in the measurement value field, and when the CA tab 284y is selected, the measurement values for blood coagulation measurement items are displayed in the measurement value field. Thus, the CBC tab 284s, DIFF tab 284t, and RET tab 284u for displaying measurement values of measurement items of the hemocyte analyzers 2a and 2b, and the CA tab 284y for displaying measurement values of the measurement items of the blood coagulation measuring apparatuses 4a and 4b are provided in the measurement result display window 284 of the data processing apparatus 6, such that the measurement results of both the hemocyte analyzers 2a and 2b and the blood coagulation measuring apparatuses 4a and 4b can be displayed by switching these tabs. The specimen number field 284f, measuring apparatus ID field 284h, and measurement time field 284i are displayed when any tab is selected. An NRBC tab may also be provided, and when this tab is selected, the measurement values for NRBC measurement items are displayed.

The measurement results read from the database DB21 (that is, measurement results of the hemocyte analyzers 2a and 2b), and the measurement results read from the database DB41 (that is, the measurement results of the blood coagulation measuring apparatuses 4a and 4b) can be mixed and displayed in the specimen information table 284a. In this case, when a tab for displaying the measurement values of the measurement items of the hemocyte analyzers 2a and 2b (for example, CBC tab 284s) is selected, the mass of measurement items in the rows for measurement results of the blood coagulation measuring apparatuses 4a and 4b are blank since there are no measurement values for measurement items of the hemocyte analyzers in the data of measurement results for the blood coagulation measuring apparatuses 4a and 4b.

When the user selects the row related to a single specimen number among the records displayed in the specimen information table 284a, the selected row is displayed highlighted in a different color than the other rows. Then, the CPU 61a displays the measurement values for the selected specimen number in the numeric value data table 284c. As shown in FIG. 33, the numeric data table 284c is provided with a measurement item field 284v, numeric data field 284w, and unit field 284x. When the measurement result row of the hemocyte analyzers 2a and 4a are selected in the specimen information table 284a, the names of the measurement items of the hemocyte analyzers 2a and 4a are displayed in the measurement item field 284v of the numeric data table 284c. The numeric data field 284w displays the measurement values of the specimen corresponding to the measurement item of that row. The unit field 284x displays the units of the measurement values of that row. When the measurement results of the blood coagulation measuring apparatuses 4a and 4b are selected in the specimen information table 284a, the display of the numeric data table 284c is switched, and the names of the measurement items of the blood coagulation measuring apparatuses 4a and 4b are displayed in the measurement item field 284v, the measurement values of the specimen corresponding to the measurement items of this row are displayed in the numeric data field 284w, and the units of the measurement values of that row are displayed in the unit field 284x. The user can confirm the measurement results of the hemocyte analyzers 2a and 2b and the blood coagulation measuring apparatuses 4a and 4b by displaying the results in the measurement results display window 284. Furthermore, the data flow from the reception of the measurement data from the hemocyte analyzers 2a and 2b and blood coagulation measuring apparatuses 4a and 4b until the measurement result display window is displayed by the data processing apparatus 6 is identical to the data flow of the data processing apparatus 3 previously described using FIG. 28, and therefore further description is omitted.

In this way the measurement result display window 284 is configured the same as the measurement result display windows 84 and 184 in the previously described application programs 34a and 54a. Similar to the previously described start window, this allows the measurement result display window 284 to be displayed by the basic display module 35a used jointly with the application programs 34a and 54a. Furthermore, user convenience is improved by the unified user interface. Moreover, the unified user interface can be expected to improve the design and development efficiency of the application programs 34a, 54a and 64a since the common user interface is realized by common modules.

Using the data processing apparatus 6, the user selectively switches among the measurement results and analysis results of the hemocyte analyzers 2a and 2b, and the measurement results and analysis results of the blood coagulation measuring apparatuses 4a and 4b, and validates the analysis results by confirming the measurement results of different types displayed on the screen. Analysis result validation is executed when the user operates the input unit 33 and selects the validate menu not shown in the drawings while the analysis results of the object to be validated are selected. Analysis result validation may be executed by the data processing apparatuses 3 and 5 as well as the data processing apparatus 6. Therefore, since measurement results and analysis results of the measurement item groups can be confirmed simply by selecting the tab of the measurement item group using the data processing apparatus 6, different types of measurement results can be easily referenced and not only the measurement results obtained by the same measuring apparatus as performed the analysis results being validated, but also the measurement results obtained by different types of measuring apparatuses can be used as judging criteria for validating analysis results, thereby improving the validity of result validation.

Quality control of different types of measuring apparatuses 2a (2b) and 4a (4b) can be easily performed by a single data processing apparatus 6 by executing measurements using the hemocyte analyzers 2a and 2b and blood coagulation measuring apparatuses 4a and 4b using well known control materials that produce normal measurement results and analysis results, displaying these measurement results and analysis results and comparing normal measurement results and analysis results using the data processing apparatus 6. Since a conventional dedicated data processing apparatus can only perform quality control for a single type of measuring apparatus, a user must perform quality control of various measuring apparatuses by moving among each dedicated data processing apparatus to perform quality control of a plurality of types of measuring apparatuses, such that the present invention reduces much complex labor and greatly improves user convenience.

Since the measurement results and analysis results of the hemocyte analyzers 2a and 2b and blood coagulation analyzers 4a and 4b can be selectively switched and displayed according to the specimen number, the user can easily confirm various measurement results and analysis results for the same specimens, which is extremely convenient. Although the validated analysis results are sent to and stored on the database server 7, the user can obtain more detailed analysis result information than is included in the measurement results using the data processing apparatus 6 without accessing the database server 7 to confirm the analysis results. This aspect eliminates a great deal of the accesses the database server 7, thus reducing the load on the database server 7 and improving performance of the entire analysis system 1.

When the user inputs instructions to display the details of the measurement results, the CPU 61a reads the measurement value data from the databases DB21 and DB41, and displays the data in the measurement result detail display window. In the first embodiment, the measurement result detail display window opens when the user double clicks the specimen information table 284a in the measurement result display window 284, and details of the double-clicked data are displayed in the measurement result detail display window, similar to the display of the measurement result detail display window in the previously described application programs 34a and 54a. The measurement result details display window is also displayed when the user left clicks the data browser button in the menu window.

Figure 34:
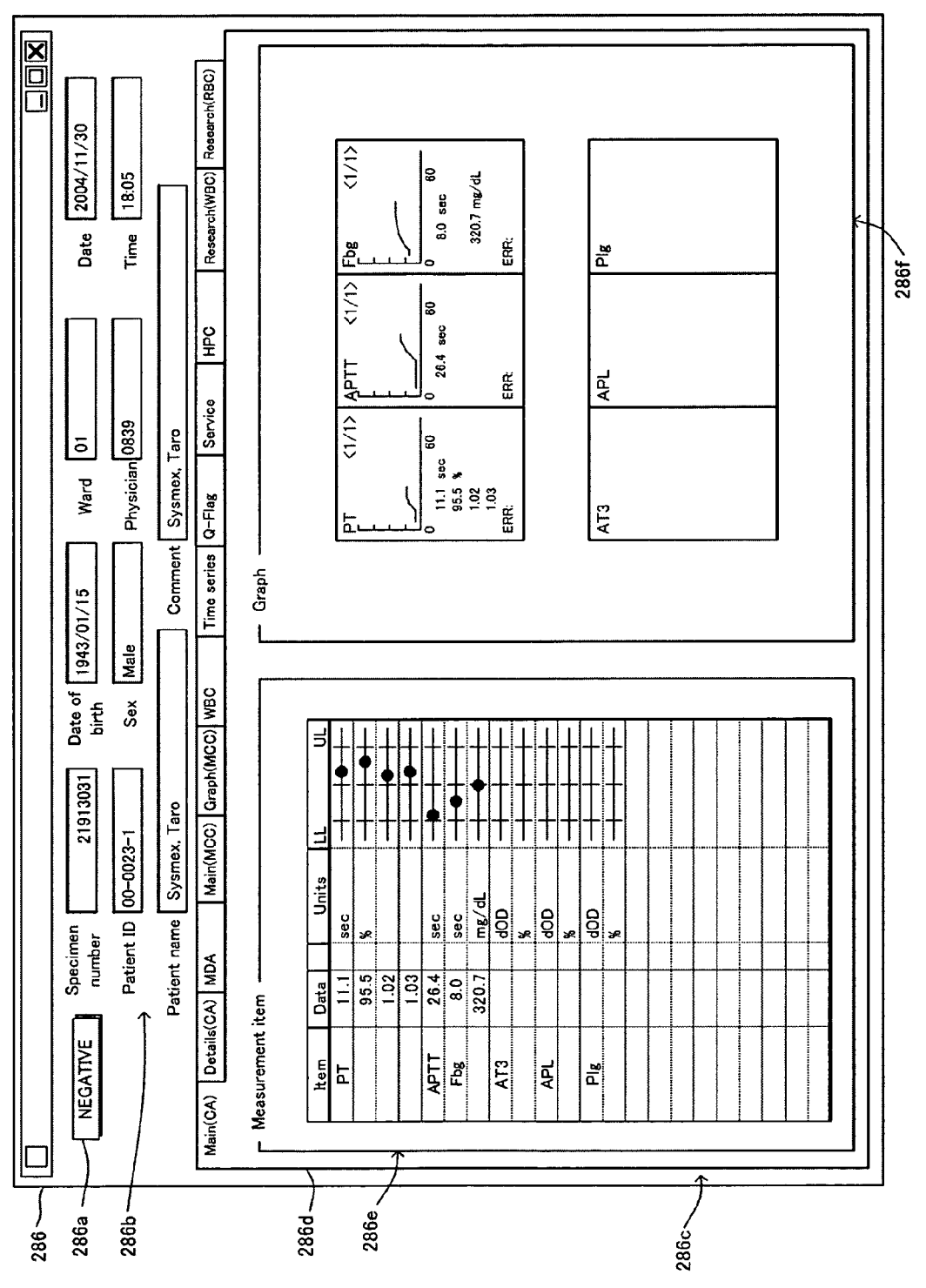

FIG. 34 is a schematic view showing the structure of the measurement result detail display window 286. As shown in FIG. 34, the measurement result detailed information display window 286 has an anomaly display region 286a for displaying whether or not the measurement result is anomalous, specimen information display region 286b for displaying specimen information, and detailed information display region 286c for displaying various types of details of the measurement results. Similar to the measurement result detail display windows 86 and 186 shown in FIGS. 29 and 32, the anomaly display region 286a is provided at the top left of the measurement result detail display window 286; [positive] is displayed when an anomaly is found in a measurement result, and the type of anomaly is display by double clicking [positive]. [Negative] is displayed in the anomaly display region 286a when there is no anomaly or measurement error. Furthermore, since the specimen information display region 286b is identical to the specimen information display regions 86b and 186b of the measurement result detail display windows 86 and 186 shown in FIGS. 29 and 32, further description is omitted.

The detailed information display region 286c displays a window for displaying detailed information related to the types of measurement results. FIG. 34 illustrates when the blood coagulation measurement main window 286d is displayed in the detailed information display region 286c. The coagulation measurement main window 286d has a numeric data display region 286e for displaying numeric data of each measurement item, and a graph display region 286f for graphic displays of coagulation curves of each measurement item. Since the blood coagulation measurement main window 286d is identical to the blood coagulation measurement main window 186d displayed in the detailed information display region 186c of the measurement result detail display window 186 of the data processing apparatus 5, further description is omitted.

A hemocyte analysis main window for displaying detailed information of hemocyte measurement results, a graph window for displaying graphs of measurement results, WBC window for displaying detailed information of white blood cells, RBC window for displaying detailed information of red blood cells, and a measurement item detail window for displaying detailed information of each measurement item of the blood coagulation measurements can be opened in the detailed information display region 286c. These windows can be displayed by switching among the windows using the tabs provides at the top of the detailed information display region 286c. For example, when [Main (MCC)] tab is left clicked, the hemocyte analysis main window is displayed; when the [MAIN (CA)] tab is left clicked, the coagulation measurement main window 286d is displayed; when the [Graph (MCC)] tab is left clicked, the graph window is displayed; and when the [Details] tab is left clicked, the measurement item detail window is displayed.

In this way the measurement result detail display window 286 of the data processing apparatus 6 can display windows (for example, hemocyte analysis main window, graph window) in the detailed information display region 86c of the measurement result detail display window 86 of the data processing apparatus 3 and can display windows (for example, coagulation measurement main window, measurement item detail window) in the detailed information display region 186c of the measurement result detail display window 186 of the data processing apparatus 5, and in this aspect the measurement result detail display window 286 differs from the measurement result detail display windows 86 and 186 of the data processing apparatuses 3 and 5, whereas other window structures (for example, the arrangement of the anomaly display region 286a, specimen information display region 286b, and detailed information display region 286c) are identical to the measurement result detail display windows 86 and 186. As described above, the windows displayed in the detailed information display region 286c are windows displayed in common in the detailed information display regions 86c and 186c of the measurement result detail display windows 86 and 186. Accordingly, the program modules related to the displays of these windows can be used in common as program modules of the application programs 34a and 54a. Furthermore, the parts other than the detailed information display region 186c that is, the content of the anomaly display region 186a and specimen information display region 186b match the content of the hemocyte analysis. Accordingly, the program modules related to the displays of these parts can be used in common as program modules of the application programs 34a and 54a. The design and development efficiency of the application programs 34a, 54a, and 64a are improved by the common use of the program modules among the application programs 34a, 54a, and 64a. A user is provided with common operation characteristics by unifying the user interfaces of the data processing apparatuses 3, 5, and 6, thus reducing as much as possible the operation sequences the user must learn for each data processing apparatus and improving user convenience.

Figure 35:
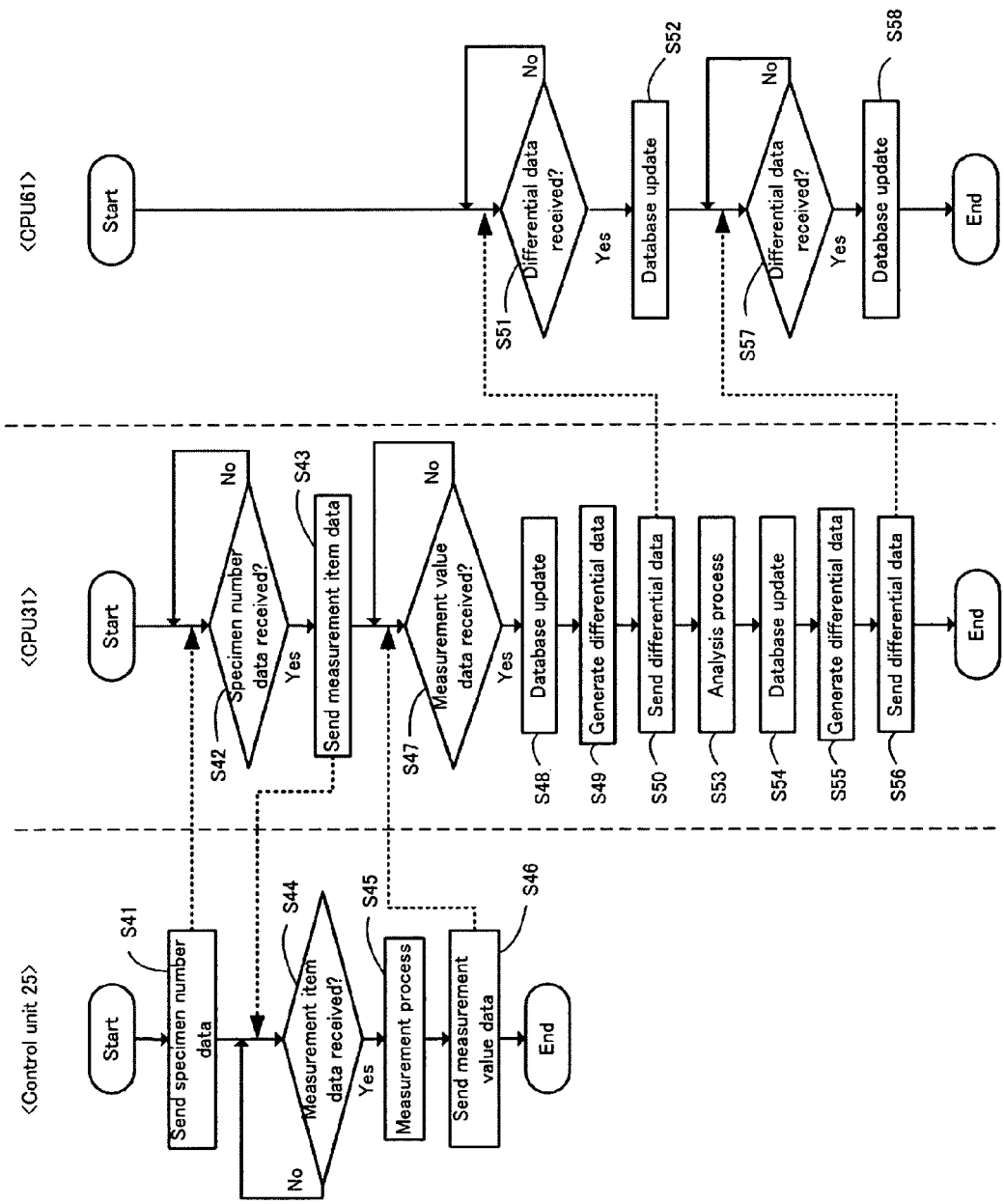
FIG. 35 is a flow chart illustrating the operation flow related to the fault tolerance of the analysis system of the first embodiment.

Operations related to fault tolerance of the analysis system 1 of the first embodiment are described below. FIG. 35 is a flow chart illustrating the operation flow related to the fault tolerance of the analysis system of the first embodiment. When measurements are performed by the hemocyte analyzer 2a, the operator, as previously described, sets the collection tube containing the specimen in the rack, and places the rack in the transport unit provided in the front part of the hemocyte analyzer 2a. The specimen number is read from the barcode by a barcode reader provided in the hemocyte analyzer 2a while the collection tubes in each rack are conveyed by the transport unit. The control unit 25 of the hemocyte analyzer 2a sends the specimen number data to the data processing apparatus 3 (step S41). When the specimen number data from the hemocyte analyzer 2a are received (step S42: YES), the CPU 31a sends the measurement item data corresponding to the send request from the hemocyte analyzer 2a to the hemocyte analyzer 2a (step S43). When the measurement item data are received (step S44: YES), the control unit 25 suctions the specimen from the collection tube to the sample supply unit, and starts the measurement (step S45). The control unit 25 generates measurement values by these measurements, and sends the measurement value data to the data processing apparatus 3, which was the issuing source of the measurement order (step S46).

When the measurement value data are received (step S47: YES), the CPU 31a stores the received measurement value data in the database DB21, and updates the database (step S48). Then, the CPU 31a generates differential data of the pre-update and post-update state If the database DB21, that is, generates data representing the difference in the database DB21 produced by the update (step S49), and sends the differential data to the data processing apparatus 6 (step S50). When the differential data are received (step S51: YES), the CPU 61a of the data processing apparatus 6 updates the database DB21 on the hard disk 61d using the differential data (step S52). Since the differential data are data representing the difference in the pre-update and post-update state of the database DB21, the database DB21 of the data processing apparatus 6 is coordinated with the updated database DB21 of the data processing apparatus 3 using the differential data. Since this process is performed immediately after the update of the database DB21 of the data processing apparatus 3, the database DB21 is essentially mirrored in real time.

The CPU 31a executes analysis processes such as hemocyte count, white cell type and the like based on the measurement values (step S53). The generated measurement result data are stored in the database DB21, and the database DB21 is updated (step S54). Then, the CPU 31a generates differential data of the pre-update and post-update state f the database DB21 (step S55), and sends the differential data to the data processing apparatus 6 (step S56), whereupon the process ends. When the differential data are received (step S57: YES), the CPU 61a of the data processing apparatus 6 updates the database DB21 on the hard disk 61d using the differential data (step S58), and the process ends.

Although the flow charts shown in FIG. 35 illustrate the flows of the dual processes of the databases DB21 when measurements are performed by the hemocyte analyzer 2a, actually, the database DB21 duality is accomplished by the4 CPU 31a generating an interrupt when the database DB21 is updated on the data processing apparatus 3, generating differential data, and sending the differential data to the data processing apparatus 6 without inquiring whether or not the database DB21 has been updated by a measurement execution by the hemocyte analyzer 2a.

Thus, since the data required for the update is sent to the data processing apparatus 6 by the timing that the database DB21 of the data processing apparatus 3 requires updating, the contents match on the databases DB21 of the data processing apparatuses 3 and 6. Therefore, since there are dual databases DB21, the database DB21 is backed up in its latest iteration or a state near the latest iteration on the data processing apparatus 6, and data can be processed continuously using the database DB21 without stopping the system even when, for example, the data processing apparatus 3 malfunctions and cannot operate.

Similarly, the database DB22 on the data processing apparatus 6 can be updated using data required for the update sent to the data processing apparatus 6 with the timing that the database DB22 requires updating due to, for example, changes of the setting values or the like of the data processing apparatus 3. Although omitted to simplify the description, the situation is identical for databases DB41 and DB42.

The present invention is not limited to the previously mentioned structure inasmuch as, for example, the data processing apparatuses 3, 5, and 6 may mirror the databases DB21, DB22, DB41, DB42 at predetermined time intervals, such that the contents of the databases DB21 and DB22 of the data processing apparatus 3 and the databases DB21 and DB 22 of the data processing apparatus 6 match, and the contents of the databases DB41 and DB42 of the data processing apparatus 5 and the databases DB41 and DB42 of the data processing apparatus 6 match; and when measurements are executed by the hemocyte analyzers 2a and 2b (blood coagulation analyzers 4a and 4b) the measurement value data are sent simultaneously to the data processing apparatus 3 (5) and data processing apparatus 6, such that the databases DB21 (DB41) are mirrored by updating the databases DB21 (DB41) simultaneously on the data processing apparatuses 3 (5), and 6 by the sent measurement values. In this case, when the data processing apparatus 3 (5) performs an analysis process and generates analysis result data, the analysis result data may be sent to the data processing apparatus 6, and the data processing apparatus 6 may updates the database DB21 (DB41) using these analysis result data.

In the first embodiment, the data processing apparatuses 3 and 5 generate differential data of pre-update and post-update conditions of the databases DB21, DB22, DB41, and DB42, and send the differential data to the data processing apparatus 6, and the data processing apparatus 6 updates the databases DB21, DB22, DB41, and DB42 to the new state; however, the present invention is not limited to this process inasmuch as the data processing apparatuses 3 and 5 may generate differential data of the pre-update and post-update state of the databases DB21, DB22, DB41, and DB42 at predetermined internals, ands these differential data may be sent to the data processing apparatus 6, and the data processing apparatus 6 then uses these differential data to update the databases DB21, DB22, DB41, and DB42 to the new state.

Although the first embodiment has been described as a configuration wherein setting data are read from the databases DB22 and DB42 during the operation of the application programs 34a, 54a, and 64a, and a data tree is developed by processing the setting data, the present invention is not limited to this configuration inasmuch as, for example, a setting database itself may designated as a data tree structure database, such that setting data are read from the database to directly develop a data tree in memory, or a database stored on the hard disks 31d, 41d, 61d that can be directly accessed. Furthermore the structure is not limited to a tree structure, and may be a data structure such as a table format, list format or the like insofar as the [setting conditions], and [setting values] [with each [setting item].

Second Embodiment

Figure 36:
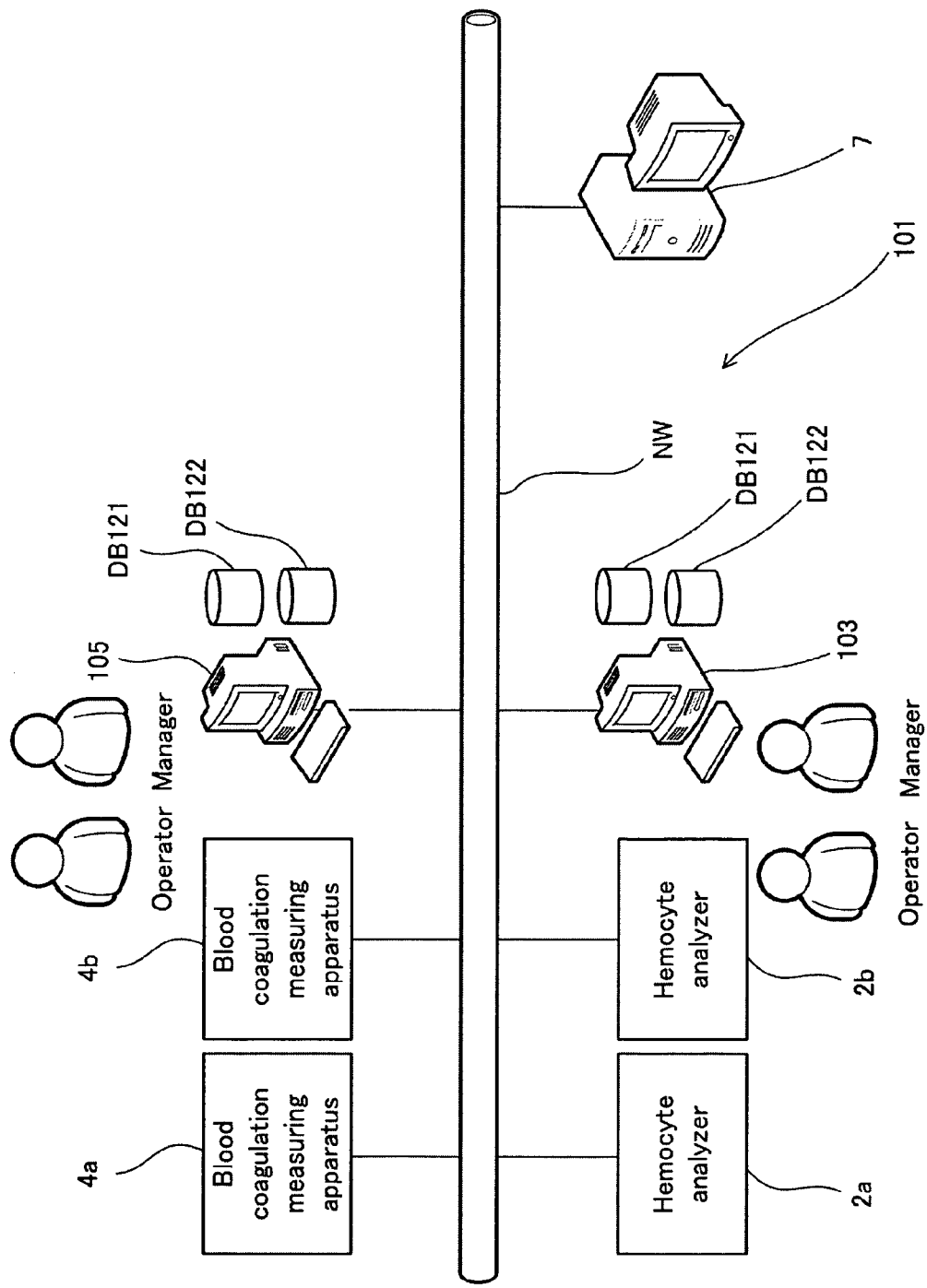
FIG. 36 is a schematic view showing the structure of the analysis system of a second embodiment.

FIG. 36 is a schematic view showing the structure of the analysis system of a second embodiment. As shown in FIG. 36, the analysis system 101 of the second embodiment has essential structural elements that include hemocyte analyzers 2a and 2b, data processing apparatus 103 for hemocyte analyzers 2a and 2b, blood coagulation measuring apparatuses 4a and 4b, data processing apparatus 105 for blood coagulation measuring apparatuses 4a and 4b, and patient data management database server 7. The hemocyte analyzers 2a and 2b, data processing apparatus 103, blood coagulation measuring apparatuses 4a and 4b, data processing apparatus 105, and database server 7 are installed within an medical institution such as, for example, a hospital or pathology research facility. Furthermore, the hemocyte analyzers 2a and 2b, data processing apparatus 103, blood coagulation measuring apparatuses 4a and 4b, data processing apparatus 105 may be provided, for example, in a pathology research facility, and the database server 7 may be installed in a hospital or the like, such that the apparatuses configuring the analysis system 101 are separately provided at a plurality of separate institutions. The hemocyte analyzers 2a and 2b, data processing apparatus 103, blood coagulation measuring apparatuses 4a and 4b, data processing apparatus 105, and database server 7 are connected so as to be capable of mutual communication over a network NW, such as the Internet, LAN, or dedicated line such as a telephone line. The data processing apparatus 103 is installed near the hemocyte analyzers 2a and 2b, and is used for data processing related to the hemocyte analyzers 2a and 2b. Conversely, the data processing apparatus 105 is installed near the blood coagulation measuring apparatuses 4a and 4b, and is used for data processing related to the blood coagulation measuring apparatuses 4a and 4b. The hemocyte analyzers 2a and 2b, blood coagulation measuring apparatuses 4a and 4b, and database server 7 are identical to the structures of the analysis system 1 of the first embodiment, and like structural elements are designated by like reference numbers, therefore, further description is omitted.

Figure 37:
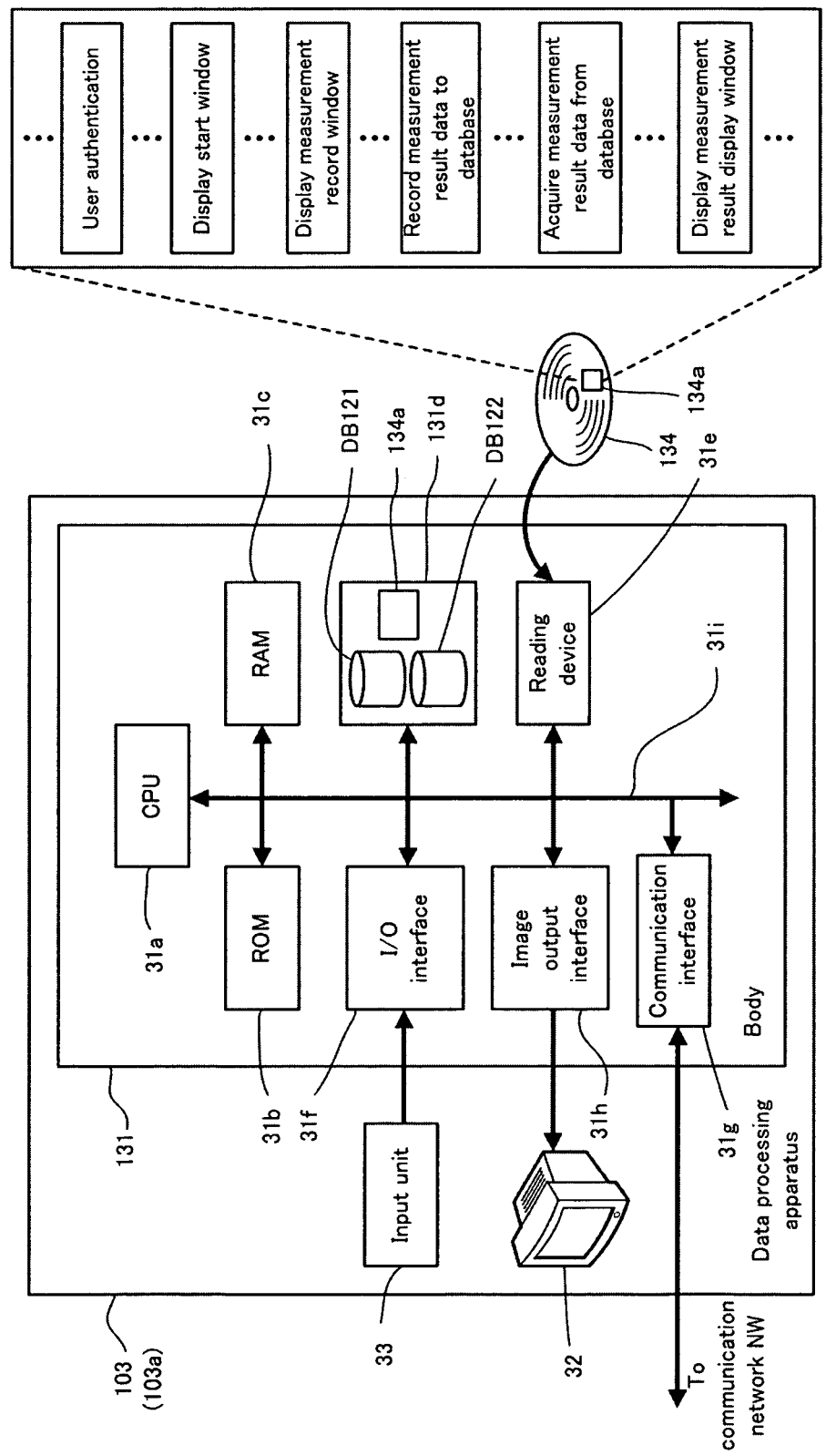
FIG. 37 is a block diagram showing the structure of the data processing apparatus of the hemocyte analyzer of the second embodiment.

The structure of the data processing apparatus 103 is described below. FIG. 37 is a block diagram showing the structure of the data processing apparatus 103 of the second embodiment. The data processing apparatus 103 is mainly configured by a computer 103a which includes a body 131, display unit 32, and input unit 33. The body 31 mainly includes a CPU 31a, ROM 31b, RAM 31c, hard disk 31d, reading device 31e, I/O interface 31f, communication interface 31g, and image output interface 31h, and the CPU 31a, ROM 31b, RAM 31c, hard disk 131d, reading device 31e, I/O interface 31f, communication interface 31g, and image output interface 31h are connected by a bus 31i.

Databases DB121 and DB122 are installed on the hard disk 131d of the data processing apparatus 103. The database DB121 is a relational database for associating and storing specimen numbers with the measurement result data of the hemocyte analyzers 2a and 2b, and blood coagulation measuring apparatuses 4a and 4b. The measurement result data obtained by the measurements performed by the hemocyte analyzers 2a and 2b and blood coagulation measuring apparatuses 4a and 4b are stored in the database DB 121 by an application program 134a executed by the CPU 31a. The application program 134a can also access the database DB 121, read past measurement result data, and display the data on the display unit 32.

The database DB122 is a tree structure database for storing setting values of the application programs 134a and 154a. since the structure of the database DB122 is identical to the structure of the database DB22 described in the first embodiment, further description is omitted.

The portable recording medium 134 stores the application program 134a which allows a computer to function as a data processing apparatus for a measuring apparatus; the computer 103a can read the application program 134a from the portable recording medium 134, and install the application program 134a on the hard disk 131d.

The application program 134a is a computer program providing functions such as operation settings for the hemocyte analyzers 2a and 2b and blood coagulation measuring apparatuses 4a and 4b, providing measurement items, reception of measurement results, recording of measurement results to the database DB 121, and display of measurement results and the like, and the application program 134a makes the computer 103a function as a data processing apparatus 103 provided with the above-mentioned functions when executed by the CPU 31a. Since the application program 134a is capable of recording, deleting, modifying, and acquiring measurement result data in the database DB 121, and otherwise has the same structure as the application program 64a of the first embodiment, further description is omitted.

Since the data processing apparatus 103 has the application program 134a, and databases DB121 and DB122 installed on the hard disk 131d, and otherwise has a structure identical to that of the data processing apparatus 3 described in the first embodiment, further description is omitted.

Figure 38:
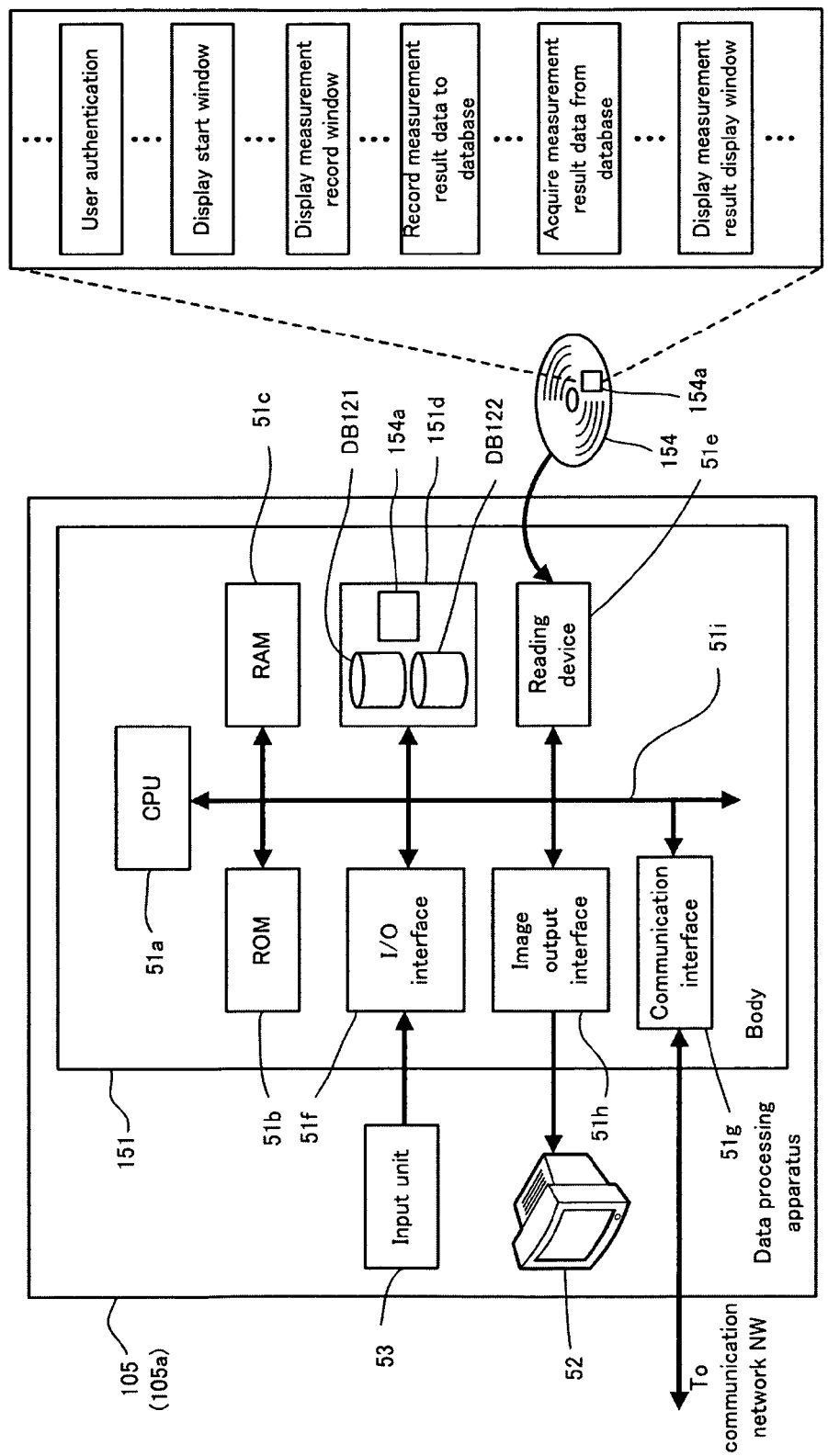
FIG. 38 is a block diagram showing the structure of the data processing apparatus of the blood coagulation measuring apparatus of the second embodiment.

The structure of the data processing apparatus 105 is described below. FIG. 38 is a block diagram showing the structure of the data processing apparatus 105 of the second embodiment. The data processing apparatus 105 is mainly configured by a computer 105a which includes a body 151, display unit 52, and input unit 53. The body 151 is mainly configured by a CPU 51a, ROM 51b, RAM 51c, hard disk 151d, reading device 51e, I/O interface 51f, communication interface 51g, and image output interface 51h; the CPU 51a, ROM 51b, RAM 51c, hard disk 51d, reading device 51e, I/O interface 51f, communication interface 51g, and image output interface 51h are connected by a bus 51i.

Databases DB 121 and DB 122 are installed on the hard disk 151d of the data processing apparatus 105. The databases DB121 and DB122 installed on the hard disk 151d are databases having the same content as the databases DB 121 and DB 122 provided in the previously described processing apparatus 103. The databases DB121 and DB 122 are synchronized in real time with the databases DB 121 and DB 122 provided in the data processing apparatus 103 through the functions of the application programs 134a and 154a. In this way the data processing of the measurement results of the hemocyte analyzers 2a and 2b can be performed by the data processing apparatus 105 even when a malfunction occurs in the data processing apparatus 103, and, similarly, the data processing of the measurement results of the blood coagulation measuring apparatuses 4a and 4b can be performed by the data processing apparatus 103 even when a malfunction occurs in the data processing apparatus 105.

The portable recording medium 154 stores the application program 154a which allows a computer to function as a data processing apparatus for a measuring apparatus; the computer 105a can read the application program 154a from the portable recording medium 154, and install the application program 154a on the hard disk 511d.

The application program 154a is a computer program providing functions such as operation settings for the hemocyte analyzers 2a and 2b and blood coagulation measuring apparatuses 4a and 4b, providing measurement items, reception of measurement results, recording of measurement results to the database DB 122, and display of measurement results and the like, and the application program 154a makes the computer 105a function as a data processing apparatus 105 provided with the above-mentioned functions when executed by the CPU 51a. The application program 154a can record, delete, modify, and acquire measurement results in the database DB122 provided on the hard disk 151d, and otherwise is identical to the structure of the application program 64a described in the first embodiment, and therefore further description is omitted.

Since the data processing apparatus 105 has the application program 154a, and databases DB121 and DB122 installed on the hard disk 51d, and otherwise has a structure identical to that of the data processing apparatus 5 described in the first embodiment, further description is omitted.

In the analysis system 101 of the second embodiment, the operation settings and operation start instructions of the hemocyte analyzers 2a and 2b and blood coagulation measuring apparatuses 4a and 4b can be performed, and the measurement results of the hemocyte analyzers 2a and 2b and blood coagulation measuring apparatuses 4a and 4b can be displayed, by a user using the data processing apparatus 103. Moreover, the operation settings and operation start instructions of the hemocyte analyzers 2a and 2b and blood coagulation measuring apparatuses 4a and 4b can be performed, and the measurement results of the hemocyte analyzers 2a and 2b and blood coagulation measuring apparatuses 4a and 4b can be displayed, by a user using the data processing apparatus 105. The data processing apparatuses 103 and 105 can restrict the functions usable by each user. For example, user authority may be set for the data processing apparatuses 103 and 105 can be set such that operators of the hemocyte analyzers 2a and 2b are permitted use of only the functions of displaying measurement results and operating instructions for the hemocyte analyzers 2a and 2b, and prohibited from using other functions. Furthermore, user authority may be set for the data processing apparatuses 103 and 105 can be set such that operators of the blood coagulation measuring apparatuses 4a and 4b are permitted use of only the functions of displaying measurement results and operating instructions for the blood coagulation measuring apparatuses 4a and 4b, and prohibited from using other functions. User authority of the data processing apparatuses 103 and 105 may be set such that a manager user (chief clinician or the like) who is allowed to reference the all data of the hemocyte analyzers 2a and 2b and blood coagulation measuring apparatuses 4a and 4b is allowed to use all functions.

Operations related to fault tolerance of the analysis system 101 of the second embodiment are described below. The hemocyte analyzers 2a and 2b, blood coagulation measuring apparatuses 4a and 4b, and data processing apparatus 103 (105) send data required for updating to another data processing apparatus 105 (103) with a timing of necessary update of the databases DB121 and DB122. The data processing apparatus 105 (103) receiving the data updates the databases DB121 and DB122 with these data, thus achieving dual databases. In the second embodiment, the data processing apparatus 103 and the data processing apparatus 105 mirror the databases DB121 and DB122 at predetermined time intervals, such that the contents of the databases DB121 and DB122 of the data processing apparatus 103 and the databases DB121 and DB122 of the data processing apparatus 105 match. Thus, the system is capable of continuous operation without interruption even when one or another of the data processing apparatuses 103 and 105 breaks down, by means of the dual databases DB121 and DB122 (backup).

Other operations of the data processing apparatuses 103 and 105 of the analysis system 101 of the second embodiment are identical to the operation of the data processing apparatus 6 described in the first embodiment, and therefore further description is omitted.

Third Embodiment

Figure 39:
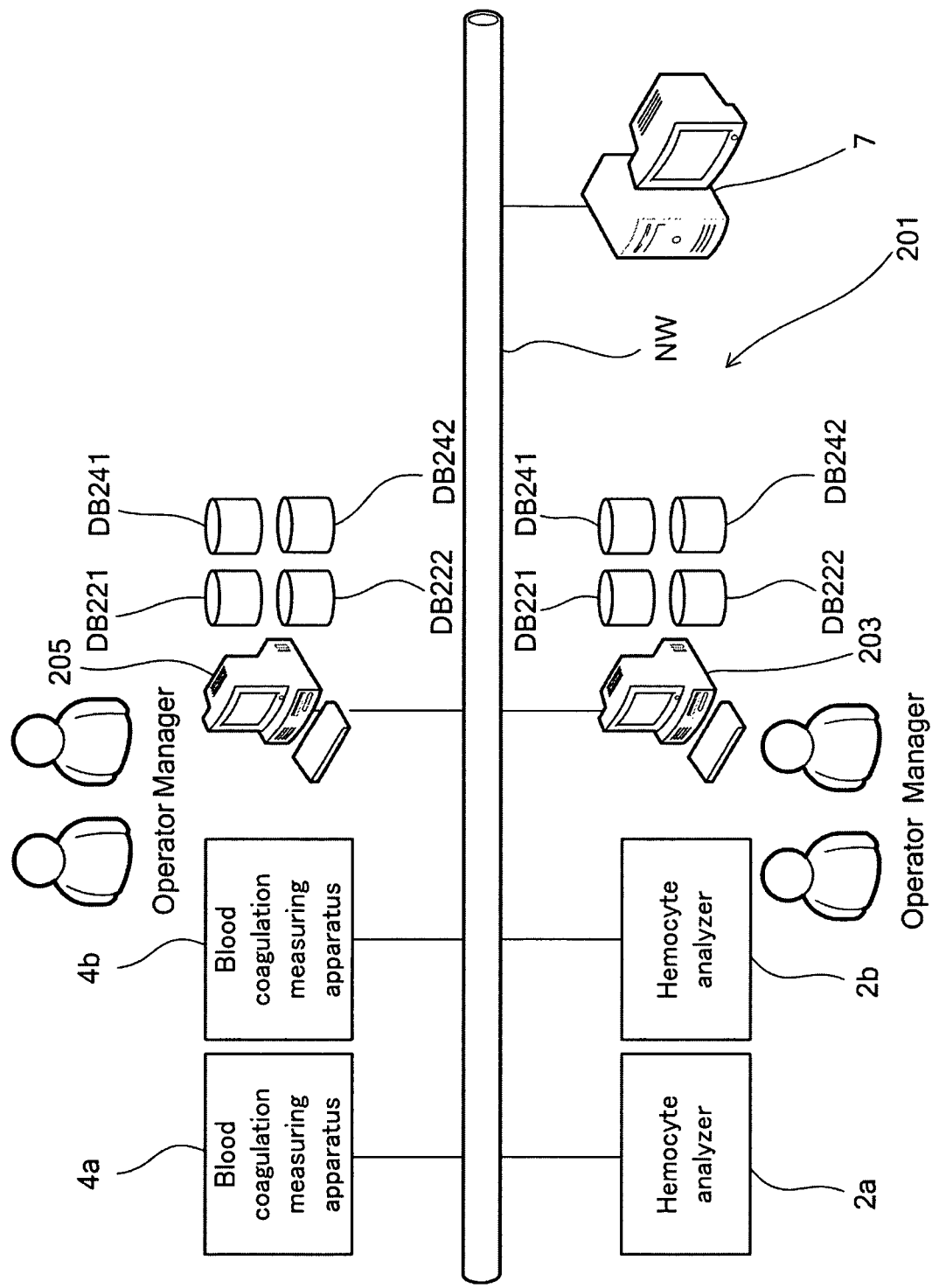
FIG. 39 is a schematic view showing the structure of the analysis system of a third embodiment.

FIG. 39 is a schematic view showing the structure of the analysis system of a third embodiment. As shown in FIG. 39, the analysis system 201 of the third embodiment has essential structural elements that include hemocyte analyzers 2a and 2b, data processing apparatus 203 for hemocyte analyzers 2a and 2b, blood coagulation measuring apparatuses 4a and 4b, data processing apparatus 205 for blood coagulation measuring apparatuses 4a and 4b, and patient data management database server 7. The hemocyte analyzers 2a and 2b, data processing apparatus 203, blood coagulation measuring apparatuses 4a and 4b, data processing apparatus 205, and database server 7 are installed within an medical institution such as, for example, a hospital or pathology research facility. Furthermore, the hemocyte analyzers 2a and 2b, data processing apparatus 203, blood coagulation measuring apparatuses 4a and 4b, data processing apparatus 205 may be provided, for example, in a pathology research facility, and the database server 7 may be installed in a hospital or the like, such that the apparatuses configuring the analysis system 201 are separately provided at a plurality of separate institutions. The hemocyte analyzers 2a and 2b, data processing apparatus 203, blood coagulation measuring apparatuses 4a and 4b, data processing apparatus 205, and database server 7 are connected so as to be capable of mutual communication through a network NW such as the Internet, LAN, dedicated telephone line or the like. The data processing apparatus 203 is installed near the hemocyte analyzers 2a and 2b, and is used for data processing related to the hemocyte analyzers 2a and 2b. Conversely, the data processing apparatus 205 is installed near the blood coagulation measuring apparatuses 4a and 4b, and is used for data processing related to the blood coagulation measuring apparatuses 4a and 4b. The hemocyte analyzers 2a and 2b, blood coagulation measuring apparatuses 4a and 4b, and database server 7 are identical to the structures of the analysis system 1 of the first embodiment, and like structural elements are designated by like reference numbers, therefore, further description is omitted.

Figure 40:
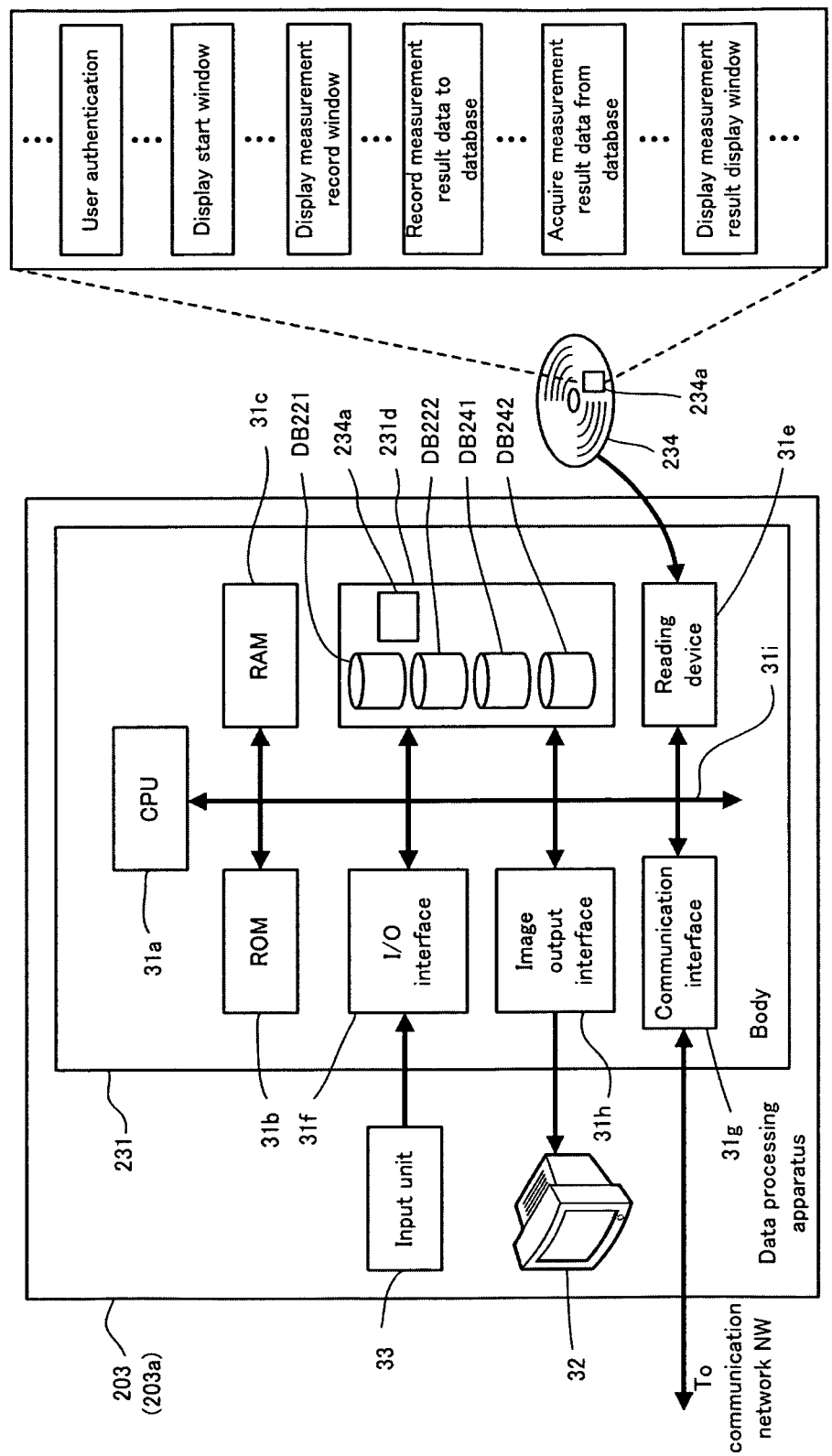
FIG. 40 is a block diagram showing the structure of the data processing apparatus of the hemocyte analyzer of the third embodiment.

The structure of the data processing apparatus 203 is described below. FIG. 40 is a block diagram showing the structure of the data processing apparatus 203 of the second embodiment. The data processing apparatus 203 is mainly configured by a computer 203a which includes a body 231, display unit 32, and input unit 33. The body 231 mainly includes a CPU 31a, ROM 31b, RAM 31c, hard disk 231d, reading device 31e, I/O interface 31f, communication interface 31g, and image output interface 31h, and the CPU 31a, ROM 31b, RAM 31c, hard disk 231d, reading device 31e, I/O interface 31f, communication interface 31g, and image output interface 31h are connected by a bus 31i.

Databases DB221, DB222, DB241, and DB242 are installed on the hard disk 231d of the data processing apparatus 203. The database DB221 is a relational database for mutually associating and storing specimen numbers and measurement result data of the hemocyte analyzers 2a and 2b. The measurement result data obtained by the measurements performed by the hemocyte analyzers 2a and 2b are stored in the database DB221 by an application program 234a executed by the CPU 31a. The application program 234a can also access the database DB221, read past measurement result data, and display the data on the display unit 32. Since the structure of the database DB221 is identical to the structure of the database DB21 described in the first embodiment, further description is omitted.

The database DB222 is a tree structure database for storing setting values of the application program 234a. Since the structure of the database DB222 is identical to the structure of the database DB22 described in the first embodiment, further description is omitted.

The databases DB241 and DB242 installed on the hard disk 231d are databases having the same content as the databases DB241 and DB242 provided in the data processing apparatus 105 described later. The databases DB241 and DB242 are synchronized in real time with the databases DB241 and DB242 provided in the data processing apparatus 205 by the functions of the application programs 234a and 254a. In this way the data processing of the measurement results of the blood coagulation measuring apparatuses 4a and 4b can be performed by the data processing apparatus 203 even when a malfunction occurs in the data processing apparatus 205.

The portable recording medium 234 stores the application program 134a which allows a computer to function as a data processing apparatus for a measuring apparatus; the computer 203a can read the application program 234a from the portable recording medium 234, and install the application program 234a on the hard disk 231d.

The application program 234a is a computer program providing functions such as operation settings for the hemocyte analyzers 2a and 2b and blood coagulation measuring apparatuses 4a and 4b, providing measurement items, reception of measurement results, recording of measurement results to the database DB221 and DB241, and display of measurement results and the like, and the application program 234a makes the computer 203a function as a data processing apparatus 203 provided with the above-mentioned functions when executed by the CPU 31a. Since the application program 234a records, deletes, and modifies, and acquires data in the databases DB221 and DB241, and otherwise is identical in structure to the application program 64a described in the first embodiment, further description is omitted.

Since the data processing apparatus 203 has the application program 234a, and databases DB221, DB222, DB241, and DB242 installed on the hard disk 231d, and otherwise has a structure identical to that of the data processing apparatus 3 described in the first embodiment, further description is omitted.

Figure 41:
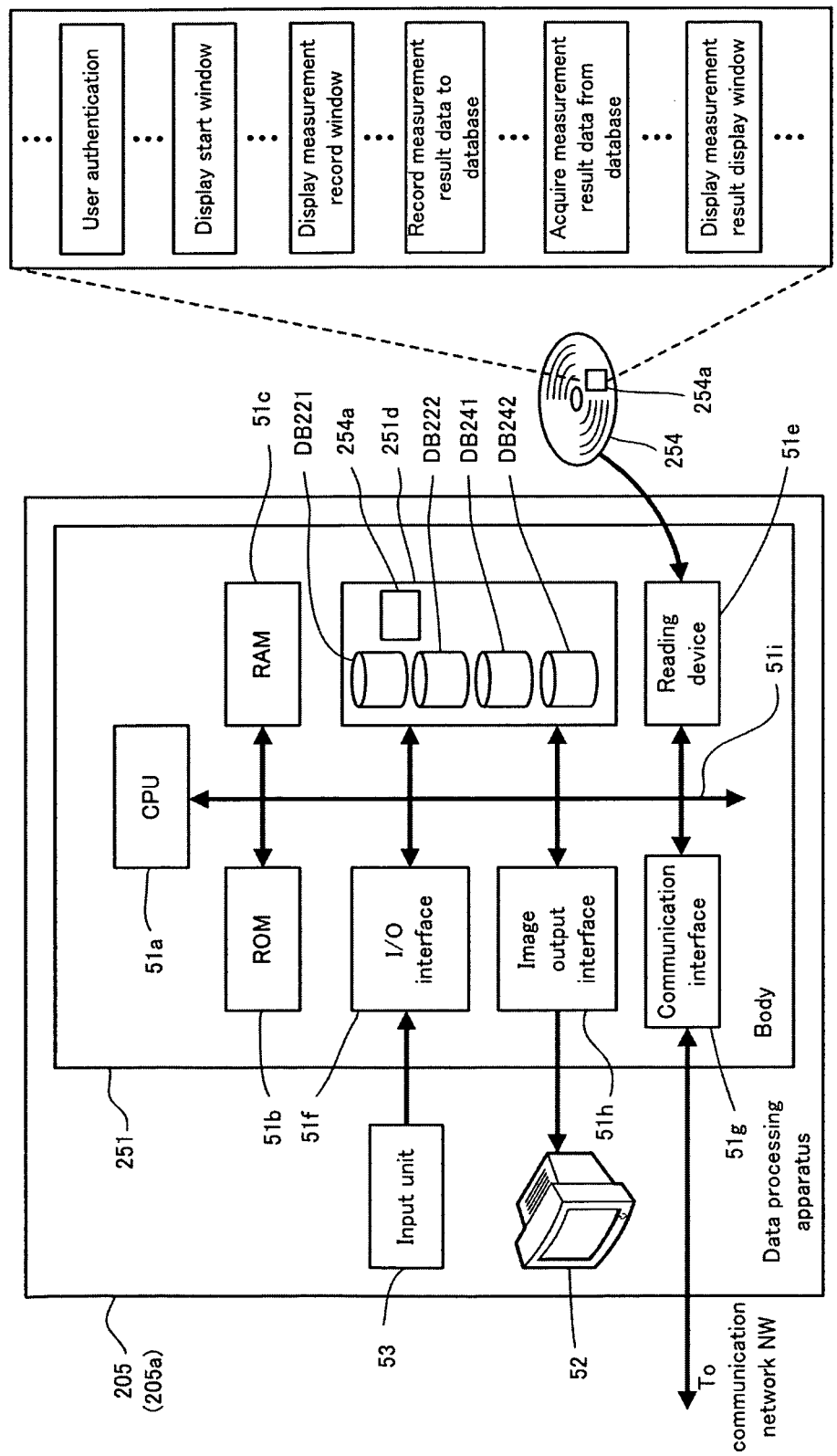
FIG. 41 is a block diagram showing the structure of the data processing apparatus of the blood coagulation measuring apparatus of the third embodiment.

The structure of the data processing apparatus 205 is described below. FIG. 41 is a block diagram showing the structure of the data processing apparatus 205 of the third embodiment. The data processing apparatus 205 is mainly configured by a computer 205a which includes a body 251, display unit 52, and input unit 53. The body 251 is mainly configured by a CPU 51a, ROM 51b, RAM 51c, hard disk 251d, reading device 51e, I/O interface 51f, communication interface 51g, and image output interface 51h; the CPU 51a, ROM 51b, RAM 51c, hard disk 251d, reading device 51e, I/O interface 51f, communication interface 51g, and image output interface 51h are connected by a bus 51i.

Databases DB221, DB222, DB241, and DB242 are installed on the hard disk 251d of the data processing apparatus 205. The database DB241 is a relational database for associating and storing specimen numbers and measurement result data of the blood coagulation measuring apparatuses 4a and 4b. The measurement result data obtained by measurements performed by the blood coagulation measuring apparatuses 4a and 4b are stored in the database DB241 by the application program 254a executed by the CPU 31a. The application program 254a can also access the database DB241, read past measurement result data, and display the data on the display unit 52. Since the structure of the database DB241 is identical to the structure of the database DB41 described in the first embodiment, further description is omitted.

The database DB242 is a tree structure database for storing setting values of the application program 254a. Since the structure of the database DB242 is identical to the structure of the database DB42 described in the first embodiment, further description is omitted.

The databases DB221 and DB222 installed on the hard disk 251d are databases having the same content as the databases DB221 and DB222 provided in the previously described processing apparatus 203. The databases DB221 and DB222 are synchronized in real time with the databases DB221 and DB222 provided in the data processing apparatus 203 by the functions of the application programs 234a and 254a. In this way the data processing of the measurement results of the hemocyte analyzers 2a and 2b can be performed by the data processing apparatus 205 even when a malfunction occurs in the data processing apparatus 203.

The portable recording medium 254 stores the application program 254a which allows a computer to function as a data processing apparatus for a measuring apparatus; the computer 205a can read the application program 254a from the portable recording medium 254, and install the application program 254a on the hard disk 251d.

The application program 254a is a computer program providing functions such as operation settings for the hemocyte analyzers 2a and 2b and blood coagulation measuring apparatuses 4a and 4b, providing measurement items, reception of measurement results, recording of measurement results to the databases DB221 and DB222, and display of measurement results and the like, and the application program 254a makes the computer 205a function as a data processing apparatus 205 provided with the above-mentioned functions when executed by the CPU 51a. Since the application program 254a records, deletes, and modifies, and acquires data in the databases DB221 and DB241, and otherwise is identical in structure to the application program 64a described in the first embodiment, further description is omitted.

Since the data processing apparatus 205 has the application program 254a, and databases DB121, DB122, DB241, and DB242 installed on the hard disk 251d, and otherwise has a structure identical to that of the data processing apparatus 5 described in the first embodiment, like structural elements are designated by like reference numbers, and further description is omitted.

In the analysis system 201 of the third embodiment, operation settings and operation start instructions for the hemocyte analyzers 2a and 2b and blood coagulation measuring apparatuses 4a and 4b can be performed, and measurement results of the hemocyte analyzers 2a and 2b and blood coagulation measuring apparatuses 4a and 4b can be displayed by the user on the data processing apparatus 203. Moreover, the operation settings and operation start instructions of the hemocyte analyzers 2a and 2b and blood coagulation measuring apparatuses 4a and 4b can be performed, and the measurement results of the hemocyte analyzers 2a and 2b and blood coagulation measuring apparatuses 4a and 4b can be displayed, by a user using the data processing apparatus 205. The data processing apparatuses 203 and 205 can restrict the functions usable by each user. For example, user authority may be set for the data processing apparatuses 203 and 205 can be set such that operators of the hemocyte analyzers 2a and 2b are permitted use of only the functions of displaying measurement results and operating instructions for the hemocyte analyzers 2a and 2b, and prohibited from using other functions. Furthermore, user authority may be set for the data processing apparatuses 203 and 205 can be set such that operators of the blood coagulation measuring apparatuses 4a and 4b are permitted use of only the functions of displaying measurement results and operating instructions for the blood coagulation measuring apparatuses 4a and 4b, and prohibited from using other functions. User authority of the data processing apparatuses 203 and 205 may be set such that a manager user (chief clinician or the like) who is allowed to reference the all data of the hemocyte analyzers 2a and 2b and blood coagulation measuring apparatuses 4a and 4b is allowed to use all functions.

Operations related to fault tolerance of the analysis system 201 of the third embodiment are described below. The hemocyte analyzers 2a and 2b, blood coagulation measuring apparatuses 4a and 4b, and data processing apparatus 203 (205) send data required for updating to another data processing apparatus 205 (203) with a timing of necessary update of the databases DB221, DB222, DB241, and DB242. The data processing apparatus 205 (203) receiving the data updates the databases DB221, DB222, DB241, and DB242 with these data, thus achieving dual databases. In the third embodiment, the data processing apparatus 203 and the data processing apparatus 205 mirror the databases DB221, DB222, DB241, and DB242 at predetermined time intervals, such that the contents of the databases DB221, DB222, DB241, and DB242 of the data processing apparatus 203 and the databases DB221, DB222, DB241, and DB242 of the data processing apparatus 205 match. Thus, the system is capable of continuous operation without interruption even when one or another of the data processing apparatuses 203 and 205 breaks down, by means of the dual databases DB221, DB222, DB241, and DB242 (backup).

Other operations of the data processing apparatuses 203 and 205 of the analysis system 201 of the third embodiment are identical to the operation of the data processing apparatus 6 described in the first embodiment, and therefore further description is omitted.

Although the first through third embodiments have been described in terms of the databases DB21, DB41, DB121, DB241 for storing measurement value data and analysis result data and the databases DB22, DB42, DB222, and DB242 for storing setting value data being duplicated to ensure reliability, the present invention is not limited to this aspect inasmuch as, for example, the data processing apparatuses 3, 5, 6, 103, 105, 203, and 205 save logs relating to the operating conditions of their own operating states in a log save database beforehand, and duplicate the log save database among other data processing apparatuses. In this case, system reliability can be ensured even, for example, when one data processing apparatus is non-operational due to malfunction, by another data processing apparatus rapidly perform a recovery operation based on the operation log of the non-operational data processing apparatus and without shutting down the operation of the system, or only briefly shutting down the system if it should shut down.

Furthermore, although the first through third embodiments have been described in terms of the analysis system 1 having hemocyte analyzers 2a and 2b and blood coagulation measuring apparatuses 4a and 4b as measuring apparatuses, wherein operating setting, operation instructions, management of measurement results, and displaying measurement results of the hemocyte analyzers 2a and 2b and blood coagulation measuring apparatuses 4a and 4b are accomplished by the data processing apparatuses 3, 5, 6, 103, 105, 203, and 205, the present invention is not limited to this configuration inasmuch as, for example, the analysis system 1 may have other measuring apparatuses, such as urine particle analyzer, urine qualitative analyzer, stool analyzer, particle analyzer and the like, so as to perform operation settings, operation instructions, manage measurement results, and display measurement results of these other measuring apparatuses.

The foregoing detailed description and accompanying drawings have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

What is claimed is:

1. An analyzing system for analyzing a specimen comprising:
   a plurality of measuring apparatuses for performing mutually different types of measurements of specimens; and
   a data processing apparatus for analysis of measurement data obtained by the plurality of measuring apparatuses to generate analysis results, wherein the data processing apparatus comprises:
      a display unit for displaying and selectively switching between a plurality of screens each showing measurement data and/or analysis results corresponding to one of the types of measurements; and
      instruction receiving means for receiving an instruction of the type of measurement corresponding to measurement data and/or analysis results to be displayed, such that the display unit displays the measurement data and/or the analysis results to be displayed in response to the instruction received by the instruction receiving means;

wherein the plurality of measuring apparatuses and the data processing apparatus are installed within a common institution.

2. The analyzing system of claim 1, wherein:
the data processing apparatus further comprises an input unit;
the display unit displays a plurality of selection symbols corresponding to a plurality of measurement types; and
the instruction receiving means receives an instruction representing the type of measurement corresponding to a selected selection symbol by receiving input that selects one selection symbol from among the plurality of selection symbols.

3. The analyzing system of claim 2, wherein the selection symbols are selected from the group consisting of icons, tabs, buttons, menus, and combinations thereof.

4. The analyzing system of claim 1, wherein the display unit displays specimen-specific information that identifies the specimen and corresponding measurement data and/or analysis results.

5. The analyzing system of claim 4, wherein the data processing apparatus further comprises a database for storing the specimen-specific information, and the measurement data and/or the analysis results.

6. The analyzing system of claim 1, further comprising:
a special data processing apparatus for analyzing measurement data of only one type of measuring apparatus, the special data processing apparatus comprising a display unit;
wherein each of the display unit of the data processing apparatus and the display unit of the special data processing apparatus displays a screen for displaying measurement data and/or analysis results of one of the plurality of measuring apparatuses; and
wherein a layout configuration of screens displayed by the display unit of the data processing apparatus substantially matches a layout configuration of screens displayed by the display unit of the special data processing apparatus.

7. The analyzing system of claim 1, wherein the data processing apparatus is configured for directing operation of the plurality of respective measuring apparatuses.

8. A data processing apparatus for analyzing measurement data of measuring apparatuses, comprising:
receiving means for receiving measurement data from a plurality of respective measuring apparatuses that perform mutually different types of measurements of specimens;
analysis processing means for performing analysis of the measurement data received from the plurality of respective measuring apparatuses to generate analysis results;
a display unit for displaying and selectively switching between a plurality of screens each showing measurement data and/or analysis results corresponding to one of the types of measurements; and
instruction receiving means for receiving an instruction of the type of measurement corresponding to measurement data and/or analysis results to be displayed, such that the display unit displays the measurement data and/or the analysis results to be displayed in response to the instruction received by the instruction receiving means;
wherein the plurality of measuring apparatuses and the data processing apparatus are installed within a common institution.

9. The data processing apparatus of claim 8, further comprising an input unit, wherein:
the display unit displays a plurality of selection symbols corresponding to a plurality of measurement types; and
the instruction receiving means receives an instruction representing the type of measurement corresponding to a selected selection symbol by receiving input that selects one selection symbol from among the plurality of selection symbols.

10. The data processing apparatus of claim 9, wherein the selection symbols are selected from the group consisting of icons, tabs, buttons, menus, and combinations thereof.

11. The data processing apparatus of claim 8, wherein the display unit displays specimen-specific information that identifies the specimens and corresponding measurement data and/or analysis results.

12. The data processing apparatus of claim 11, further comprising a database for storing the specimen-specific information, and the measurement data and/or the analysis results.

13. The data processing apparatus of claim 8, wherein a layout configuration of screens displayed by the display unit substantially matches a layout configuration of screens displayed by a display unit of a special data processing apparatus for analyzing measurement data of only one type of measuring apparatus.

14. The data processing apparatus of claim 8, wherein the data processing apparatus is configured for instructing operation of the plurality of respective measuring apparatuses.

15. A computer-readable storage medium comprising a program for processing measurement data of measuring apparatuses that measure a specimen, wherein the program comprises:
receiving means for enabling a computer to function so as to receive measurement data from a plurality of respective measuring apparatuses that perform mutually different types of measurements of specimens;
analysis processing means for enabling the computer to function so as to analyze the measurement data received from the plurality of measuring apparatuses to generate analysis results;
display means for enabling the computer to function so as to display and selectively switch between a plurality of screens each showing measurement data and/or analysis results corresponding to one type of measurement; and
instruction receiving means for enabling the computer to function so as to receive an instruction of the type of measurement corresponding to measurement data and/or analysis results to be displayed, such that the display unit displays the measurement data and/or the analysis results to be displayed in response to the instruction received by the instruction receiving means;
wherein the plurality of measuring apparatuses and the computer are installed within a common institution.

16. The computer-readable storage medium of claim 15, wherein the display means enables the computer to function so as to display specimen-specific information that identifies the specimen and corresponding measurement data and/or analysis results.

17. The computer-readable storage medium of claim 15, wherein a layout configuration of screens displayed by the display unit substantially matches a layout configuration of screens displayed by a display unit of a special data processing apparatus for analyzing measurement data of only one type of measuring apparatus.

* * * * *